(12) United States Patent
Ghebremariam et al.

(10) Patent No.: US 9,011,882 B2
(45) Date of Patent: Apr. 21, 2015

(54) DIMETHYLARGININE DIMETHYLAMINOHYDROLASE INHIBITORS AND METHODS OF USE THEREOF

(71) Applicant: The Board of Trustees of the Leland Stanford Junior University, Palo Alto, CA (US)

(72) Inventors: Yohannes T. Ghebremariam, Santa Clara, CA (US); John P. Cooke, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 13/766,336

(22) Filed: Feb. 13, 2013

(65) Prior Publication Data

US 2013/0224259 A1  Aug. 29, 2013

Related U.S. Application Data

(60) Provisional application No. 61/598,758, filed on Feb. 14, 2012, provisional application No. 61/645,383, filed on May 10, 2012, provisional application No. 61/701,990, filed on Sep. 17, 2012.

(51) Int. Cl.
| | |
|---|---|
| *A61K 9/00* | (2006.01) |
| *A61K 31/542* | (2006.01) |
| *A61K 31/4439* | (2006.01) |
| *A61K 31/437* | (2006.01) |
| *A61K 31/428* | (2006.01) |
| *A61M 11/04* | (2006.01) |
| *A61M 15/00* | (2006.01) |
| *A61M 16/14* | (2006.01) |
| *A61K 31/444* | (2006.01) |

(52) U.S. Cl.
CPC .......... *A61K 31/542* (2013.01); *A61K 31/4439* (2013.01); *A61K 31/437* (2013.01); *A61K 31/428* (2013.01); *A61M 11/04* (2013.01); *A61M 15/00* (2013.01); *A61M 16/14* (2013.01); *A61M 15/009* (2013.01); *A61K 9/00* (2013.01); *A61K 31/444* (2013.01)

(58) Field of Classification Search
None
See application file for complete search history.

(56) References Cited

U.S. PATENT DOCUMENTS

| | | | | |
|---|---|---|---|---|
| 7,786,309 | B2 * | 8/2010 | Wang et al. | 546/273.7 |
| 8,063,104 | B2 | 11/2011 | Vallance et al. | |
| 2007/0060622 | A1 * | 3/2007 | Ieni | 514/338 |
| 2009/0069331 | A1 | 3/2009 | Vallance | |
| 2011/0294878 | A1 | 12/2011 | Clement | |

FOREIGN PATENT DOCUMENTS

| | | |
|---|---|---|
| DE | 2811131 A1 | 9/1979 |
| WO | WO 2009099933 A2 * | 8/2009 |

OTHER PUBLICATIONS

Manjari, et al. "Oxidant Stress, Anti-oxidants, Nitric Oxide and Essential Fatty Acids in Peptic Ulcer Disease", 1998, Prostaglandins Leukot Essent Fatty Acids, vol. 59, No. 6, pp. 401-406.
Pullamsetti, et al. "The Role of Dimethylarginine Dimethylaminohydrolase in Idiopathic Pulmonary Fibrosis", 2011, Sci Transl Med, vol. 3, No. 87, pp. 87ra53.
Yoda, et al. "Prevention by Lansoprazole, a Proton Pump Inhibitor, of Indomethacine-induced Small Intestinal Ulceration in Rats Through Induction of Heme Oxygenase-1", 2010, J Physiol Pharmacol, vol. 61, No. 3, pp. 287-294.
Ghebremariam, et al. "Development of a Dimethylarginine Dimethylaminohydrolase (DDAH) Assay for High-Throughput Chemical Screening", 2012, Journal of Biomolecular Screening, vol. 17, No. 5, pp. 651-661.
Goodman, et al. "Association of Proton Pump Inhibitor Use on Cardiovascular Outcomes with Clopidogrel and Ticagrelor: Insights From the Platelet Inhibition and Patient Outcomes Trial", 2012, Circulation, vol. 125, pp. 978-986.
Hartzoulakis, et al. "Discovery of inhibitors of the pentein superfamily protein dimethylarginine dimethylaminohydrolase (DDAH), by virtual screening and hit analysis", 2007, Bioorg Med Chem Lett, vol. 17, No. 14, pp. 3953-3956.
Johnson, et al. "Discovery of Halopyridines as Quiescent Affinity Labels: Inactivation of Dimethylarginine Dimethylaminohydrolase", 2011, J Am Chem Soc, vol. 133, No. 5, pp. 1553-1562.
Johnson, et al. "On the mechanism of dimethylarginine dimethylaminohydrolase inactivation by 4-halopyridines", 2011, J Am Chem Soc, vol. 133, No. 28, pp. 10951-10959.
Knipp, et al. "Searching for DDAH inhibitors: S-nitroso-L-homocysteine is a chemical lead", 2005, J Am Chem Soc, vol. 127, No. 8, pp. 2372-2373.
Kotthaus, et al. "Designing modulators of dimethylarginine dimethylaminohydrolase (DDAH): a focus on selectivity over arginase", 2012, J Enzyme Inhib Med Chem, vol. 27, No. 1, pp. 24-28.
Kotthaus, et al. "Structure-activity relationship of novel and known inhibitors of human dimethylarginine dimethylaminohydrolase-1: alkenyl-amidines as new leads", 2008, Bioorg Med Chem, vol. 16, No. 24, pp. 10205-10209.
Leiper, et al. "Disruption of methylarginine metabolism impairs vascular homeostasis", 2007, Nature Medicine, vol. 13, No. 2, pp. 198-203.

(Continued)

*Primary Examiner* — Abigail Fisher
*Assistant Examiner* — Daniel L Branson
(74) *Attorney, Agent, or Firm* — Bozicevic, Field & Francis, LLP; Paula A. Borden

(57) ABSTRACT

The present disclosure provides DDAH modulators. Thus, the present disclosure provides a method of treating a patient suffering from a disorder characterized by excessive NO production and/or elevated DDAH activity, the method comprising administering to said patient an effective amount of a compound of one of formulae I-X. The present disclosure also provides a pharmaceutical composition comprising a compound of one of formulae I-X.

9 Claims, 34 Drawing Sheets

(56) References Cited

OTHER PUBLICATIONS

Linsky, et al. "Screening for dimethylarginine dimethylaminohydrolase inhibitors reveals ebselen as a bioavailable inactivator", 2011, ASC Med Chem Lett, vol. 2, No. 8, pp. 592-596.

Lluis, et al. "Characterization of C-alkyl amidines as bioavailable covalent reversible inhibitors of human DDAH-1", 2011, Chem Med Chem, vol, 6, No. 1, pp. 81-88.

Wang, et al. "Developing dual and specific inhibitors of dimethylarginine dimethylaminohydrolase-1 and nitric oxide synthase: toward a targeted polypharmacology to control nitric oxide", 2009, Biochemistry, vol. 48, No. 36, pp. 8624-8635.

Wilson, et al. "Asymmetric dimethylarginine correlates with measures of disease severity, major adverse cardiovascular events and all-cause mortality in patients with peripheral arterial disease", 2010, Vascular Medicine, vol. 15, No. 4, pp. 267-274.

Lee, et al., "Gastroesophageal Reflux Therapy is Associated with Longer Survival in Patients with Idiopathic Pulmonary Fibrosis", American Journal of Respiratory and Critical Care Medicine, 2011, vol. 184, pp. 1390-1394.

Raghu, et al., "High Prevalence of Abnormal Acid Gastro-oesophageal Reflux in Idiopathic Pulmonary Fibrosis", European Respiratory Journal, 2006, vol. 27, pp. 136-142.

Mogayzel; et al., "Cystic Fibrosis Pulmonary Guidelines. Chronic Medications for Maintenance of Lung Health.", Am. J. Respir. Crit. Care Med. (Apr. 2013), 187(7):680-9.

Raghu, "Idiopathic pulmonary fibrosis: increased survival with "gastroesophageal reflux therapy": fact or fallacy?", Am. J. Respir. Crit. Care Med. (Dec. 2011), 184(12):1330-2.

Shin; et al., "Chemistry of Covalent Inhibition of the Gastric (H+, K+)-ATPase by Proton Pump Inhibitors", J. Am. Chem. Soc.(Jun. 2004), 126(25):7800-11.

Shin; et al., "The gastric HK-ATPase: structure, function, and inhibition.", Pflugers Arch. (Jan. 2009), 457(3):609-22.

* cited by examiner

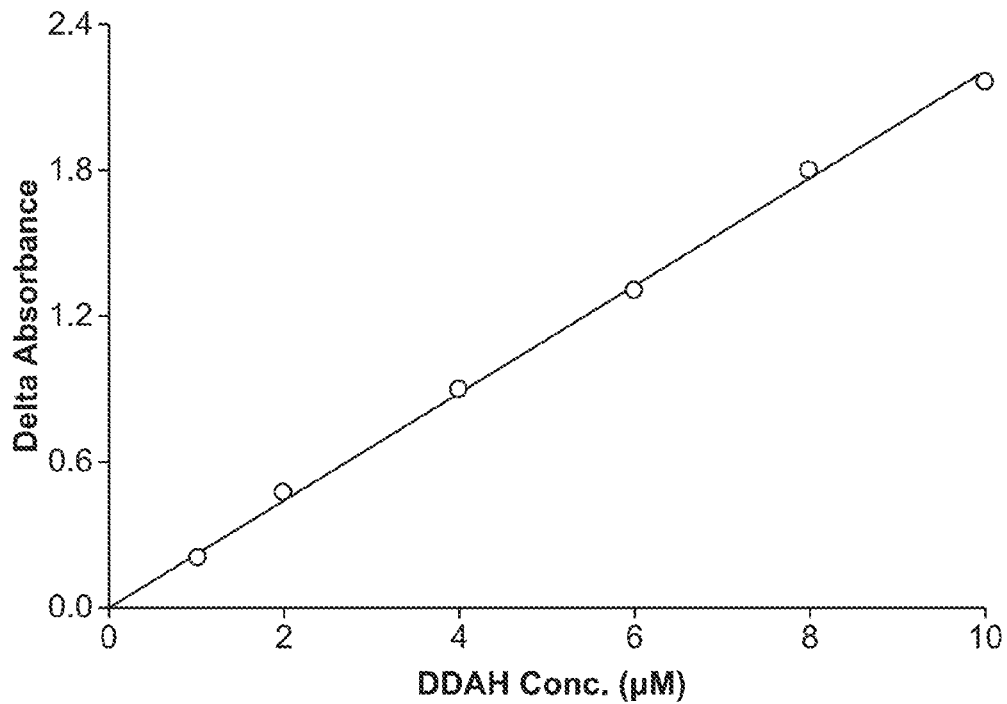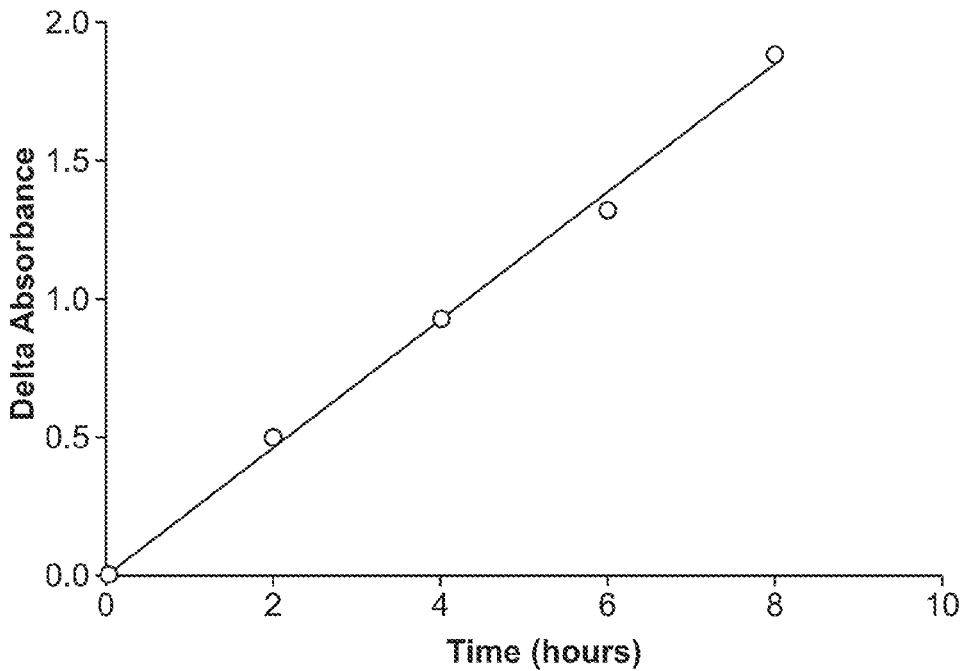
FIG. 12

```
  1 maglghpaaf grathavvra lpeslgqhal rsakgeevdv araerqhqly vgvlgskigl
 61 qvvelpades lpdcvfvedv avcceetali trpgapsrrk evdmmkeale kiqlnivemk
121 denatldggd vlftgreffv giskrtnqrg aeiladtfkd yavstvpvad glhlksfcsm
181 agpnliaigs sesaqkalki mqqmsdhryd kltvpddiaa nciylnipnk ghvllhrtpe
241 eypesakvye klkdhmlipv smselekvdg lltccsvlin kkvds
```

GenBank Accession No. CAI22051
*Homo sapiens* DDAH1

FIG. 15

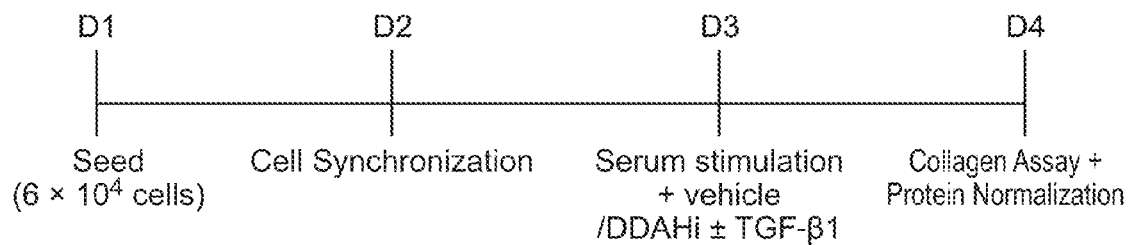
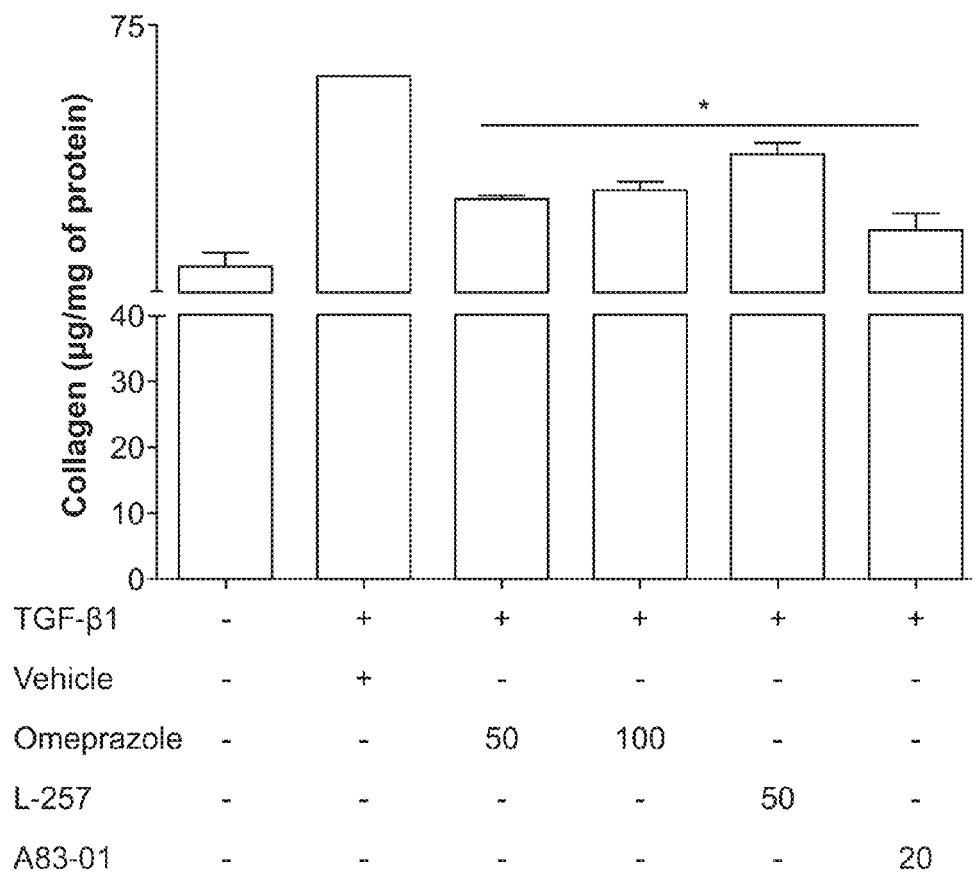
FIG. 23

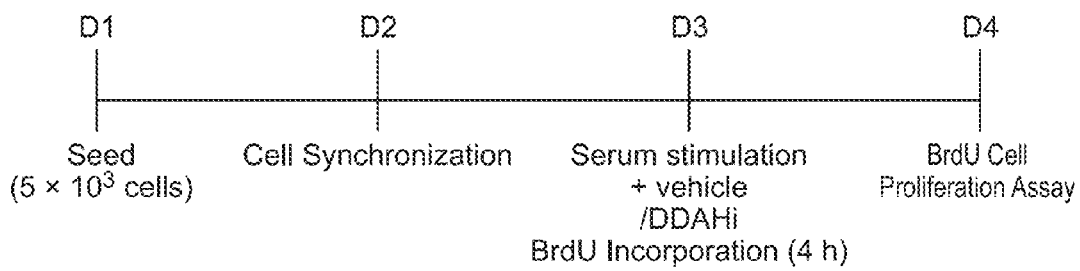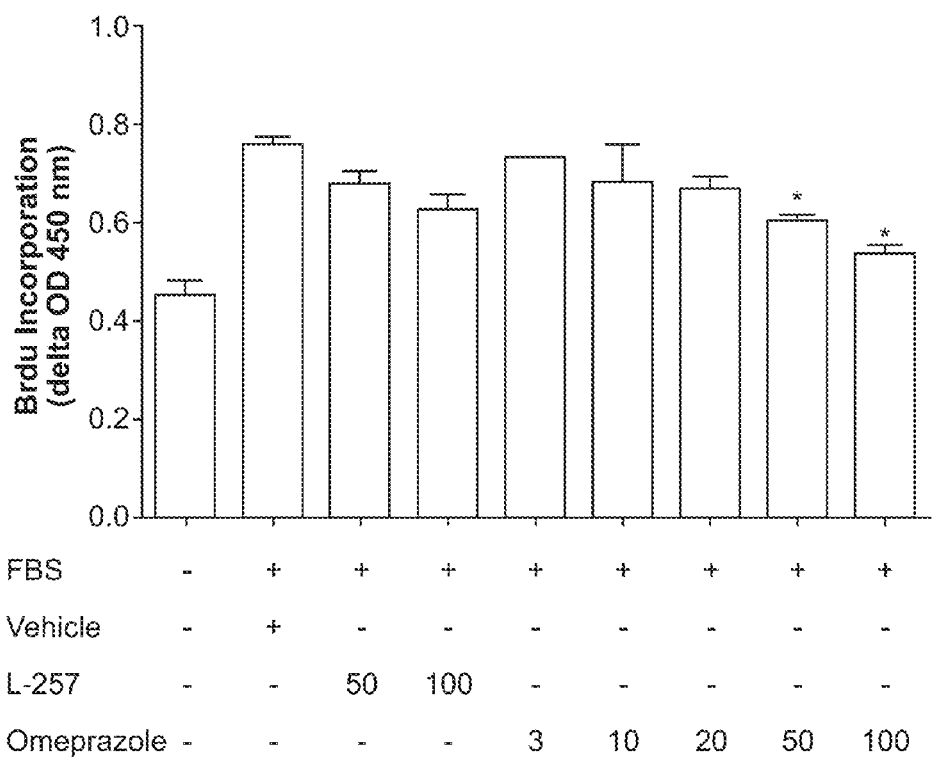
FIG. 24

DIMETHYLARGININE DIMETHYLAMINOHYDROLASE INHIBITORS AND METHODS OF USE THEREOF

CROSS-REFERENCE

This application claims the benefit of U.S. Provisional Patent Application Nos. 61/598,758, filed Feb. 14, 2012, 61/645,383, filed May 10, 2012, and 61/701,990, filed Sep. 17, 2012, each of which applications are incorporated herein by reference in their entirety.

INTRODUCTION

Nitric oxide (NO) is a potent signaling molecule that needs to be tightly regulated to maintain metabolic and cardiovascular homeostasis. The nitric oxide synthase (NOS)/dimethylarginine dimethylaminohydrolase (DDAH)/Asymmetric Dimethylarginine (ADMA) pathway is central to this regulation. The small molecule ADMA competitively inhibits NOS, thus lowering NO levels. The majority of ADMA is physiologically metabolized by DDAH, thus maintaining NO levels at physiological concentration. However, under pathophysiological conditions, NO synthesis and/or DDAH activity may be pathologically increased. Such states include sepsis; fibrosis interstitial, e.g., pulmonary fibrosis; migraine headaches; and some inflammatory and autoimmune diseases.

There is a need in the art for compounds that modulate DDAH activity, e.g., compounds that inhibit DDAH enzymatic activity.

LITERATURE

U.S. Pat. No. 8,063,104; Johnson et al. (2011) J. Am. Chem. Soc. 133(5):1553-62; Johnson et al. (2011) J. Am. Chem. Soc. 133(28):10951-9; Kotthaus et al. (2012) J Enzyme Inhib Med. Chem. 27(1):24-8; Kotthaus et al. (2008) Bioorg Med. Chem. 16(24):10205-9; Lluis et al. (2011) *Chem Med Chem* 6:81-88; Wang et al. (2009) Biochemistry 48(36): 8624-35; U.S. Patent Publication No. 2011/0294878; Knipp et al. (2005) J Am Chem. Soc. 127(8):2372-3; Linsky et al. (2011) ACS Med Chem. Lett. 2(8):592-596; Hartzoulakis et al. (2007) Bioorg Med Chem. Lett. 17(14):3953-6.

SUMMARY

The present disclosure provides DDAH inhibitors, and compositions, including pharmaceutical compositions, comprising the inhibitors. DDAH inhibitors of the present disclosure are useful in treating disorders associated with excessive NO production and/or elevated DDAH activity. The present disclosure provides methods of treating disorders associated with excessive NO production and/or elevated DDAH activity, the methods generally involving administering to an individual in need thereof an effective amount of a subject DDAH inhibitor.

The present disclosure provides a pharmaceutical formulation comprising a DDAH inhibitor of the formula:

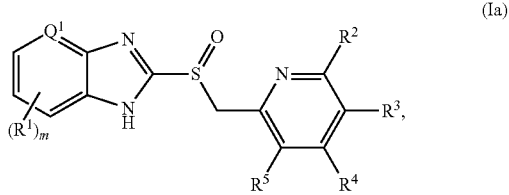

(Ia)

wherein
$Q^1$ is N or CH;
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four; and
a flowable formulation suitable for delivery by inhalation.

The present disclosure provides a pharmaceutical formulation comprising a DDAH inhibitor of the formula:

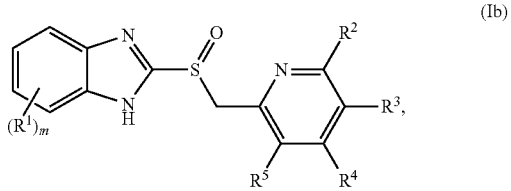

(Ib)

wherein
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four; and
a flowable formulation suitable for delivery by inhalation.

The present disclosure provides a pharmaceutical formulation comprising a DDAH inhibitor of the formula:

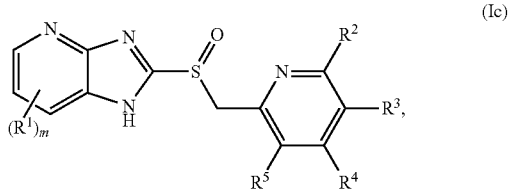

(Ic)

wherein
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^2$, $R^3$, $R^4$, and $R^5$ are independently selected from is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and m is an integer from zero to four; and a flowable formulation suitable for delivery by inhalation.

In some cases, in a subject pharmaceutical formulation, the DDAH inhibitor is selected from:

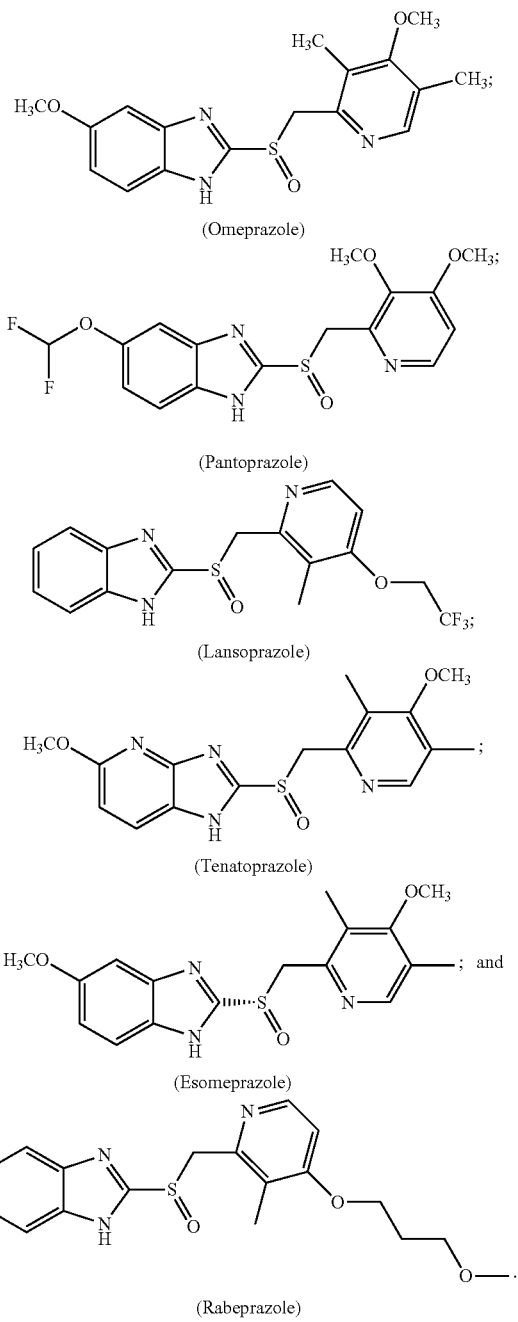

(Omeprazole)

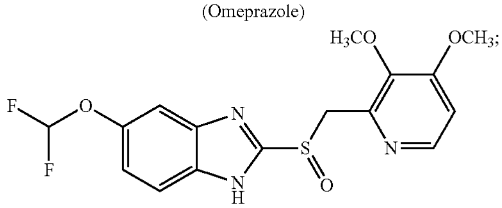

(Pantoprazole)

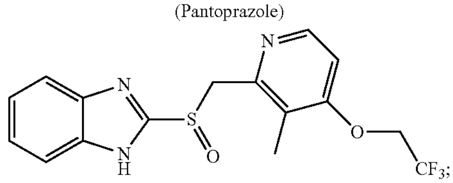

(Lansoprazole)

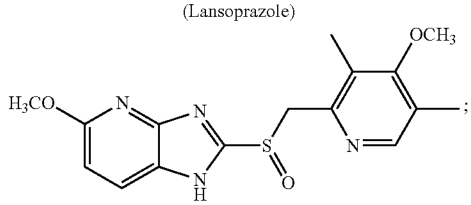

(Tenatoprazole)

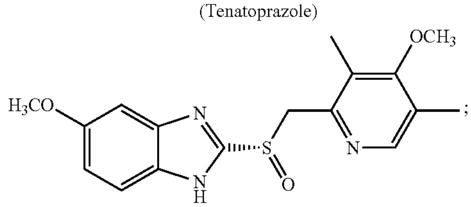

and (Esomeprazole)

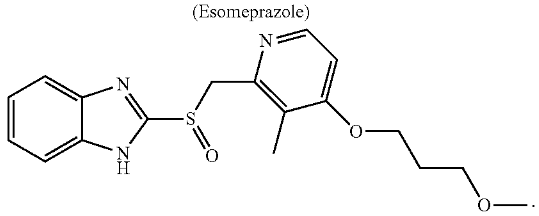

(Rabeprazole)

In any one of a subject pharmaceutical formulation (e.g., a subject pharmaceutical formulation comprising a DDAH inhibitor of Formula Ia, Ib, or Ic), the DDAH inhibitor can be formulated with a fluid carrier and a propellant. In any one of a subject pharmaceutical formulation (e.g., a subject pharmaceutical formulation comprising a DDAH inhibitor of Formula Ia, Ib, or Ic), the DDAH inhibitor can be in a dry powder formulation.

The present disclosure provides a package for use in treating a disorder associated with excessive NO production and/or elevated DDAH activity, where the package comprises a container having therein a subject pharmaceutical formulation (e.g., a subject pharmaceutical formulation comprising a DDAH inhibitor of Formula Ia, Ib, or Ic). In some cases, the package is a metered dose inhaler, and the DDAH inhibitor is formulated with a propellant. In some cases, the package is a dry powder inhaler, and the DDAH inhibitor is formulated in a dry powder formulation. In some cases, the package is a nebulizer, and the DDAH inhibitor is in an aqueous or ethanolic solution.

The present disclosure provides a metered dose inhaler having therein a subject pharmaceutical formulation, wherein the DDAH inhibitor is formulated with a propellant. The present disclosure provides a dry powder inhaler having therein a subject pharmaceutical formulation, wherein the DDAH inhibitor is formulated in a dry powder formulation. The present disclosure provides a nebulizer having therein a subject pharmaceutical formulation, wherein the DDAH inhibitor is in an aqueous or ethanolic solution.

The present disclosure provides an aerosol comprising a pharmaceutically active DDAH inhibitor. In some cases, the DDAH inhibitor is contained within aerosolized particles having a diameter in a range of from about 0.25 μm to about 12 μm. In some cases, the aerosol is in the form of a solution. In some cases, the aerosol is in the form of a suspension. In some cases, the aerosol is in the form of a powder. In some cases, the aerosol is in the form of a semi-solid preparation.

The present disclosure provides a pharmaceutical formulation comprising a dimethylarginine dimethylaminohydrolase (DDAH) inhibitor of the formula:

(III)

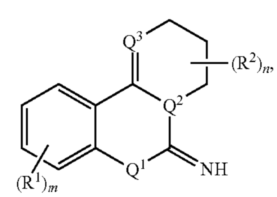

wherein $Q^1$ is S, O, NH or $CH_2$;

$Q^2$ is N or CH;

$Q^3$ is N or CH;

$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^2$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

m is an integer from zero to four; and n is an integer from zero to three; and a flowable formulation suitable for delivery by inhalation.

In some cases, the DDAH inhibitor is:

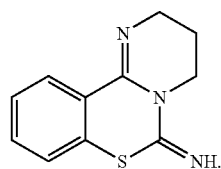 [SMILES: N=C1Sc2ccccc2C2=NCCCN12]

In some cases, the DDAH inhibitor of Formula III is formulated with a fluid carrier and a propellant; or the DDAH inhibitor of Formula III is in a dry powder formulation.

The present disclosure provides a package for use in treating a disorder associated with excessive NO production and/or elevated DDAH activity, the package comprising a container having therein a subject pharmaceutical formulation comprising a DDAH inhibitor of Formula III. In some cases, the package is a metered dose inhaler, and the DDAH inhibitor is formulated with a propellant; or the package is a dry powder inhaler, and the DDAH inhibitor is formulated in a dry powder formulation; or the package is a nebulizer, and the DDAH inhibitor is in an aqueous or ethanolic solution.

The present disclosure provides a pharmaceutical formulation comprising a dimethylarginine dimethylaminohydrolase (DDAH) inhibitor of the formula:

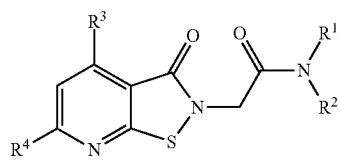
(IIa)

wherein
$R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl;
$R^2$ is selected from hydrogen, alkyl, and substituted alkyl;
$R^3$ and $R^4$ are independently selected from is selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
a pharmaceutically acceptable excipient.

The present disclosure provides a pharmaceutical formulation comprising a dimethylarginine dimethylaminohydrolase (DDAH) inhibitor of the formula:

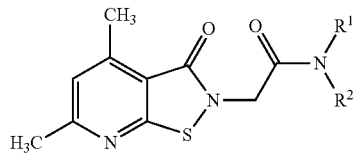
(IIb)

wherein
$R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl;
$R^2$ is selected from hydrogen, alkyl, and substituted alkyl; and
a pharmaceutically acceptable excipient.

In some cases, the DDAH inhibitor is selected from:

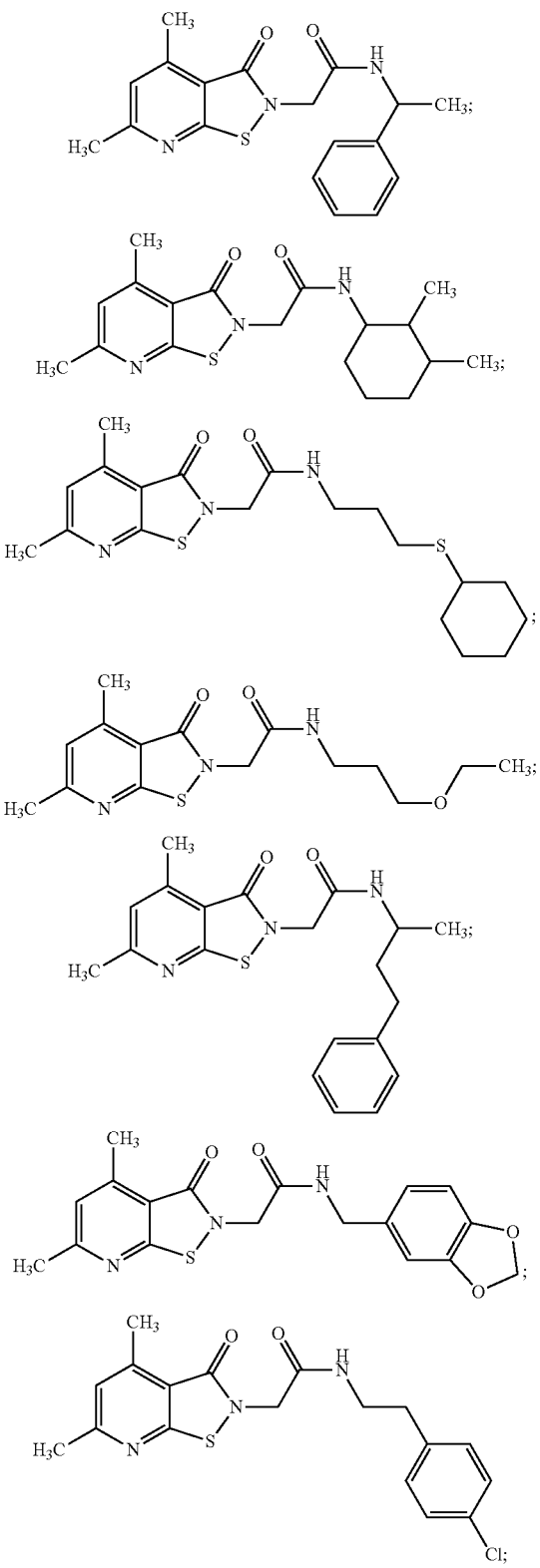

-continued

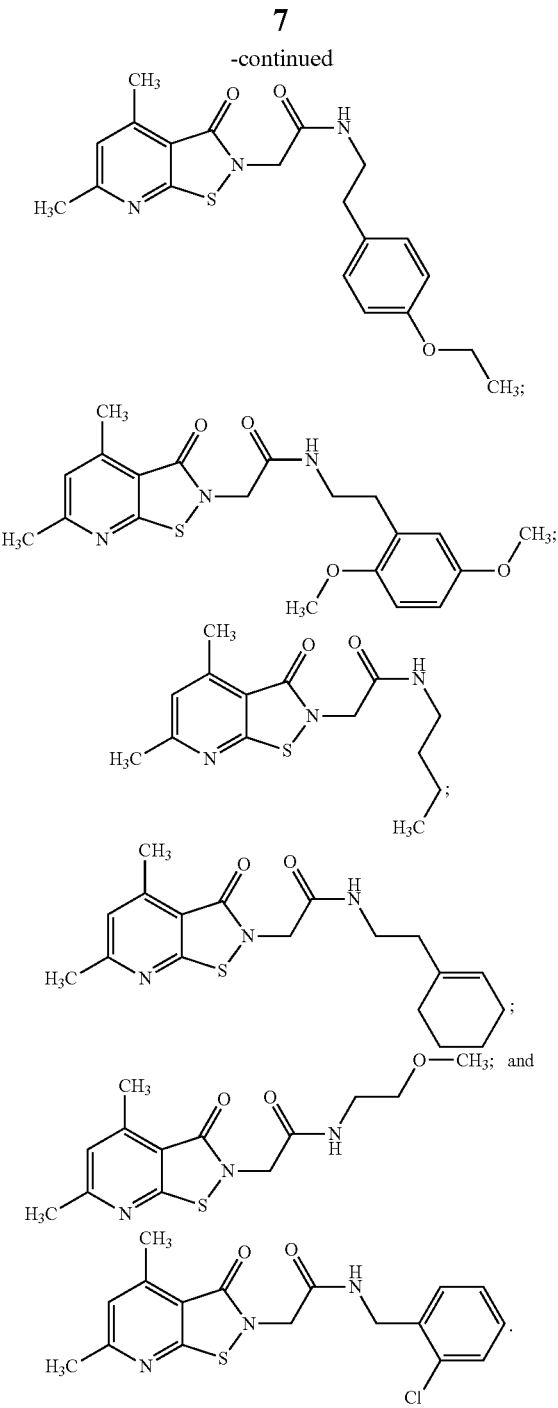

In some cases, in a subject pharmaceutical formulation (e.g., a pharmaceutical formulation comprising a DDAH inhibitor of Formula IIa or Formula IIb, or any of the above-listed specific DDAH inhibitors of Formula IIa or IIb) the DDAH inhibitor is formulated with a fluid carrier and a propellant. In some cases, in a subject pharmaceutical formulation (e.g., a pharmaceutical formulation comprising a DDAH inhibitor of Formula IIa or Formula IIb, or any of the above-listed specific DDAH inhibitors of Formula IIa or IIb) the DDAH inhibitor is in a dry powder formulation.

The present disclosure provides a package for use in treating a disorder associated with excessive NO production and/or elevated DDAH activity, the package comprising a container having therein a subject pharmaceutical formulation (e.g., a pharmaceutical formulation comprising a DDAH inhibitor of Formula IIa or Formula IIb, or any of the above-listed specific DDAH inhibitors of Formula IIa or IIb). In some cases, the package is a metered dose inhaler, and the DDAH inhibitor is formulated with a propellant. In some cases, the package is a dry powder inhaler, and the DDAH inhibitor is formulated in a dry powder formulation. In some cases, the package is a nebulizer, and the DDAH inhibitor is in an aqueous or ethanolic solution.

The present disclosure provides a method of treating an individual suffering from a disorder characterized by excessive NO production and/or elevated DDAH activity, the method comprising administering to the individual an effective amount of a subject pharmaceutical formulation. In some cases (e.g., where the pharmaceutical formulation comprises a DDAH inhibitor of Formula IIa, IIb, a compound of any of Formulas IV-IX, or a compound of Formula X), the formulation is administered by injection. In some cases (e.g., where the pharmaceutical formulation comprises a DDAH inhibitor of Formula IIa, IIb, a compound of any of Formulas IV-IX, or a compound of Formula X), the formulation administered with a carrier in the form of normal saline solution. In some cases (e.g., where the pharmaceutical formulation comprises a DDAH inhibitor of Formula Ia, Ib, Ic, or III, or where the formulation comprises a DDAH inhibitor of Formula IIa, IIb, a compound of any of Formulas IV-IX, or a compound of Formula X), the DDAH inhibitor is administered locally to the airways of the patient. In some cases (e.g., where the pharmaceutical formulation comprises a DDAH inhibitor of Formula Ia, Ib, Ic, or III, or where the formulation comprises a DDAH inhibitor of Formula IIa, IIb, a compound of any of Formulas IV-IX, or a compound of Formula X), the DDAH inhibitor is administered by inhalation. In some cases (e.g., where the pharmaceutical formulation comprises a DDAH inhibitor of Formula Ia, Ib, Ic, or III, or where the formulation comprises a DDAH inhibitor of Formula IIa, IIb, a compound of any of Formulas IV-IX, or a compound of Formula X), the DDAH inhibitor is administered by insufflating an aerosol comprising the DDAH inhibitor. In some cases, the DDAH inhibitor is in a dry powder formulation. In some cases, the DDAH inhibitor is administered using a nebulizer. In some cases, the DDAH inhibitor is in an aqueous or ethanolic solution. In some cases, the individual being treated is a human. In some cases, the individual being treated is a non-human mammal. In some cases, the disease being treated is fibrosis. In some cases, the disease being treated is pulmonary fibrosis, e.g., IPF.

The present disclosure provides an in vitro method of identifying an agent that inhibits enzymatic activity of a DDAH polypeptide, the method comprising: a) contacting the DDAH polypeptide and a DDAH substrate with a test agent; and b) determining the effect, if any, of the test agent on DDAH enzymatic activity, wherein the substrate is asymmetric dimethylarginine, and the determining step is a colorimetric assay for L-citrulline. A test agent that decreases DDAH activity, compare to a control, is an agent that inhibits DDAH activity. An agent that inhibits DDAH activity can be considered a candidate agent for treating a disorder characterized by excessive NO production and/or elevated DDAH activity levels. In some cases, the substrate is ADMA, and said determining step comprises reacting L-citrulline with 2,3-Dimethyl-1-phenyl-3-pyrazolin-5-one and 2,3-butanedione oxime.

BRIEF DESCRIPTION OF THE DRAWINGS

FIG. 15 provides an amino acid sequence of a DDAH polypeptide.

FIG. 23 depicts the effect of a proton pump inhibitor on collagen production by lung fibroblasts from patients with idiopathic pulmonary fibrosis (IPF).

FIG. 24 is a graph showing the effect of PPI on human lung alveolar epithelial cell proliferation.

DEFINITIONS

Figure 1:
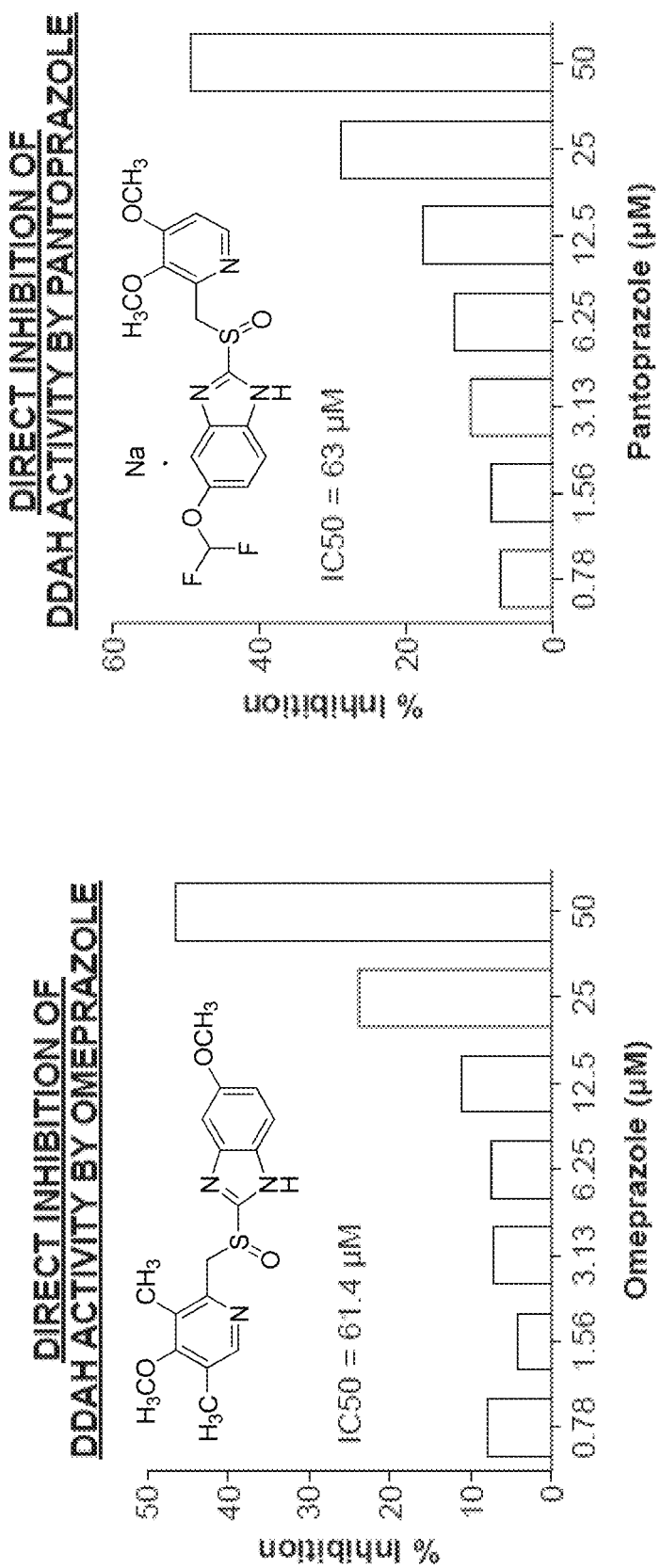
FIG. 1 provides graphs showing inhibition of DDAH activity by various compounds.
Figure 1:
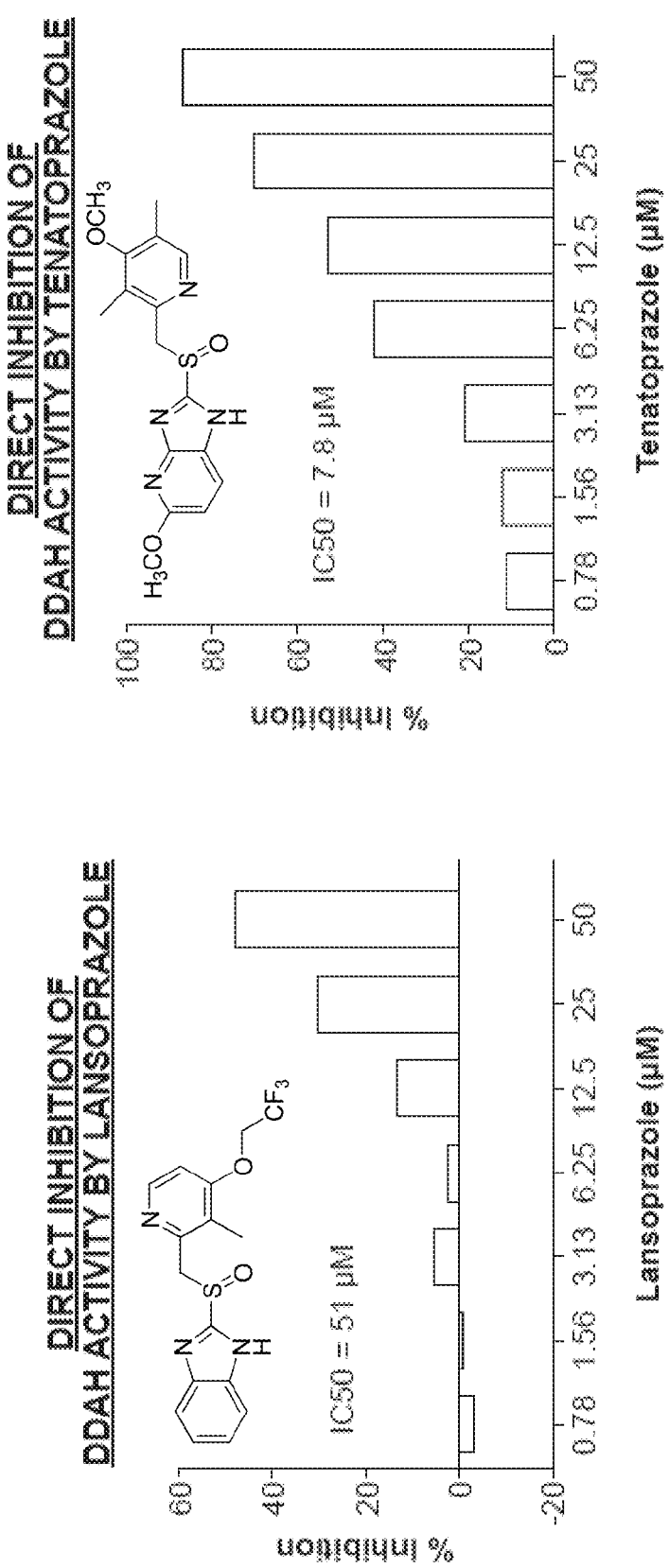

The following terms have the following meanings unless otherwise indicated. Any undefined terms have their art recognized meanings.

"Alkyl" refers to monovalent saturated aliphatic hydrocarbyl groups having from 1 to 10 carbon atoms, e.g., from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3$)($CH_3CH_2$)CH—), t-butyl (($CH_3)_3C$—), n-pentyl ($CH_3CH_2CH_2CH_2CH_2$—), and neopentyl ($(CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups, e.g., having from 1 to 6 carbon atoms or from 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-β-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-5-alkyl, alkylene-S-substituted alkyl, substituted alkylene-5-alkyl and substituted alkylene-5-substituted alkyl wherein alkyl, substituted alkyl, alkylene and substituted alkylene are as defined herein.

"Alkenyl" refers to straight chain or branched hydrocarbyl groups having from 2 to 6 carbon atoms or from 2 to 4 carbon atoms, and having at least 1 site of double bond unsaturatio, e.g., from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms or from 2 to 3 carbon atoms and having at least 1 site of triple bond unsaturation, e.g., from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—.

"Acylamino" refers to the groups —NR$^{20}$C(O)alkyl, —NR$^{20}$C(O)substituted alkyl, N R$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)β-cycloalkyl, —C(O)O-substituted cycloalkyl, —C(O)β-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)β-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiroring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond, e.g., from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiroring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$- substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$— "Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as) $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_2^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal, inhalational, and the like. In some embodiments a subject composition is formulated with an excipient other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

"Pharmaceutically effective amount" and "therapeutically effective amount" refer to the amount of a compound that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

"Fibrosis" or "fibrotic disorder" refers to a pathological condition resulting from an overproduction or aberrant production of fibrous tissue (e.g., fibrous connective tissue) in an organ or tissue, e.g., in a reparative or reactive process. Fibrotic disorders include, but are not limited to, pulmonary fibrosis, including idiopathic pulmonary fibrosis (IPF) and pulmonary fibrosis from a known etiology; liver fibrosis; and renal fibrosis. Other exemplary fibrotic conditions include musculoskeletal fibrosis, cardiac fibrosis, vascular fibrosis, post-surgical adhesions, scleroderma, glaucoma, and skin lesions such as keloids.

The term "treating" or "treatment" as used herein means the treating or treatment of a disease or medical condition in a patient, such as a mammal (e.g., a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a DDAH antagonist" includes a plurality of such antagonists, reference to "a PPI" includes a plurality of proton pump inhibitors, and reference to "the inhalational formulation" includes reference to one or more inhalational formulations and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

DETAILED DESCRIPTION

The present disclosure provides DDAH modulators, e.g., DDAH inhibitors, and compositions, including pharmaceutical compositions (e.g., inhalational formulations) comprising such inhibitors.

Figure 16:
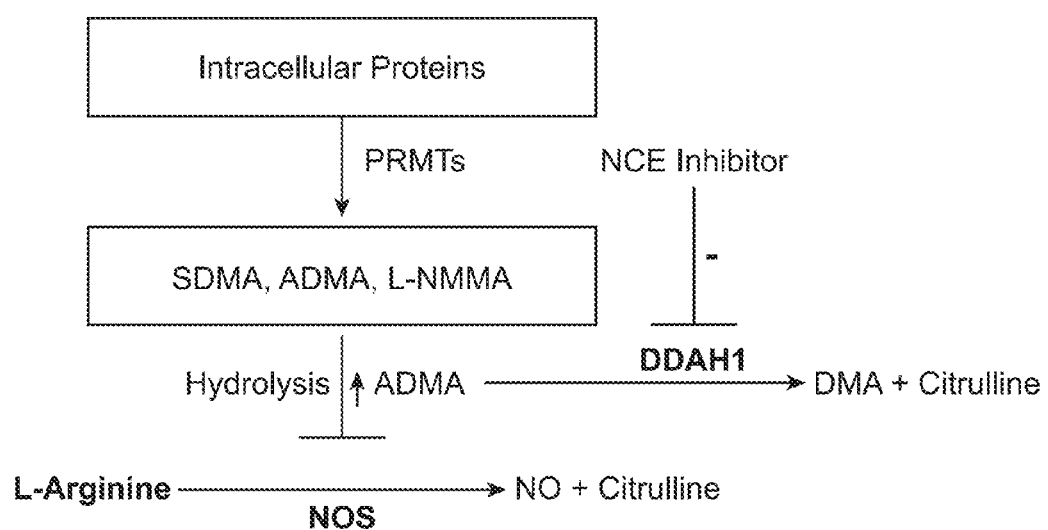
FIG. 16 depicts the NO/ADMA/DDAH pathway. DMA: dimethylamine; ADMA: asymmetric dimethylarginine; SDMA: symmetric dimethyl arginine; L-NMMA: monomethyl arginine; PRMTs: protein arginine methyltransferases; NO: nitric oxide; NCE: new chemical entity.

The NO/ADMA/DDAH pathway is depicted in FIG. 16. ADMA and monomethyl-L-arginine (L-NMMA) are endogenous competitive inhibitors of nitric oxide synthase (NOS). These methylarginines are generated by the methylation of arginine residues on histones and other proteins by a family of enzymes known as Protein Arginine Methyl Transferases (PRMTs). During the hydrolysis of proteins containing methylarginine residues, free ADMA and L-NMMA (monomethyl arginine) are released. The present disclosure provides small molecules and formulation that regulate NO by controlling the activity of DDAH. Pharmacological inhibition of DDAH1 leads to higher ADMA levels and regulation of NO production.

A subject DDAH is useful for treating a patient suffering from a disorder characterized by excessive NO production, and/or elevated DDAH activity. Thus, the present disclosure provides a method of treating a patient suffering from a disorder characterized by excessive NO production, and/or elevated DDAH activity, the method comprising administering to said patient an effective amount of a compound of formulae I-X, or an inhalational formulation comprising such compound. The present disclosure also provides a pharmaceutical composition comprising a compound of the formulae I-X and a pharmaceutically acceptable excipient, wherein the compound is in a formulation suitable for delivery by inhalation.

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

Inhalational Formulations

The present disclosure provides pharmaceutical compositions comprising a DDAH inhibitor and a pharmaceutically acceptable excipient, in a formulation suitable for administration by inhalation, e.g., inhalation into the lungs. The present disclosure provides a pharmaceutical composition comprising a compound of any one of Formulae I-X, below, and a pharmaceutically acceptable excipient, where the compound is in a formulation suitable for delivery by inhalation.

For therapeutic use in diseases characterized by excessive NO production and/or elevated DDAH activity, local delivery to the lung can be carried out. Delivery by inhalation or insufflating aerosols provide high level concentrations of drug compared to the concentration absorbed systemically.

Administration by inhalation can provide for smaller doses delivered locally to the specific cells in the lung which are most in need of treatment. By delivering smaller doses, any adverse side effects are eliminated or substantially reduced. By delivering directly to the cells which are most in need of treatment, the effect of the treatment will be realized more quickly.

The compound of Formulae I-X may be administered to the afflicted patient by means of a pharmaceutical delivery system for the inhalation route. The compounds may be formulated in a form suitable for administration by inhalation. The pharmaceutical delivery system is one that is suitable for respiratory therapy by administration via inhalation of a compound of any one of Formulae I-X thereof to lung tissue, e.g., the bronchi.

The pharmaceutical compositions of the embodiments can be prepared by thoroughly and intimately mixing or blending a compound of any one of Formulae I-X with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

The disclosure provides a system that depends on the power of a compressed gas to expel a compound of any one of Formulae I-X from a container. An aerosol or pressurized package can be employed for this purpose. As used herein, the term "aerosol" is used in its conventional sense as referring to very fine liquid or solid particles carries by a propellant gas under pressure to a site of therapeutic application. When a pharmaceutical aerosol is employed in this invention, the aerosol contains the therapeutically active compound, which can be dissolved, suspended, or emulsified in a mixture of a fluid carrier and a propellant. The aerosol can be in the form of a solution, suspension, emulsion, powder, or semi-solid preparation. Aerosols employed in the present embodiments are intended for administration as fine, solid particles or as liquid mists via the respiratory tract of a patient. Various types of propellants known to one of skill in the art can be utilized. Examples of suitable propellants include, but are not limited to, hydrocarbons or other suitable gas. In the case of the pressurized aerosol, the dosage unit may be determined by providing a value to deliver a metered amount.

In certain embodiments, the pharmaceutical compositions are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In certain embodiments, the pharmaceutical composition comprising the active agent (e.g., a compound of any one of Formulae I-X) is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 µm. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 and WO 97/12687.

A representative pharmaceutical composition for use in a nebulizer inhaler comprises an isotonic aqueous solution comprising from about 0.05 µg/mL to about 10 mg/mL of a compound of any one of Formulae I-X or a pharmaceutically acceptable salt or solvate or stereoisomer thereof.

In certain embodiments, the pharmaceutical composition comprising the active agent is administered by inhalation using a dry powder inhaler. Such dry powder inhalers typically administer the active agent as a free-flowing powder that is dispersed in a patient's air-stream during inspiration. In order to achieve a free-flowing powder, the active agent is typically formulated with a suitable excipient such as lactose or starch.

A representative pharmaceutical composition for use in a dry powder inhaler comprises dry lactose having a particle size between about 1 µm and about 100 µm and micronized particles of a compound of any one of Formulae I-X, or a pharmaceutically acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); Rotahaler (GlaxoSmithKline) (see, e.g., U.S. Pat. No. 4,353,365) and Handihaler (Boehringer Ingelheim). Further examples of suitable DPI devices are described in U.S. Pat. Nos. 5,415,162, 5,239,993, and 5,715,810 and references cited therein.

In certain embodiments, the pharmaceutical composition comprising an active agent (e.g., a compound of any one of Formulae I-X) is administered by inhalation using a metered-dose inhaler. Such metered-dose inhalers typically discharge a measured amount of the active agent or a pharmaceutically acceptable salt thereof using compressed propellant gas. Accordingly, pharmaceutical compositions administered using a metered-dose inhaler can comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs can be used. Additional optional components of HFA formulations include co-solvents, such as ethanol or pentane, and surfactants, such as sorbitan trioleate, oleic acid, lecithin, and glycerin. See, for example, U.S. Pat. No. 5,225,183, EP 0717987 A2, and WO 92/22286.

A representative pharmaceutical composition for use in a metered-dose inhaler comprises from about 0.01% to about 5% by weight of a compound of any one of Formulae I-X, or a pharmaceutically acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. Nos. 6,006,745 and 6,143,277. Alternatively, a suspension formulation can be prepared by spray drying a coating of surfactant on micronized particles of the active agent. See, for example, WO 99/53901 and WO 00/61108.

For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

With respect to each of the patents recited above, applicants point out that these patents cite other publications in intrapulmonary drug delivery and such publications can be referred to for specific methodology, devices and formulations which could be used in connection with the delivery of agonists of the present embodiments. Further, each of the patents are incorporated herein by reference in their entirety for purposes of disclosing formulations, devices, packaging and methodology for the delivery of agonist formulations of the present embodiments.

Any conventional carrier or excipient may be used in the pharmaceutical compositions of the embodiments. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers or excipients include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

DDAH Inhibitors for Inhalational Formulations

A subject pharmaceutical formulation suitable for inhalation comprises a DDAH inhibitor. The following are suitable DDAH inhibitors. In the formulae herein, a formula number is meant to encompass all forms of the formula number. Thus, reference to formula (I) is meant to include compounds of formula (Ia), (Ib), and (Ic).

Formula I

According to one aspect, the embodiments include pharmaceutical compositions formulated for inhalational delivery, which compositions a compound of Formula Ia:

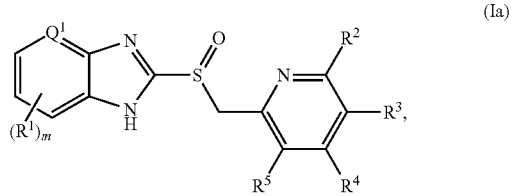

(Ia)

wherein
$Q^1$ is N or CH;
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four;
or a pharmaceutical salt thereof.

According to one aspect, the embodiments include pharmaceutical compositions formulated for inhalational delivery, which compositions include a compound of Formula Ib:

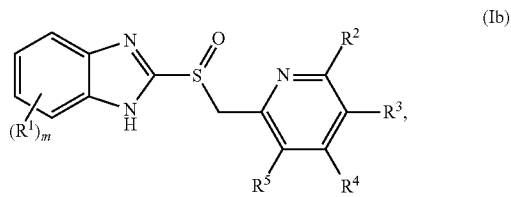

(Ib)

wherein
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four;
or a pharmaceutical salt thereof.

According to one aspect, the embodiments include pharmaceutical compositions formulated for inhalational delivery, which include a compound of Formula Ic:

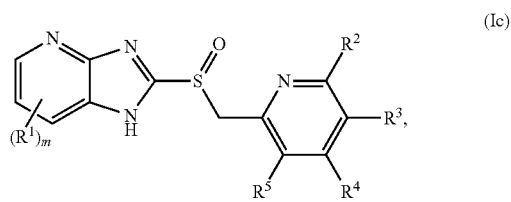

(Ic)

wherein
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four;
or a pharmaceutical salt thereof.

In Formula Ia, $Q^1$ is N or CH. In certain embodiments, $Q^1$ is N. In certain embodiments, $Q^1$ is CH.

In Formula I, $R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, $R^1$ is alkyl or substituted alkyl. In certain embodiments, $R^1$ is hydroxy. In certain embodiments, $R^1$ is alkoxy or substituted alkoxy. In certain embodiments, $R^1$ is alkoxy. For example, $R^1$ may be a $C_1$-$C_6$ alkoxy, such as a $C_1$-$C_3$ alkoxy. In certain embodiments, $R^1$ is —$OCH_3$. In certain embodiments, $R^1$ is substituted alkoxy. For example, in embodiments where $R^1$ is a substituted alkoxy, the alkoxy group may be substituted with one or more groups, such as, but not limited to, alkyl, hydroxy, alkoxy, amino, carboxyl, carboxyl ester, cyano, halogen, acyl, aminoacyl, nitro, alkenyl, alkynyl, and the like. The substituents on the substituted alkoxy may in turn be substituted with one or more groups as described above. In certain embodiments, the alkoxy is substituted with one or more halogen groups (e.g., F, Cl, Br, I). In certain embodiments, the alkoxy is substituted with one or more fluoro groups. In certain embodiments, $R^1$ is —$OCHF_2$. In certain embodiments, $R^1$ is amino or substituted amino. In certain embodiments, $R^1$ is carboxyl or carboxyl ester. In certain embodiments, $R^1$ is cyano, halogen, acyl, aminoacyl, or nitro. In certain embodiments, $R^1$ is alkenyl, substituted alkenyl, alkynyl, or substituted alkynyl.

In Formula I, m is an integer from zero to four. In certain embodiments, m is zero. In certain embodiments, m is one. In certain embodiments, m is two. In certain embodiments, m is three. In certain embodiments, m is four.

In Formula I, $R^2$, $R^3$, $R^4$, and $R^5$ are independently selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, $R^2$ is hydrogen. In certain embodiments, $R^2$ is alkyl or substituted alkyl. In certain embodiments, $R^2$ is hydroxy, alkoxy, or substituted alkoxy. In certain embodiments, $R^2$ is amino or substituted amino. In certain embodiments, $R^2$ is carboxyl or carboxyl ester. In certain embodiments, $R^2$ is cyano, halogen, acyl, aminoacyl, or nitro. In certain embodiments, $R^2$ is alkenyl, substituted alkenyl, alkynyl, or substituted alkynyl.

In certain embodiments, $R^3$ is hydrogen. In certain embodiments, $R^3$ is alkyl or substituted alkyl. In certain embodiments, $R^3$ is alkyl. For example, $R^3$ may be a $C_1$-$C_6$ alkyl, such as a $C_1$-$C_3$ alkyl. In certain embodiments, $R^3$ is methyl. In certain embodiments, $R^3$ is hydroxy, alkoxy, or substituted alkoxy. In certain embodiments, $R^3$ is amino or substituted amino. In certain embodiments, $R^3$ is carboxyl or carboxyl ester. In certain embodiments, $R^3$ is cyano, halogen, acyl, aminoacyl, or nitro. In certain embodiments, $R^3$ is alkenyl, substituted alkenyl, alkynyl, or substituted alkynyl.

In certain embodiments, $R^4$ is hydrogen. In certain embodiments, $R^4$ is alkyl or substituted alkyl. In certain embodiments, $R^4$ is hydroxy, alkoxy, or substituted alkoxy. In certain embodiments, $R^4$ is alkoxy. For example, $R^4$ may be a $C_1$-$C_6$ alkoxy, such as a $C_1$-$C_3$ alkoxy. In certain embodiments, $R^4$ is —$OCH_3$. In certain embodiments, $R^4$ is substituted alkoxy. For example, in embodiments where $R^4$ is a substituted alkoxy, the alkoxy group may be substituted with one or more groups, such as, but not limited to, alkyl, hydroxy, alkoxy, amino, carboxyl, carboxyl ester, cyano, halogen, acyl, aminoacyl, nitro, alkenyl, alkynyl, and the like. The substituents on the substituted alkoxy may in turn be substituted with one or more groups as described above. In certain embodiments, the alkoxy is substituted with one or more halogen groups (e.g., F, Cl, Br, I). In certain embodiments, the alkoxy is substituted with one or more fluoro groups. In certain embodiments, $R^4$ is —$OCH_2CF_3$. In certain embodiments, the alkoxy is substituted with an alkoxy group, such as a $C_1$-$C_6$ alkoxy, or a $C_1$-$C_3$ alkoxy. In certain embodiments, $R^4$ is —$O(CH_2)_3OCH_3$. In certain embodiments, $R^4$ is amino or substituted amino. In certain embodiments, $R^4$ is carboxyl or carboxyl ester. In certain embodiments, $R^4$ is cyano, halogen, acyl, aminoacyl, or nitro. In certain embodiments, $R^4$ is alkenyl, substituted alkenyl, alkynyl, or substituted alkynyl.

In certain embodiments, $R^5$ is hydrogen. In certain embodiments, $R^5$ is alkyl or substituted alkyl. In certain embodiments, $R^5$ is alkyl. For example, $R^5$ may be a $C_1$-$C_6$ alkyl, such as a $C_1$-$C_3$ alkyl. In certain embodiments, $R^5$ is methyl. In certain embodiments, $R^5$ is hydroxy, alkoxy, or substituted alkoxy. In certain embodiments, $R^5$ is alkoxy. For example, $R^5$ may be a $C_1$-$C_6$ alkoxy, such as a $C_1$-$C_3$ alkoxy. In certain embodiments, $R^5$ is —$OCH_3$. In certain embodiments, $R^5$ is amino or substituted amino. In certain embodiments, $R^5$ is carboxyl or carboxyl ester. In certain embodiments, $R^5$ is cyano, halogen, acyl, aminoacyl, or nitro. In certain embodiments, $R^5$ is alkenyl, substituted alkenyl, alkynyl, or substituted alkynyl.

Particular compounds of interest, and salts or solvates or stereoisomers thereof for formulation for inhalational delivery according to the emb

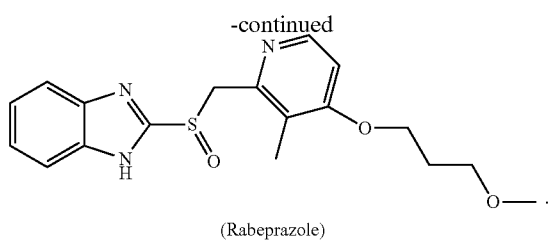

(Rabeprazole)

In some embodiments, one or more of omeprazole, pantoprazole, lansoprazole, tenatoprazole, esomeraprazole, and rabeprazole is specifically excluded.

Formula II

According to one aspect, the present disclosure provides a compound of Formula IIa:

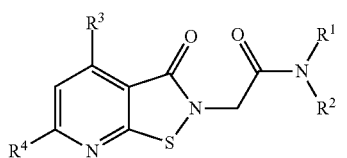
(IIa)

wherein
$R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl;
$R^2$ is selected from hydrogen, alkyl, and substituted alkyl;
$R^3$ and $R^4$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
or a pharmaceutical salt thereof.

According to one aspect, the embodiments include pharmaceutical compositions, which include a compound of Formula IIb:

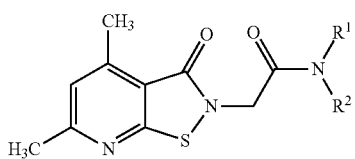
(IIb)

wherein
$R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl;
$R^2$ is selected from hydrogen, alkyl, and substituted alkyl;
or a pharmaceutical salt thereof.

In Formula IIa, $R^3$ and $R^4$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, $R^3$ is hydrogen. In certain embodiments, $R^3$ is alkyl or substituted alkyl. In certain embodiments, $R^3$ is alkyl. For example, $R^3$ may be a $C_1$-$C_6$ alkyl, such as a $C_1$-$C_3$ alkyl. In certain embodiments, $R^3$ is methyl. In certain embodiments, $R^3$ is hydroxy, alkoxy, or substituted alkoxy. In certain embodiments, $R^3$ is amino or substituted amino. In certain embodiments, $R^3$ is carboxyl or carboxyl ester. In certain embodiments, $R^3$ is cyano, halogen, acyl, aminoacyl, or nitro. In certain embodiments, $R^3$ is alkenyl, substituted alkenyl, alkynyl, or substituted alkynyl.

In certain embodiments, $R^4$ is hydrogen. In certain embodiments, $R^4$ is alkyl or substituted alkyl. In certain embodiments, $R^4$ is alkyl. For example, $R^4$ may be a $C_1$-$C_6$ alkyl, such as a $C_1$-$C_3$ alkyl. In certain embodiments, $R^4$ is methyl. In certain embodiments, $R^4$ is hydroxy, alkoxy, or substituted alkoxy. In certain embodiments, $R^4$ is amino or substituted amino. In certain embodiments, $R^4$ is carboxyl or carboxyl ester. In certain embodiments, $R^4$ is cyano, halogen, acyl, aminoacyl, or nitro. In certain embodiments, $R^4$ is alkenyl, substituted alkenyl, alkynyl, or substituted alkynyl.

In the formulae herein, a formula number is meant to encompass all forms of the formula number. Thus, reference to formula (II) is meant to include compounds of formula (IIa) and (IIb). In Formula II, $R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl.

In certain embodiments, $R^1$ is hydrogen. In certain embodiments, $R^1$ is alkyl or substituted alkyl. In certain embodiments, $R^1$ is alkyl. For example, $R^1$ may be a $C_1$-$C_6$ alkyl, such as a $C_1$-$C_3$ alkyl. In certain embodiments, $R^1$ is substituted alkyl. For example, in embodiments where $R^1$ is a substituted alkyl, the alkyl group may be substituted with one or more groups, such as, but not limited to, alkyl, hydroxy, alkoxy, amino, carboxyl, carboxyl ester, cyano, halogen, thio, acyl, aminoacyl, nitro, alkenyl, alkynyl, cycloalkyl, heterocycloalkyl, aryl, heteroaryl, and the like. In certain embodiments, the alkyl is substituted with an alkyl group, such as a $C_1$-$C_6$ alkyl, or a $C_1$-$C_3$ alkyl. In certain embodiments, the alkyl is substituted with an alkoxy group, such as a $C_1$-$C_6$ alkoxy, or a $C_1$-$C_3$ alkoxy. In certain embodiments, the alkyl group is substituted with a cycloalkyl group, such as a saturated or unsaturated cycloalkyl group. In certain embodiments, the alkyl group is substituted with an aryl. Combinations of the above substituents may also be included. The substituents on the substituted alkyl may in turn be substituted with one or more groups as described above, such as, but not limited to, alkyl, hydroxy, alkoxy, amino, carboxyl, carboxyl ester, cyano, halogen (e.g., F, Cl, Br, I), thio, acyl, aminoacyl, nitro, alkenyl, alkynyl, cycloalkyl, heterocycloalkyl, aryl, heteroaryl, and the like. In certain embodiments, $R^1$ is alkoxy or substituted alkoxy. In certain embodiments, $R^1$ is cycloalkyl or substituted cycloalkyl. In certain embodiments, $R^1$ is cycloalkyl, such as $C_3$-$C_{10}$ cycloalkyl, or a $C_3$-$C_6$ cycloalkyl. In certain embodiments, $R^1$ is cyclohexyl. In certain embodiments, $R^1$ is a substituted cycloalkyl, where the cycloalkyl group is substituted with one or more groups as described above, such as, but not limited to, alkyl, hydroxy, alkoxy, amino, carboxyl, carboxyl ester, cyano, halogen (e.g., F, Cl, Br, I), thio, acyl, aminoacyl, nitro, alkenyl, alkynyl, cycloalkyl, heterocycloalkyl, aryl, heteroaryl, and the like. For example, the cycloalkyl group may be substituted with one or more alkyl groups, such as a $C_1$-$C_6$ alkyl, or a $C_1$-$C_3$ alkyl (e.g., methyl). In certain embodiments, $R^1$ is aryl or substituted aryl. In certain embodiments, $R^1$ is heterocyclyl or substituted heterocyclyl. In certain embodiments, $R^1$ is selected from the following:

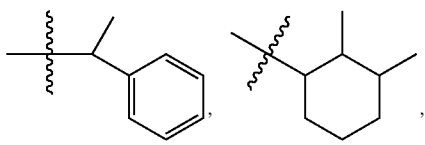

31
-continued

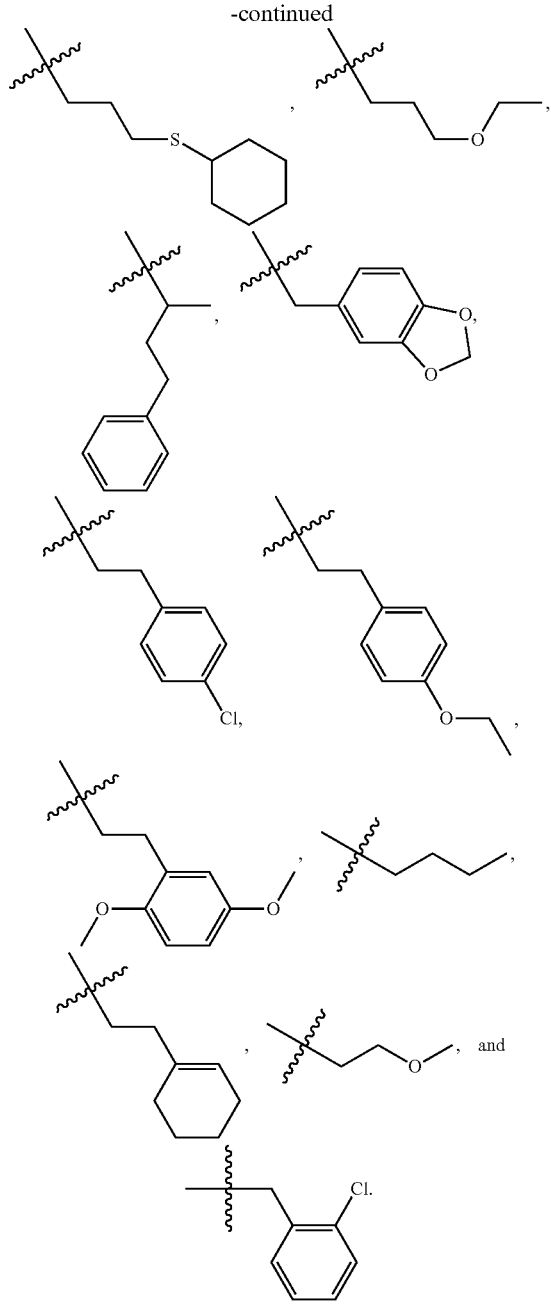

In Formula II, R² is selected from hydrogen, alkyl, and substituted alkyl. In certain embodiments, $R^2$ is hydrogen. In certain embodiments, $R^2$ is selected from alkyl. In certain embodiments, $R^2$ is substituted alkyl.

Particular compounds of interest, and salts or solvates or stereoisomers thereof for formulation according to the embodiments, include:

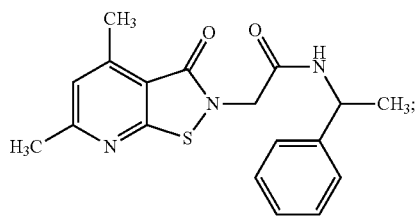

32
-continued

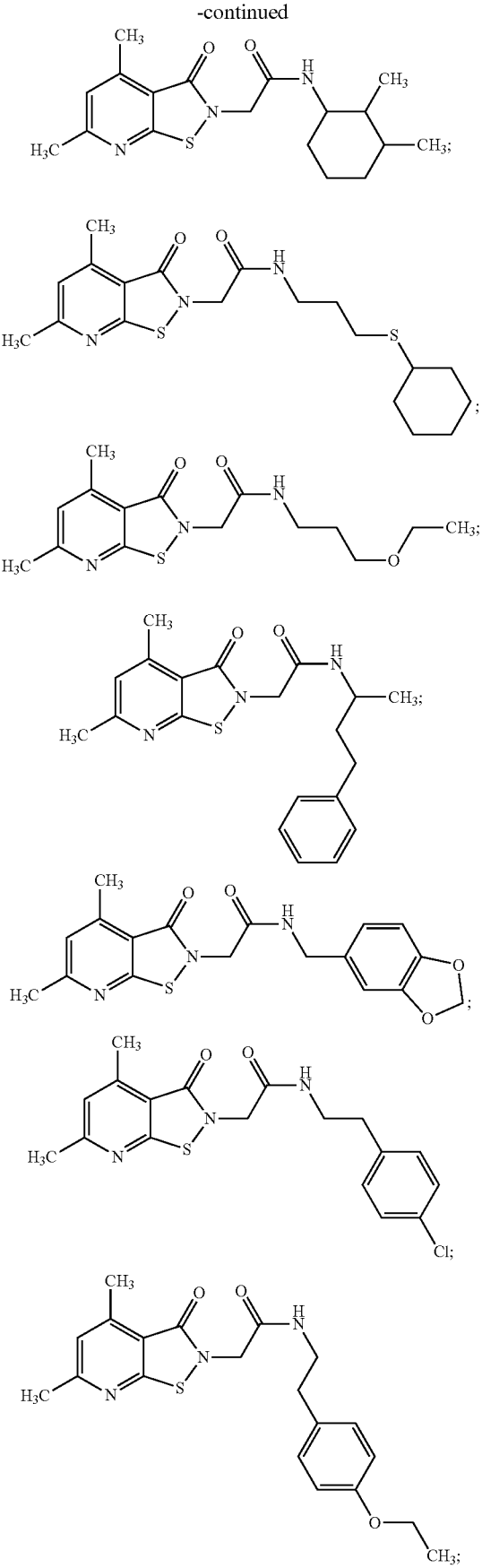

-continued

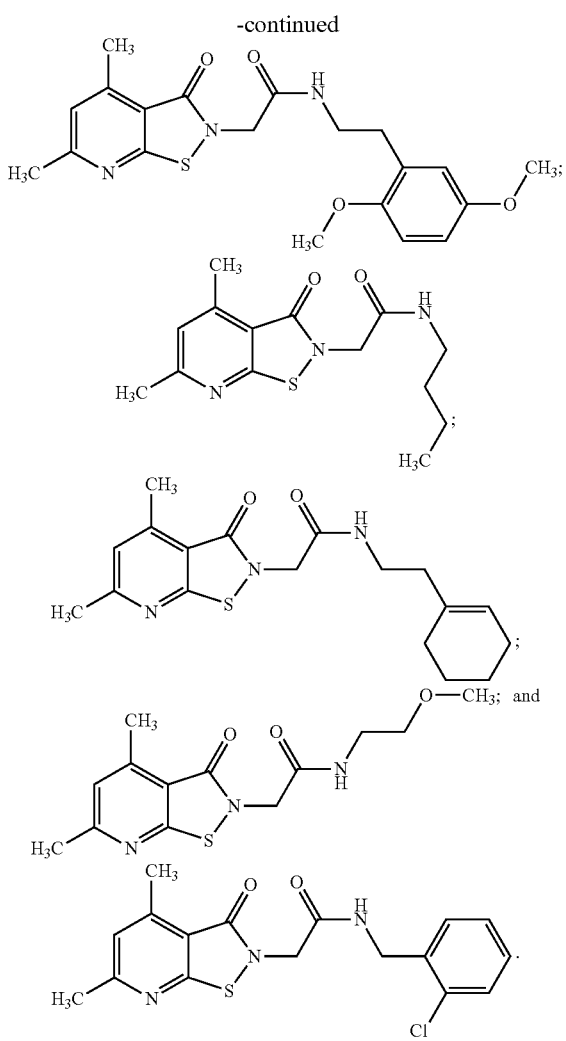

Formula III

According to one aspect, the embodiments include pharmaceutical compositions formulated for inhalational delivery, which compositions include a compound of Formula III:

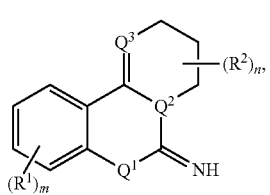

(III)

wherein
Q$^1$ is S, O, NH or CH$_2$;
Q$^2$ is N or CH;
Q$^3$ is N or CH;
R$^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
R$^2$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
m is an integer from zero to four; and
n is an integer from zero to three;
or a pharmaceutical salt thereof.

In Formula III, Q$^1$ is S, O, NH or CH$_2$. In certain embodiments, Q$^1$ is S In certain embodiments, Q$^1$ is O. In certain embodiments, Q$^1$ is NH. In certain embodiments, Q$^1$ is CH$_2$ In Formula III, Q$^2$ is N or CH. In certain embodiments, Q$^2$ is N. In certain embodiments, Q$^2$ is CH.

In Formula III, Q$^3$ is N or CH. In certain embodiments, Q$^3$ is N. In certain embodiments, Q$^3$ is CH.

In Formula III, R$^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, R$^1$ is alkyl or substituted alkyl. In certain embodiments, R$^1$ is hydroxy, alkoxy, or substituted alkoxy. In certain embodiments, R$^1$ is amino, substituted amino, carboxyl, or carboxyl ester. In certain embodiments, R$^1$ is cyano, halogen, acyl, aminoacyl, nitro, alkenyl, substituted alkenyl, alkynyl, or substituted alkynyl.

In Formula III, R$^2$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, R$^2$ is alkyl or substituted alkyl. In certain embodiments, R$^2$ is hydroxy, alkoxy, or substituted alkoxy. In certain embodiments, R$^2$ is amino, substituted amino, carboxyl, or carboxyl ester. In certain embodiments, R$^2$ is cyano, halogen, acyl, aminoacyl, nitro, alkenyl, substituted alkenyl, alkynyl, or substituted alkynyl.

In Formula III, m is an integer from zero to four. In certain embodiments, m is zero. In certain embodiments, m is one. In certain embodiments, m is two. In certain embodiments, m is three. In certain embodiments, m is four.

In Formula III, n is an integer from zero to three. In certain embodiments, n is zero. In certain embodiments, n is one. In certain embodiments, n is two. In certain embodiments, n is three.

A particular compound of interest, and salts or solvates or stereoisomers thereof for formulation according to the embodiments, is:

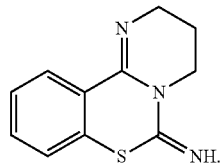

Formula IV-IX

Particular compounds of interest, and salts or solvates or stereoisomers thereof for formulation according to the embodiments, include:

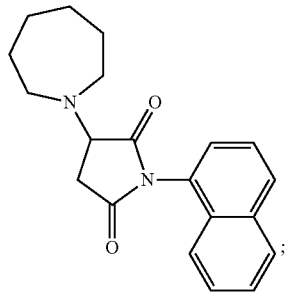

(IV)

-continued

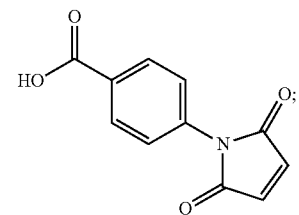
(V)

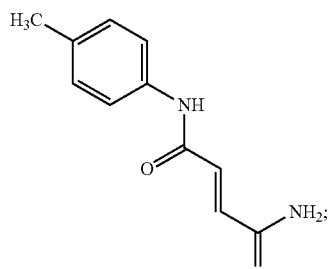
(VI)

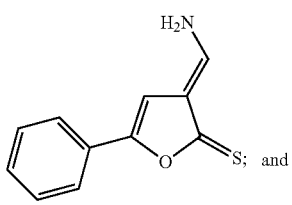
(VII)

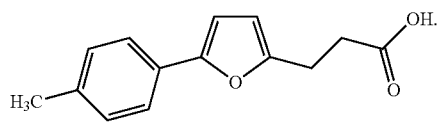
(VIII)

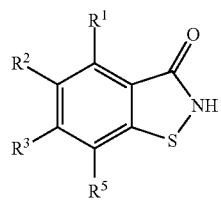
(IX)

Formula X

In the formulae herein, a formula number is meant to encompass all forms of the formula number. Thus, reference to formula (X) is meant to include compounds of formula (Xa) and (Xb).

According to one aspect, the present disclosure provides a pharmaceutical formulation that includes a compound of Formula Xa:

(Xa)

wherein $R^1$, $R^2$ and $R^3$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^4$ is selected from hydrogen, alkyl, substituted alkyl, alkoxy, substituted alkoxy, cycloalkyl, substituted cycloalkyl, aryl, substituted aryl, heterocyclyl, and substituted heterocyclyl; and $Q^1$ is N or $CR^5$, where $R^5$, if present, is selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and a flowable formulation suitable for delivery by inhalation.

According to one aspect, the embodiments include pharmaceutical formulations that include a compound of Formula Xb:

(Xb)

wherein $R^1$, $R^2$, $R^3$ and $R^5$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and a flowable formulation suitable for delivery by inhalation.

In Formula X, $R^1$, $R^2$ and $R^3$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, $R^1$ is hydrogen. In certain embodiments, $R^1$ is alkyl or substituted alkyl. In certain embodiments, $R^1$ is hydroxy, alkoxy, or substituted alkoxy. In certain embodiments, $R^1$ is amino or substituted amino. In certain embodiments, $R^1$ is carboxyl or carboxyl ester. In certain embodiments, $R^1$ is cyano, halogen, acyl, aminoacyl, or nitro. In certain embodiments, $R^1$ is alkenyl, substituted alkenyl, alkynyl, or substituted alkynyl. In certain embodiments, $R^1$ is alkyl, such as a $C_1$-$C_6$ alkyl, or a $C_1$-$C_3$ alkyl. In certain embodiments, $R^1$ is methyl.

In certain embodiments, $R^2$ is hydrogen. In certain embodiments, $R^2$ is alkyl or substituted alkyl. In certain embodiments, $R^2$ is hydroxy, alkoxy, or substituted alkoxy. In certain embodiments, $R^2$ is amino or substituted amino. In certain embodiments, $R^2$ is carboxyl or carboxyl ester. In certain embodiments, $R^2$ is cyano, halogen, acyl, aminoacyl, or nitro. In certain embodiments, $R^2$ is alkenyl, substituted alkenyl, alkynyl, or substituted alkynyl. In certain embodiments, $R^2$ is alkyl, such as a $C_1$-$C_6$ alkyl, or a $C_1$-$C_3$ alkyl. In certain embodiments, $R^2$ is methyl.

In certain embodiments, $R^3$ is hydrogen. In certain embodiments, $R^3$ is alkyl or substituted alkyl. In certain embodiments, $R^3$ is hydroxy, alkoxy, or substituted alkoxy. In certain embodiments, $R^3$ is amino or substituted amino. In certain embodiments, $R^3$ is carboxyl or carboxyl ester. In certain embodiments, $R^3$ is cyano, halogen, acyl, aminoacyl, or nitro. In certain embodiments, $R^3$ is alkenyl, substituted alkenyl, alkynyl, or substituted alkynyl. In certain embodiments, $R^3$ is alkyl, such as a $C_1$-$C_6$ alkyl, or a $C_1$-$C_3$ alkyl. In certain embodiments, $R^3$ is methyl.

In Formula X, $R^4$ is selected from hydrogen, alkyl, substituted alkyl, alkoxy, substituted alkoxy, cycloalkyl, substituted cycloalkyl, aryl, substituted aryl, heterocyclyl, and substituted heterocyclyl.

In certain embodiments, $R^4$ is hydrogen. In certain embodiments, $R^4$ is alkyl or substituted alkyl. In certain embodiments, $R^4$ is alkoxy or substituted alkoxy. In certain embodiments, $R^4$ is cycloalkyl or substituted cycloalkyl. In certain embodiments, $R^4$ is aryl or substituted aryl. In certain embodiments, $R^4$ is heterocyclyl or substituted heterocyclyl.

In Formula X, $R^5$, if present, is selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, $R^5$ is hydrogen. In certain embodiments, $R^5$ is alkyl or substituted alkyl. In certain embodiments, $R^5$ is hydroxy, alkoxy, or substituted alkoxy. In certain embodiments, $R^5$ is amino or substituted amino. In certain embodiments, $R^5$ is carboxyl or carboxyl ester. In certain embodiments, $R^5$ is cyano, halogen, acyl, aminoacyl, or nitro. In certain embodiments, $R^5$ is alkenyl, substituted alkenyl, alkynyl, or substituted alkynyl. In certain embodiments, $R^5$ is alkyl, such as a $C_1$-$C_6$ alkyl, or a $C_1$-$C_3$ alkyl. In certain embodiments, $R^5$ is methyl.

Particular compounds of interest, and salts or solvates or stereoisomers thereof for formulation according to the embodiments, include:

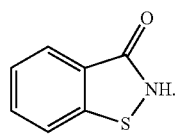

benzo[d]isothiazol-3(2H)-one

DDAH Inhibitors

The present disclosure provides DDAH inhibitors, as well as compositions, including pharmaceutical compositions, comprising a subject DDAH inhibitor.

In some embodiments, a DDAH inhibitor has a half-maximal inhibitor concentration of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM from about 10 µM to about 25 µM, from about 25 µM to about 50 µM, from about 50 µM to about 75 µM, from about 75 µM to about 100 µM from about 100 µM to about 250 µM from about 250 µM to about 500 µM, or from about 500 µM to about 1 mM.

In some embodiments, a DDAH inhibitor inhibits enzymatic activity of a DDAH polypeptide by at least about 10%, at least about 15%, at least about 20%, at least about 25%, at least about 30%, at least about 40%, at least about 50%, or more than 50%, compared to the activity of the DDAH polypeptide in the absence of the inhibitor.

In some cases, a DDAH inhibitor is selective, e.g., the DDAH inhibitor inhibits DDAH enzymatic activity, but does not substantially inhibit enzymes other than DDAH.

In the formulae herein, a formula number is meant to encompass all forms of the formula number. Thus, reference to formula (II) is meant to include compounds of formula (IIa) and (IIb).

Formula II

According to one aspect, the present disclosure provides a compound of Formula IIa:

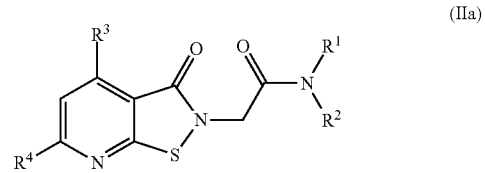

(IIa)

wherein
$R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl;
$R^2$ is selected from hydrogen, alkyl, and substituted alkyl;
$R^3$ and $R^4$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
or a pharmaceutical salt thereof.

According to one aspect, the embodiments include pharmaceutical compositions, which comprise a compound of Formula IIb:

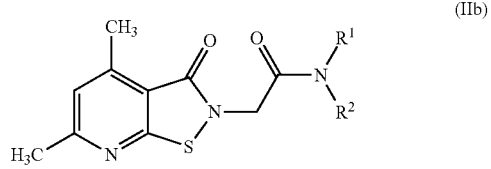

(IIb)

wherein
$R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl;
$R^2$ is selected from hydrogen, alkyl, and substituted alkyl;
or a pharmaceutical salt thereof.

In Formula IIa, $R^3$ and $R^4$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, $R^3$ is hydrogen. In certain embodiments, $R^3$ is alkyl or substituted alkyl. In certain embodiments, $R^3$ is alkyl. For example, $R^3$ may be a $C_1$-$C_6$ alkyl, such as a $C_1$-$C_3$ alkyl. In certain embodiments, $R^3$ is methyl. In certain embodiments, $R^3$ is hydroxy, alkoxy, or substituted alkoxy. In certain embodiments, $R^3$ is amino or substituted amino. In certain embodiments, $R^3$ is carboxyl or carboxyl ester. In certain embodiments, $R^3$ is cyano, halogen, acyl, aminoacyl, or nitro. In certain embodiments, $R^3$ is alkenyl, substituted alkenyl, alkynyl, or substituted alkynyl.

In certain embodiments, $R^4$ is hydrogen. In certain embodiments, $R^4$ is alkyl or substituted alkyl. In certain embodiments, $R^4$ is alkyl. For example, $R^4$ may be a $C_1$-$C_6$ alkyl, such as a $C_1$-$C_3$ alkyl. In certain embodiments, $R^4$ is methyl. In certain embodiments, $R^4$ is hydroxy, alkoxy, or substituted alkoxy. In certain embodiments, $R^4$ is amino or substituted amino. In certain embodiments, $R^4$ is carboxyl or carboxyl ester. In certain embodiments, $R^4$ is cyano, halogen, acyl, aminoacyl, or nitro. In certain embodiments, $R^4$ is alkenyl, substituted alkenyl, alkynyl, or substituted alkynyl.

In Formula II, $R^1$ is selected from hydrogen, alkyl, substituted alkyl, alkoxy, substituted alkoxy, cycloalkyl, substituted cycloalkyl, aryl, substituted aryl, heterocyclyl, and substituted heterocyclyl.

In certain embodiments, $R^1$ is hydrogen. In certain embodiments, $R^1$ is alkyl or substituted alkyl. In certain embodiments, $R^1$ is alkyl. For example, $R^1$ may be a $C_1$-$C_6$ alkyl, such as a $C_1$-$C_3$ alkyl. In certain embodiments, $R^1$ is substituted alkyl. For example, in embodiments where $R^1$ is a substituted alkyl, the alkyl group may be substituted with one or more groups, such as, but not limited to, alkyl, hydroxy, alkoxy, amino, carboxyl, carboxyl ester, cyano, halogen, thio, acyl, aminoacyl, nitro, alkenyl, alkynyl, cycloalkyl, heterocycloalkyl, aryl, heteroaryl, and the like. In certain embodiments, the alkyl is substituted with an alkyl group, such as a $C_1$-$C_6$ alkyl, or a $C_1$-$C_3$ alkyl. In certain embodiments, the alkyl is substituted with an alkoxy group, such as a $C_1$-$C_6$ alkoxy, or a $C_1$-$C_3$ alkoxy. In certain embodiments, the alkyl group is substituted with a cycloalkyl group, such as a saturated or unsaturated cycloalkyl group. In certain embodiments, the alkyl group is substituted with an aryl. Combinations of the above substituents may also be included. The substituents on the substituted alkyl may in turn be substituted with one or more groups as described above, such as, but not limited to, alkyl, hydroxy, alkoxy, amino, carboxyl, carboxyl ester, cyano, halogen (e.g., F, Cl, Br, I), thio, acyl, aminoacyl, nitro, alkenyl, alkynyl, cycloalkyl, heterocycloalkyl, aryl, heteroaryl, and the like. In certain embodiments, $R^1$ is alkoxy or substituted alkoxy. In certain embodiments, $R^1$ is cycloalkyl or substituted cycloalkyl. In certain embodiments, $R^1$ is cycloalkyl, such as $C_3$-$C_{10}$ cycloalkyl, or a $C_3$-$C_6$ cycloalkyl. In certain embodiments, $R^1$ is cyclohexyl. In certain embodiments, $R^1$ is a substituted cycloalkyl, where the cycloalkyl group is substituted with one or more groups as described above, such as, but not limited to, alkyl, hydroxy, alkoxy, amino, carboxyl, carboxyl ester, cyano, halogen (e.g., F, Cl, Br, I), thio, acyl, aminoacyl, nitro, alkenyl, alkynyl, cycloalkyl, heterocycloalkyl, aryl, heteroaryl, and the like. For example, the cycloalkyl group may be substituted with one or more alkyl groups, such as a $C_1$-$C_6$ alkyl, or a $C_1$-$C_3$ alkyl (e.g., methyl). In certain embodiments, $R^1$ is aryl or substituted aryl. In certain embodiments, $R^1$ is heterocyclyl or substituted heterocyclyl. In certain embodiments, $R^1$ is selected from the following:

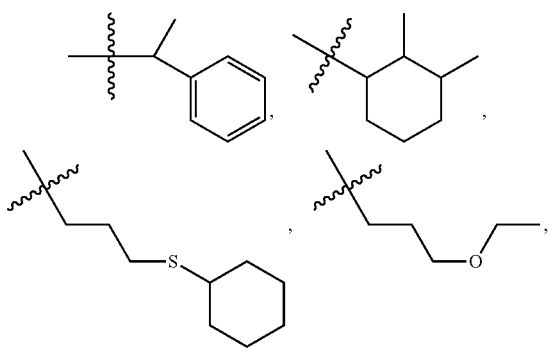

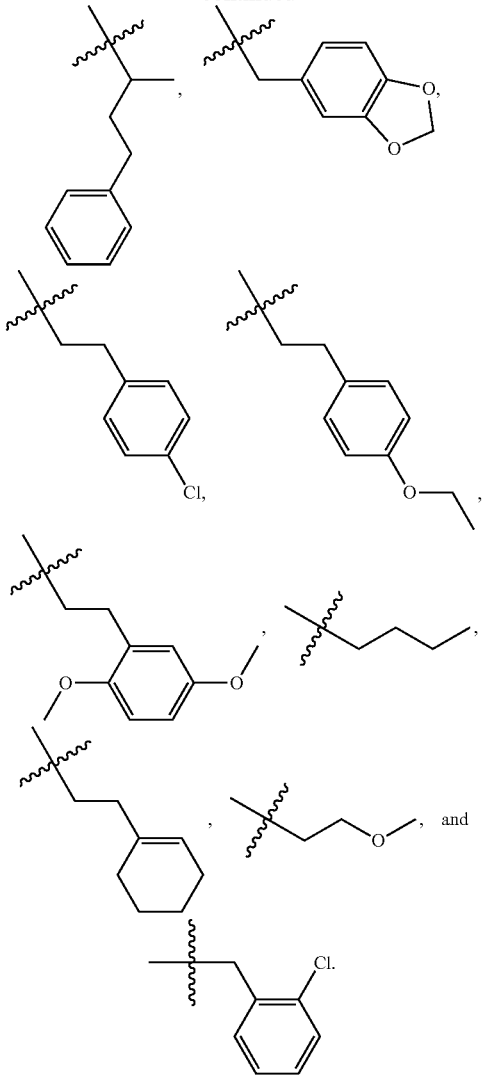

In Formula II, $R^2$ is selected from hydrogen, alkyl, and substituted alkyl. In certain embodiments, $R^2$ is hydrogen. In certain embodiments, $R^2$ is selected from alkyl. In certain embodiments, $R^2$ is substituted alkyl.

Particular compounds of interest, and salts or solvates or stereoisomers thereof for formulation according to the embodiments, include:

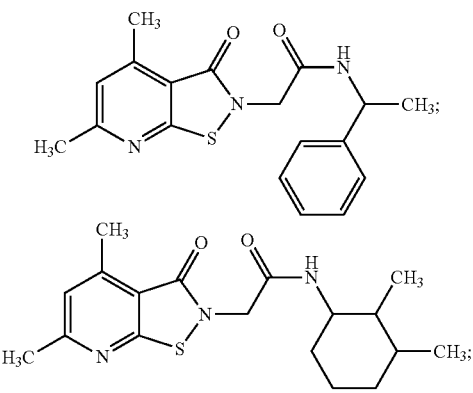

-continued
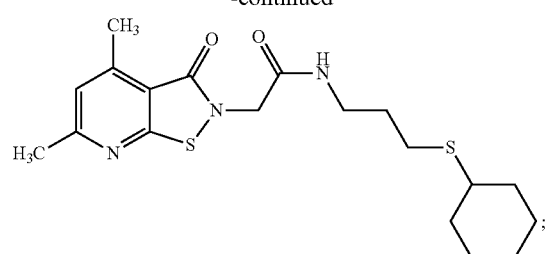
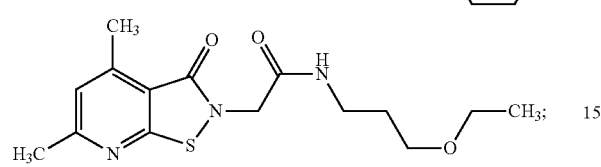
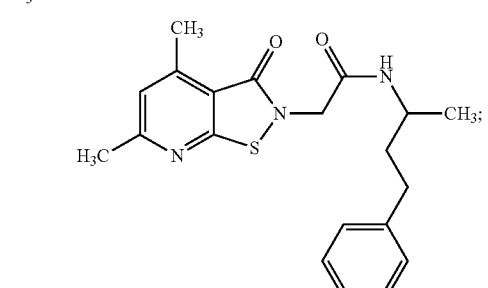
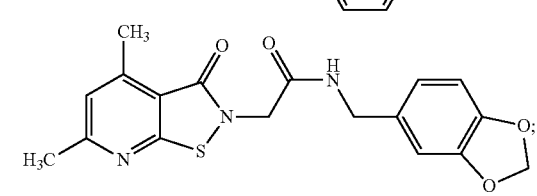
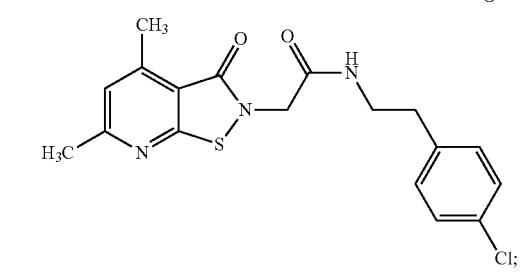
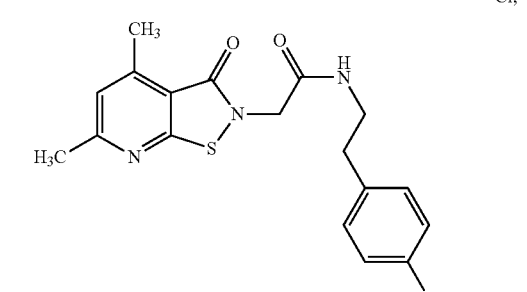
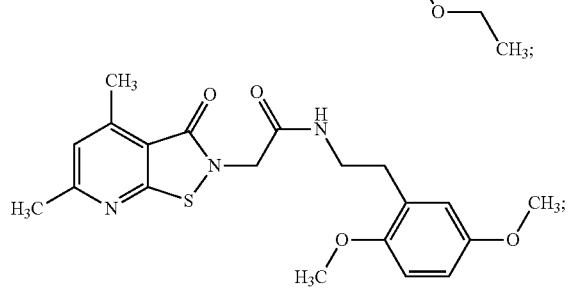
-continued
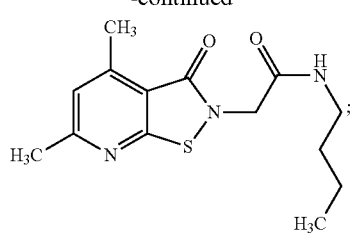
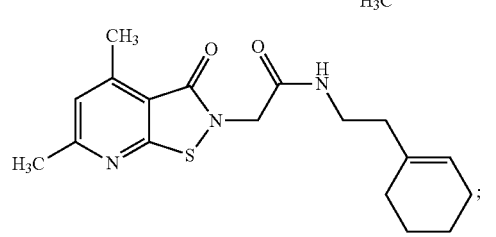
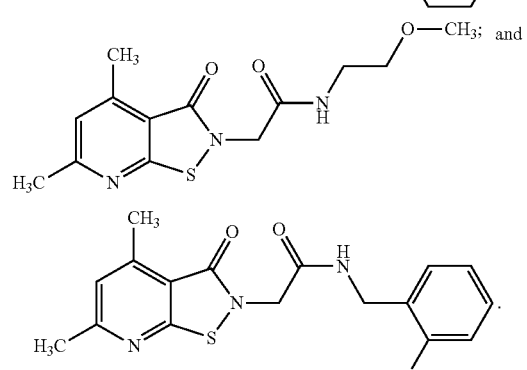
Formula IV-IX
Particular compounds of interest, and salts or solvates or stereoisomers thereof for formulation according to the embodiments, include:
(IV)
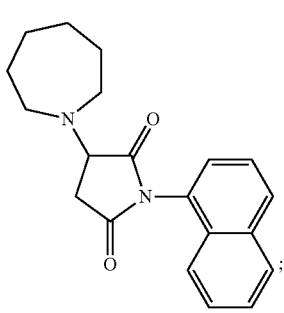
(V)
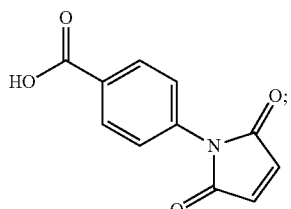
(VI)
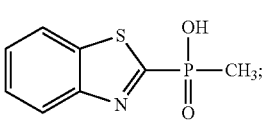

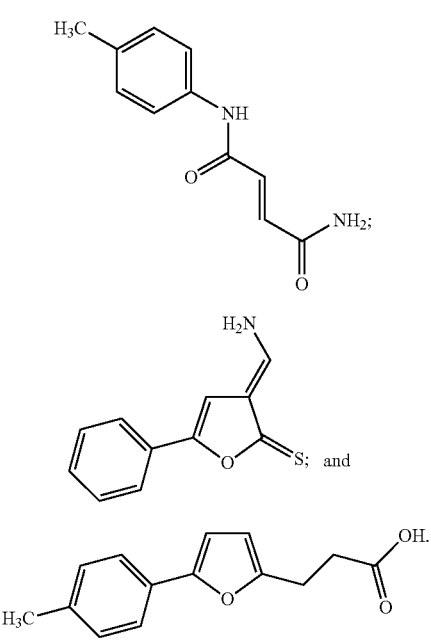

Pharmaceutical Formulations Comprising a Compound of Formula II, a Compound of any One of Formulae IV-IX or a Compound of Formula X The present disclosure provides pharmaceutical compositions comprising a compound of Formula II, comprising a compound of one of Formulas IV-IX, or a compound of Formula X. A compound of Formula II, a compound of one of Formulas IV-IX, or a compound of Formula X, is prepared in a pharmaceutically acceptable composition(s) for delivery to a host. In the context of pharmaceutical formulations, below, the terms "active agent," "drug," "agent," "therapeutic agent," and the like are used interchangeably herein to refer to a compound of Formula II, a compound of one of Formulas IV-IX, or a compound of Formula X.

In some instances, a composition comprising an active agent (e.g., a compound of Formula II, a compound of one of Formulas IV-IX, or a compound of Formula X) can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Formulations

In the subject methods, the active agent(s) may be administered to the host using any convenient means capable of resulting in the desired therapeutic effect or clinical outcome. Thus, an active agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent may be administered in the form of its pharmaceutically acceptable salt, or an active agent may also be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. The compounds of the present invention can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise an active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for a suitable dosage form depend, e.g., on the particular active agent employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition can include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of an active agent by the nasal mucosa.

An active agent can be administered in a composition suitable for injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Oral Formulations

In some embodiments, an active agent is formulated for oral delivery to an individual in need of such an agent.

For oral delivery, a formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for an active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include an active agent formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) Biomaterials 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly (lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an active agent formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix®(Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Controlled Release Formulations

In some embodiments, an active agent is formulated in a controlled release formulation.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, Controlled Release Technologies: Methods, Theory and Applications, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, Novel Drug Delivery Systems, 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. In one exemplary embodiment, an active agent can be contained in an enterically coated multiple-unit dosage form. In an exemplary embodiment, a dosage form comprising an active agent is prepared by spray-coating granules of the active agent-enteric coating agent solid dispersion on an inert core material. These granules can result in prolonged absorption of the active agent with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate Akihiko Hasegawa, Application of solid dispersions of Nifedipine with enteric coating agent to prepare a sustained-release dosage form, Chem. Pharm. Bull. 33: 1615-1619 (1985). Various enteric coating materials may be selected on the basis of testing to achieve an enteric coated dosage form designed ab initio to have an optimal combination of dissolution time, coating thicknesses and diametral crushing strength. S. C. Porter et al., The Properties of Enteric Tablet Coatings Made From Polyvinyl Acetate-phthalate and Cellulose acetate Phthalate, J. Pharm. Pharmacol. 22:42p (1970).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, Super Saturation Mechanism of Drugs from Solid Dispersions with Enteric Coating Agents, Chem. Pharm. Bull. 36: 4941-4950 (1998). The solid dispersions may be also called solid-state dispersions. The term "coprecipitates" may also be used to refer to those preparations obtained by the solvent methods.

The selection of the carrier may have an influence on the dissolution characteristics of the dispersed active agent because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of an active agent may also be increased owing to some interaction with the carriers.

Examples of carriers useful in solid dispersions include, but are not limited to, water-soluble polymers such as polyethylene glycol, polyvinylpyrrolidone, and hydroxypropylmethyl-cellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. Poorly water-soluble active agents may be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of an active agent with ethyl cellulose and stearic acid in different ratios.

There are various methods commonly known for preparing solid dispersions. These include, but are not limited to, the melting method, the solvent method and the melting-solvent method.

Another controlled release dosage form is a complex between an ion exchange resin and an active agent. Ion exchange resin-drug complexes have been used to formulate sustained-release products of acidic and basic drugs. In one exemplary embodiment, a polymeric film coating is provided to the ion exchange resin-drug complex particles, making drug release from these particles diffusion controlled. See Y. Raghunathan et al., Sustained-release drug delivery system I: Coded ion-exchange resin systems for phenylpropanolamine and other drugs, J. Pharm. Sciences 70: 379-384 (1981).

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid). Shigeyuki Takada, Utilization of an Amorphous Form of a Water-Soluble GPIIb/IIIa Antagonist for Controlled Release From Biodegradable Micro spheres, Pharm. Res. 14:1146-1150 (1997), and ethyl cellulose, Yoshiyuki Koida, Studies on Dissolution Mechanism of Drugs from Ethyl Cellulose Microcapsules, Chem. Pharm. Bull. 35:1538-1545 (1987).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate-release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet, production of which is comprised of two distinct steps: the drug in question is converted to an amorphous form through a combination of energy, excipients, and unique processing procedures.

Once converted to the desirable physical form, the resultant high energy complex may be stabilized by an absorption process that utilizes a novel polymer cross-linked technology to prevent recrystallization. The combination of the change in the physical state of an active agent coupled with the solubilizing characteristics of the excipients employed enhances the solubility of the active agent. The resulting absorbed amorphous drug complex granulate may be formulated with a gel-forming erodible tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of drug being both released locally and absorbed systemically. The combination of both approaches serves to minimize the potential harm of an active agent with resultant benefits to patients.

IPDAS is composed of numerous high density controlled release beads. Each bead may be manufactured by a two-step process that involves the initial production of a micromatrix with embedded active agent and the subsequent coating of this micromatrix with polymer solutions that form a rate-limiting semipermeable membrane in vivo. Once an IPDAS tablet is ingested, it may disintegrate and liberate the beads in the stomach. These beads may subsequently pass into the duodenum and along the gastrointestinal tract, e.g., in a controlled and gradual manner, independent of the feeding state. Release of the active agent occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of water soluble agents. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver an active agent. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain an active agent. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used to an active agent. DUREDAS was developed to provide for two different release rates, or dual release of a drug from one dosage form. The term bilayer refers to two separate direct compression events that take place during the tableting process. In an exemplary embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of an active agent may be desirable in order to facilitate a fast onset of therapeutic effect. Hence one layer of the tablet may be formulated as an immediate release granulate. By contrast, the second layer of the tablet may release the drug in a controlled manner, e.g., through the use of hydrophilic polymers. This controlled release may result from a combination of diffusion and erosion through the hydrophilic polymer matrix.

A further extension of DUREDAS technology is the production of controlled release combination dosage forms. In this instance, two different active agents may be incorporated into the bilayer tablet and the release of drug from each layer controlled to maximize therapeutic effect of the combination.

An active agent can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of an active agent and the release rates in a controlled release formulation, in order to optimize delivery of the active agent and its bioavailability.

Inhalational Formulations

An active agent will in some embodiments be administered to a patient by means of a pharmaceutical delivery system for the inhalation route. An active agent may be formulated in a form suitable for administration by inhalation. The inhalational route of administration provides the advantage that the inhaled drug can directly target the lung. An inhalational pharmaceutical delivery system is one that is suitable for respiratory therapy by delivery of an active agent to mucosal linings of the bronchi. This invention can utilize a system that depends on the power of a compressed gas to expel an active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in the context of the present disclosure, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing an active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present invention. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. Lastly, an active agent can be formulated into dry powder formulations. Such formulations can be administered by simply inhaling the dry powder formulation after creating an aerosol mist of the powder.

Dosages

Although the dosage used will vary depending on the clinical goals to be achieved, a suitable dosage range is one which provides up to about 1 μg to about 1,000 μg or about 10,000 μg of an active agent and can be administered in a single dose. Alternatively, a target dosage of an active agent can be considered to be about in the range of about 0.1-1000 μM, about 0.5-500 μM, about 1-100 μM, or about 5-50 μM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intracranial, subcutaneous, intradermal, topical application, intravenous, rectal, nasal, oral and other enteral and parenteral routes of administration. Routes of administration may be combined, if desired, or adjusted depending upon the agent and/or the desired effect. The composition can be administered in a single dose or in multiple doses. In some embodiments, the composition is administered orally. In other embodiments, the composition is administered intravenously. In other embodiments, the composition is administered via an inhalational route. In other embodiments, the composition is administered intramuscularly.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a neurological disorder and pain that may be associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), non-human primates, and primates (e.g., humans, chimpanzees, and monkeys). In some embodiments, the hosts will be humans.

Treatment Methods

The present disclosure provides a method of treating a patient suffering from a disorder characterized by excessive NO production and/or elevated DDAH activity, the method comprising administering to said patient an effective amount of a compound of one of Formulae I-X, e.g., where a compound of Formula Ia or a compound of Formula III is administered as an inhalational formulation. Disorders characterized by, or resulting from, excessive NO production and/or elevated DDAH activity include, e.g., fibrosis; sepsis; migraine headache, inflammation, autoimmune diseases, and certain cancers. In some cases, DDAH is reversibly inhibited.

Excessive NO production refers to NO production such that NO is present at a level that is greater than (e.g., 10% greater, 20% greater, 50% greater, or more than 50% greater) a normal control level of NO. Similarly, elevated DDAH activity is DDAH activity that is greater than (e.g., 10% greater, 20% greater, 50% greater, or more than 50% greater) a normal control level of DDAH activity.

Fibrosis

The present disclosure provides methods of treating fibrosis, e.g., fibrosis affecting any tissue including, for example, fibrosis of an internal organ, a cutaneous or dermal fibrotic disorder, fibrotic conditions of the eye, and vascular fibrosis. Fibrosis of internal organs (e.g., liver, lung, kidney, heart blood vessels, gastrointestinal tract) occurs in disorders such as pulmonary fibrosis, idiopathic fibrosis, autoimmune fibrosis, myelofibrosis, liver fibrosis, liver cirrhosis, veno-occlusive disease, mesangial proliferative glomerulonephritis, crescentic glomerulonephritis, diabetic nephropathy, renal interstitial fibrosis, renal fibrosis in subjects receiving cyclosporin, endomyocardial fibrosis, bronchiolitis obliterans (a fibrotic process that can occur after lung transplantation, after exposure to a toxin, or after an infection), and the like. Liver fibrosis, used interchangeably herein with "hepatic fibrosis," can occur in the context of a chronic hepatitis infection, or in the context of an injury (e.g., exposure, such as chronic exposure, to a toxin). Dermal fibrotic disorders include, for example, scleroderma, morphea, keloids, hypertrophic scars, familial cutaneous collagenoma, and connective tissue nevi of the collagen type. Fibrotic conditions of the eye include conditions such as diabetic retinopathy, postsurgical scarring (for example, after glaucoma filtering surgery, or after strabismus surgery), and proliferative vitreoretinopathy. Fibrosis can be triggered by interventional therapy, where such fibrosis includes, e.g. restenosis (e.g., restenosis following balloon angioplasty or following atherectomy). Vascular fibrosis includes, e.g., atherosclerosis, peripheral arterial disease, and the like.

In some cases, an effective amount of a compound of one of Formulae I-X is an amount that reduces collagen production by a fibroblast. For example, in some instances, an effective amount of a compound of one of one of Formulae I-X is an amount that reduces collagen production by a fibroblast by at least about 10%, at least about 15%, at least about 20%, at least about 25%, at least about 30%, at least about 35%, at least about 40%, at least about 45%, at least about 50%, or more than 50%, compared to the amount of collagen produced by the fibroblast in the absence of the compound.

Liver Fibrosis

In some cases, a subject method can be used to treat liver fibrosis. In some cases, an effective amount of a compound of one of one of Formulae I-X is an amount that, when administered as monotherapy or combination therapy to an individual having liver fibrosis, is effective to increase liver function, or stabilize liver function.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

In some cases, an effective amount of a compound of one of one of Formulae I-X is an amount that, when administered as monotherapy or combination therapy to an individual having liver fibrosis, is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include a2-macroglobulin, haptoglobin, gamma globulin, apolipoprotein A, and gamma glutamyl transpeptidase.

In some cases, an effective amount of a compound of one of one of Formulae I-X is an amount that, when administered as monotherapy or combination therapy to an individual having liver fibrosis, is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

Whether a subject treatment method is effective in reducing liver fibrosis is determined by any of a number of well-established techniques for measuring liver fibrosis and liver function. Liver fibrosis reduction can be determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of anti-fibrotic therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some cases, an effective amount of a compound of one of one of Formulae I-X is an amount that, in monotherapy or combination therapy, when administered to an individual having liver fibrosis, effects a change of one unit or more in the fibrosis stage based on pre- and post-therapy liver biopsies. In some cases, liver fibrosis is reduced by at least one unit in the METAVIR, the Knodell, the Scheuer, the Ludwig, or the Ishak scoring system.

Secondary, or indirect, indices of liver function can also be used to evaluate the efficacy of treatment with. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

Pulmonary Fibrosis

The present disclosure provides methods of treating pulmonary fibrosis. Pulmonary fibrosis can be caused by, e.g., chronic inflammatory processes such as sarcoidosis, Wegener's granulomatosis, etc.; infections; environmental agents (e.g., asbestos, silica, exposure to certain gases); exposure to ionizing radiation (such as radiation therapy to treat a tumor in the chest); chronic conditions (e.g., systemic lupus erythemato sus; rheumatoid arthritis; etc.); and certain medications. Pulmonary fibrosis can be caused by, or exacerbated by, the use of tobacco. In some patients, the cause of the pulmonary fibrosis is not understood; where the cause of pulmonary fibrosis is not understood, the pulmonary fibrosis is referred to as "idiopathic pulmonary fibrosis" (IPF).

In some embodiments, an effective amount of a compound of one of one of Formulae I-X is an amount that, in monotherapy or combination therapy, when administered to an individual having pulmonary fibrosis, is effective to reduce the pulmonary fibrosis or reduce the rate of progression of the pulmonary fibrosis by at least about 10%, at least about 15%, at least about 20%, at least about 25%, at least about 30%, at least about 35%, at least about 40%, at least about 45%, or at least about 50%, or more, compared with the degree of pulmonary fibrosis in the individual prior to treatment or compared to the rate of progression of pulmonary fibrosis that would have been experienced by the patient in the absence of the monotherapy or combination therapy.

In some embodiments, an effective amount of a compound of one of Formulas I-X is an amount that, in monotherapy or combination therapy, when administered to an individual having pulmonary fibrosis, is effective to increase the function of, or to reduce the rate of deterioration of, a lung of the individual by at least about 10%, at least about 15%, at least about 20%, at least about 25%, at least about 30%, at least about 35%, at least about 40%, at least about 45%, or at least about 50%, or more, compared to the basal level of lung function in the individual prior to the monotherapy or combination therapy or compared to the rate of deterioration in lung function that would have been experienced by the individual in the absence of the monotherapy or combination therapy. The severity of the disease, and its response to treatment, may be assessed by pulmonary function testing, e.g., spirometry, to assess lung volumes, compliance, and gas diffusion; by imaging methods, such as computerized tomography, to assess lung volumes and fibrosis; by functional testing such as treadmill exercise testing; by survival free of hospitalization; or by extension of life.

Idiopathic Pulmonary Fibrosis

The present invention disclosure provides methods of treating idiopathic pulmonary fibrosis (IPF). The methods generally involve administering to an individual in need thereof a compound of one of Formulas I-X.

In some embodiments, a diagnosis of IPF is confirmed by the finding of usual interstitial pneumonia (UIP) on histopathological evaluation of lung tissue obtained by surgical biopsy. The criteria for a diagnosis of IPF are known. Ryu et al. (1998) Mayo Clin. Proc. 73:1085-1101.

In other embodiments, a diagnosis of IPF is a definite or probable IPF made by high resolution computer tomography (HRCT). In a diagnosis by HRCT, the presence of the following characteristics is noted: (1) presence of reticular abnormality and/or traction bronchiectasis with basal and peripheral predominance; (2) presence of honeycombing with basal and peripheral predominance; and (3) absence of atypical features such as micronodules, peribronchovascular nodules, consolidation, isolated (non-honeycomb) cysts, ground glass attenuation (or, if present, is less extensive than reticular opacity), and mediastinal adenopathy (or, if present, is not extensive enough to be visible on chest x-ray). A diagnosis of definite IPF is made if characteristics (1), (2), and (3) are met. A diagnosis of probable IPF is made if characteristics (1) and (3) are met.

In some embodiments, an effective amount of a compound of one of Formulas I-X is an amount that, in monotherapy or combination therapy, when administered to an individual having pulmonary fibrosis, is effective to decrease IPF disease progression by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or more, compared with a placebo control or an untreated control.

Disease progression is the occurrence of one or more of the following: (1) a decrease in predicted forced vital capacity (FVC) of 10% or more; (2) an increase in A-a gradient of 5 mm Hg or more; (3) a decrease of 15% or more in single breath diffusing capacity ($DL_{CO}$). Whether disease progression has occurred is determined by measuring one or more of these parameters on two consecutive occasions 4 to 14 weeks apart, and comparing the value to baseline.

Thus, e.g., where an untreated or placebo-treated individual exhibits a 50% decrease in FVC over a period of time, an individual administered with an effective amount of a compound of one of Formulas I-X exhibits a decrease in FVC of 45%, about 42%, about 40%, about 37%, about 35%, about 32%, about 30%, or less, over the same time period.

In some embodiments, an effective amount of a compound of one of Formulas I-X is an amount that, in monotherapy or combination therapy, when administered to an individual having pulmonary fibrosis, is effective to increase progression-free survival time, e.g., the time from baseline (e.g., a time point from 1 day to 28 days before beginning of treatment) to death or disease progression is increased by at least about 10%, at least about 20%, at least about 25%, at least about 30%, at least about 40%, at least about 50%, at least about 60%, at least about 70%, at least about 80%, at least about 90%, at least about 2-fold, at least about 3-fold, at least about 4-fold, at least about 5-fold, or more, compared a placebo-treated or an untreated control individual. Thus, e.g., in some embodiments effective amounts are any dosages that is effective to increase the progression-free survival time by at least about 1 week, at least about 2 weeks, at least about 3 weeks, at least about 4 weeks, at least about 2 months, at least about 3 months, at least about 4 months, at least about 5 months, at least about 6 months, at least about 8 months, at least about 10 months, at least about 12 months, at least about 18 months, at least about 2 years, at least about 3 years, or longer, compared to a placebo-treated or untreated control.

In some embodiments, an effective amount of a compound of one of Formulas I-X is an amount that, in monotherapy or combination therapy, when administered to an individual having pulmonary fibrosis, is effective to increase at least one parameter of lung function, e.g., an effective amount of a compound of any one of Formulas I-X is any dosage that increases at least one parameter of lung function by at least about 10%, at least about 20%, at least about 25%, at least about 30%, at least about 40%, at least about 50%, at least about 60%, at least about 70%, at least about 80%, at least about 90%, at least about 2-fold, at least about 3-fold, at least about 4-fold, at least about 5-fold, or more, compared to an untreated individual or a placebo-treated control individual. In some of these embodiments, a determination of whether a parameter of lung function is increased is made by comparing the baseline value with the value at any time point after the beginning of treatment, e.g., 48 weeks after the beginning of treatment, or between two time points, e.g., about 4 to about 14 weeks apart, after the beginning of treatment.

In some embodiments, an effective amount of a compound of one of Formulas I-X is an amount that, in monotherapy or combination therapy, when administered to an individual having pulmonary fibrosis, is effective to increase the FVC by at least about 10% at least about 20%, at least about 25%, at least about 30%, at least about 40%, at least about 50%, at least about 60%, at least about 70%, at least about 80%, at least about 90%, at least about 2-fold, at least about 3-fold, at least about 4-fold, at least about 5-fold, or more compared to baseline on two consecutive occasions 4 to 14 weeks apart.

In some of these embodiments, an effective amount of a compound of one of Formulas I-X is an amount that, in monotherapy or combination therapy, when administered to an individual having pulmonary fibrosis, results in a decrease in alveolar:arterial (A-a) gradient of at least about 2 mm. Hg, at least about 7 mm Hg, at least about 10 mm Hg, at least about 12 mm Hg, at least about 15 mm Hg, or more, compared to baseline.

In some of these embodiments, an effective amount of a compound of one of Formulas I-X is an amount that, in monotherapy or combination therapy, when administered to an individual having pulmonary fibrosis, increases the single breath $DL_{CO}$ by at least about 15%, at least about 20%, at least about 30%, at least about 40%, at least about 50%, at least about 60%, at least about 70%, at least about 80%, at least about 90%, at least about 2-fold, at least about 3-fold, at least about 4-fold, at least about 5-fold, or more, compared to baseline. $DL_{CO}$ is the lung diffusing capacity for carbon monoxide, and is expressed as mL CO/mm Hg/second.

Parameters of lung function include, but are not limited to, forced vital capacity (FVC); forced expiratory volume ($FEV_1$); total lung capacity; partial pressure of arterial oxygen at rest; partial pressure of arterial oxygen at maximal exertion. Lung function can be measured using any known method, including, but not limited to, spirometry.

Sepsis

The present disclosure provides methods for treating sepsis. The methods generally involve administering to an individual in need thereof an effective amount of a compound of one of Formulas I-X.

In some embodiments, an effective amount of a compound of one of Formulas I-X is an amount that is effective to reduce an adverse symptom of sepsis. For example, in some embodiments, an effective amount of a compound of one of Formulas I-X is an amount that is effective to reduce the use of pressor agents needed to reverse the hypotension associated with sepsis by at least about 5%, at least about 20%, at least about 30%, at least about 40%, at least about 50%, at least about 60%, at least about 70%, at least about 80%, or more than 80%, compared to the use of pressor agents before treatment with the compound. Pressor agents (vasopressors) include, e.g., epinephrine, isoproterenol, norepinephrine, and the like.

In some cases, a subject method of treating sepsis comprises administering to an individual in need thereof an effective amount of a compound of one of Formulas I-X; and administering a second therapeutic agent, e.g., an antibiotic.

Individuals Suitable for Treatment

Individuals suitable for treatment with a subject method include individuals who have been diagnosed as having a disorder characterized by excessive NO production and/or elevated DDAH activity, where such individuals include, e.g., individuals who have been diagnosed as having fibrosis, individuals who have been diagnosed as having sepsis, etc. In some cases, individuals who have gastritis or gastric ulcer are specifically excluded.

In some cases, the individual is a human. In other instances, the individual is a non-human mammal, e.g., a canine, a feline, a rodent (e.g., a mouse; a rat), a non-human primate, an ungulate, etc. As one non-limiting example, in some cases, the non-human mammal is a canine, e.g., a dog that has IPF, e.g., a terrier such as a West Highland white terrier. Webb and Armstrong (2002) *Can. Vet.* 43:703.

Screening Methods

The present disclosure provides methods for identifying an agent that inhibits enzymatic activity of DDAH. The methods generally involve contacting a DDAH polypeptide with a DDAH substrate and a test agent; and determining the effect, if any, of the test agent on DDAH activity. Determining the effect of the test agent on DDAH activity involves detecting the product of action of DDAH on the DDAH substrate. A test agent that reduces the amount of product produced, compared to the amount of product produced in the absence of the test agent, is considered a DDAH inhibitor. Test agents that are DDAH inhibitors are candidate agents for treating a disease associated with excessive NO production and/or elevated DDAH activity. In some cases, a subject screening method can be used to exclude a test agent from further development when DDAH inhibition is not a desired effect.

As used herein, the term "determining" refers to both quantitative and qualitative determinations and as such, the term "determining" is used interchangeably herein with "assaying," "measuring," and the like.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising the DDAH polypeptide and the DDAH substrate in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

In some embodiments, a test compound of interest has an $IC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

Enzymatic activity of DDAH can be determined using any known assay. Colorimetric assays and fluorimetric assays can be used, depending on the nature of the product produced by action of DDAH on the DDAH substrate. The following are exemplary, non-limiting assays.

In some cases, an assay to determine DDAH enzymatic activity is a colorimetric assay that detects product (L-citrulline) formation from the substrate ADMA. DDAH can be mixed with ADMA and a test agent; and the effect of the test agent on DDAH activity is determined by measuring the amount of L-citrulline produced, using antipyrine (2,3-Dimethyl-1-phenyl-3-pyrazolin-5-one) and 2,3-butanedione oxime. For example, DDAH (e.g., recombinant human DDAH1) is mixed with ADMA in the presence of screening buffer in 384-well plates. Plates are incubated at 37° C. for 4 hours. Subsequently, color developing reagent (containing 2 volumes of antipyrine and 1 volume of 2,3-Butanedione oxime reagents) are added and the plates are incubated at 60° C. for 90 min prior to spinning them at 1,500 rpm for 5 min. In this assay, absorbance is proportional to the concentration of citrulline generated by DDAH.

As another example, an assay to determine DDAH enzymatic activity is a fluorimetric assay. For example, DDAH is mixed with the artificial substrate S-methyl-thiocitrulline (SMTC) and a test agent; and the effect of the test agent on DDAH activity is determined by measuring the amount of methanethiol produced. DDAH metabolizes SMTC into L-citrulline and methanethiol ($CH_3$—SH). The thiol released from the reaction can be monitored fluorimetrically by adding 7-Diethylamino-3-(4-maleimidophenyl)-4-methylcoumarin (CPM). The effect of small molecules that directly regulate DDAH activity can be monitored by comparing their fluorescence readout with that of no compound addition (control; vehicle).

A candidate agent can be assessed for any cytotoxic activity it may exhibit toward a living cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

In many embodiments, the screening method is carried out in vitro, in a cell-free assay. In some embodiments, the in vitro cell-free assay will employ a purified DDAH polypeptide, where "purified" refers to free of contaminants or any other undesired components. Purified DDAH polypeptide that is suitable for a subject screening method is at least about 50% pure, at least about 60% pure, at least about 70% pure, at least about 75% pure, at least about 80% pure, at least about 85% pure, at least about 90% pure, at least about 95% pure, at least about 98% pure, at least about 99% pure, or greater than 99% pure.

A DDAH polypeptide suitable for use in a subject screening method can comprise an amino acid sequence having at least about 85%, at least about 90%, at least about 95%, at least about 98%, at least about 99%, or 100%, amino acid sequence identity to a contiguous stretch of from about 250 amino acids to 285 amino acids of the amino acid sequence of a DDAH polypeptide as depicted in FIG. 15.

A DDAH polypeptide is readily prepared in a variety of host cells such as unicellular microorganisms, or cells of multicellular organisms grown in in vitro culture as unicellular entities. Suitable host cells include bacterial cells such as *Escherichia coli*; yeast cells such as *Saccharomyces cerevisiae, Pichia pastoris, Hansenula polymorpha, Kluyveromyces lactis, Yarrowia lipolytica, Candida utilis, Schizosaccharomyces pombe*, and the like; insect cells such as *Drosophila melanogaster* cells; amphibian cells such as *Xenopus* cells; mammalian cells, such as CHO cells, 3T3 cells, and the like.

In some embodiments, the in vitro cell-free assay will employ a fusion protein, comprising a DDAH polypeptide fused in-frame to a fusion partner. In some embodiments, the fusion partner is attached to the amino terminus of the DDAH polypeptide. In other embodiments, the fusion partner is attached to the carboxyl terminus of the DDAH polypeptide. In other embodiments, the fusion partner is fused in-frame to the DDAH polypeptide at a location internal to the DDAH polypeptide. Suitable fusion partners include immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; polypeptides that facilitate purification or isolation of the fusion protein, e.g., metal ion binding polypeptides such as 6H is tags (e.g., DDAH/6His), glutathione-S-transferase, and the like; polypeptides that provide for subcellular localization; and polypeptides that provide for secretion from a cell.

In some embodiments, the fusion partner is an epitope tag. In some embodiments, the fusion partner is a metal chelating peptide. In some embodiments, the metal chelating peptide is a histidine multimer, e.g., $(His)_6$. In some embodiments, a $(His)_6$ multimer is fused to the amino terminus of a DDAH polypeptide; in other embodiments, a $(His)_6$ multimer is fused to the carboxyl terminus of a DDAH polypeptide. The $(His)_6$-DDAH fusion protein is purified using any of a variety of available nickel affinity columns (e.g. His-bind resin, Novagen).

In some embodiments, a subject screening method is carried out in vitro in a cell, e.g., a cell grown in cell culture as a unicellular entity. Suitable cells include, e.g., eukaryotic cells, e.g., mammalian cells such as human umbilical vein endothelial cells (HUVEC; e.g., American Type Culture Collection (ATCC)CRL-1730), human microvascular endothelial cells (HMEC-1; ATCC CRL-4025), PC3 cells (ATCC CRL1435), MDA-MB-231 cells (ATCC HTB26), MCF-7 cells (ATCC HTB22), HeLa cells (ATCC No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), and the like.

In some cases, a cell in vitro is contacted with a test agent; and the effect of the test agent is determined by assaying the effect of the test agent on DDAH activity in lysates made from the cells.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Figure 2:
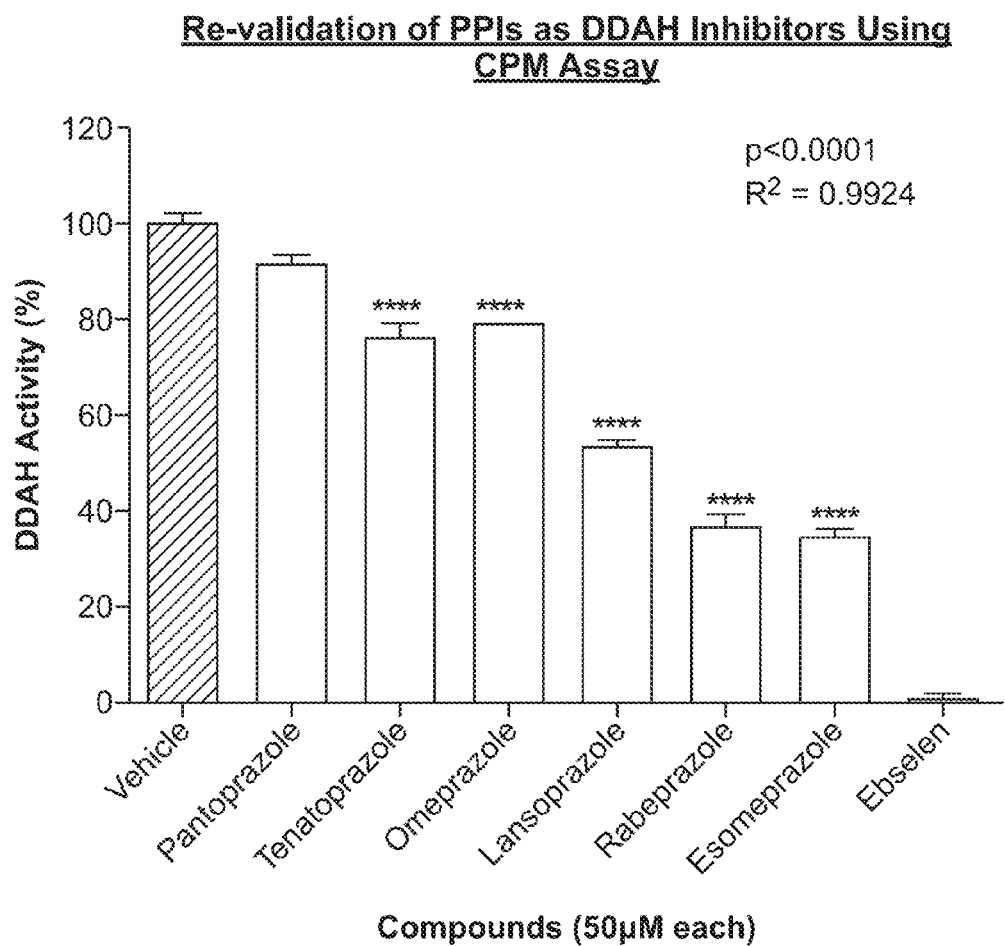
FIG. 2 is a graph showing re-validation of proton pump inhibitors (PPIs) as DDAH inhibitors using CPM assay.
Figure 3:
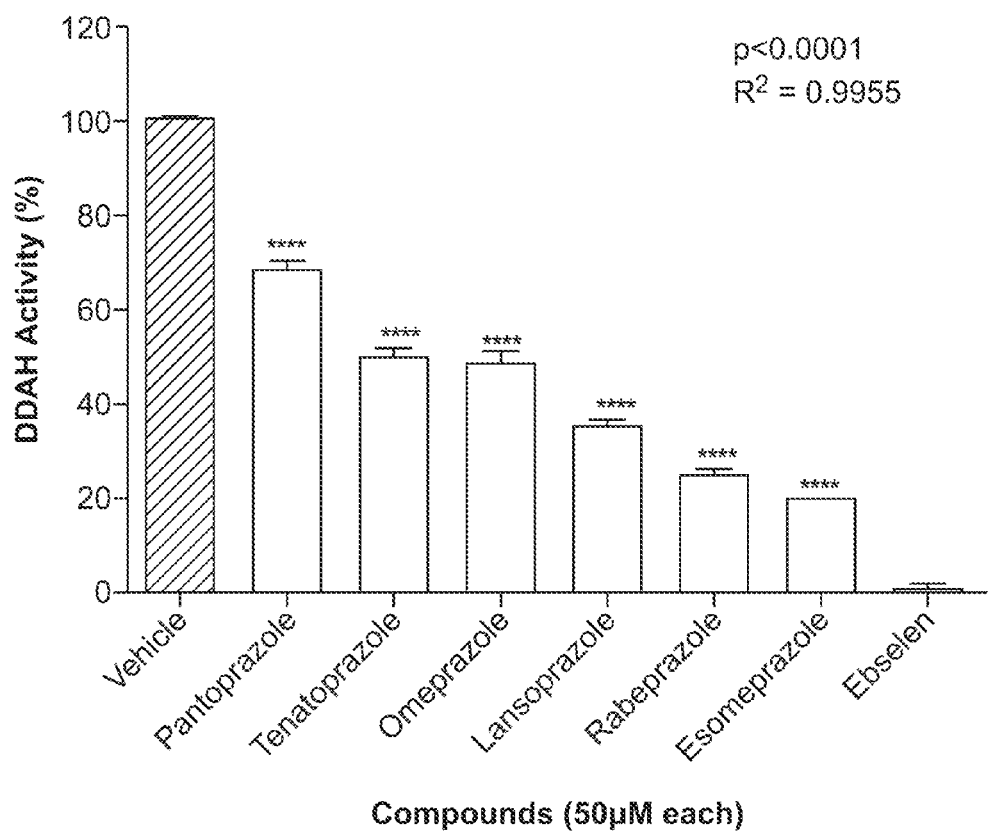
FIG. 3 is a graph showing an orthogonal assay to validate PPIs as DDAH inhibitors.
Figure 4:
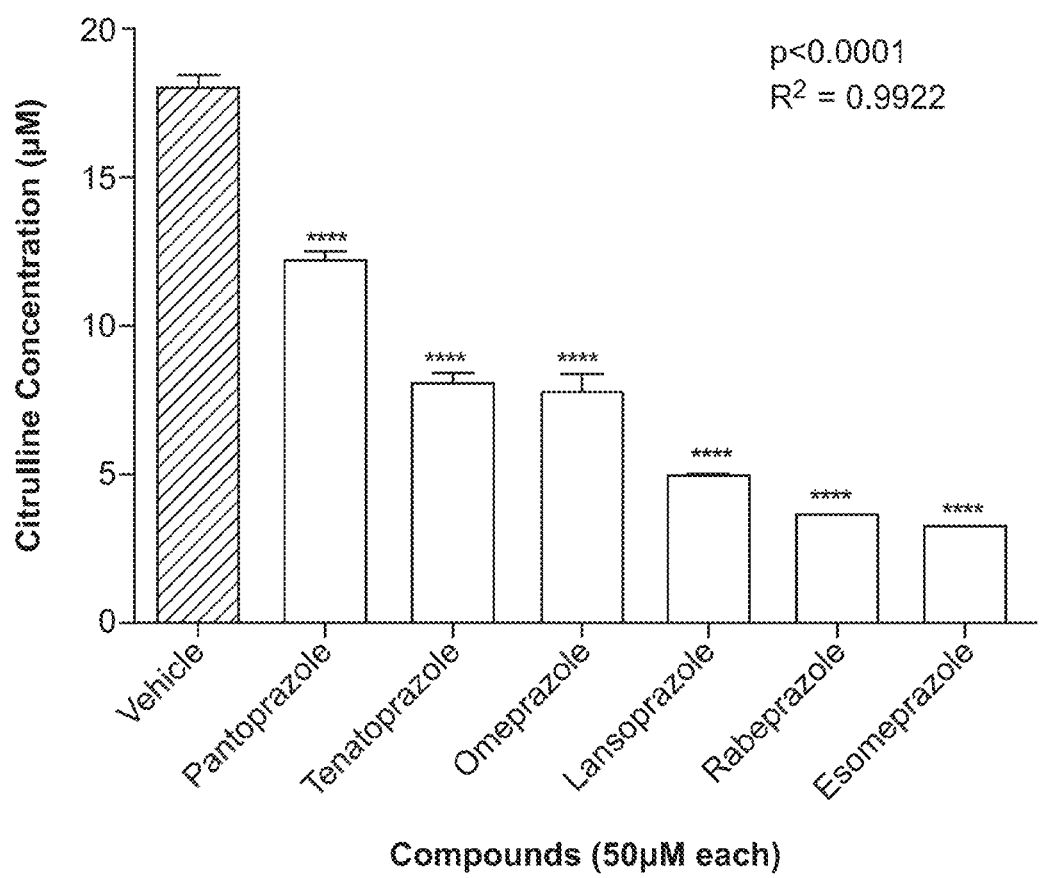
FIG. 4 is a graph showing production of L-citrulline from ADMA as a result of administration of various PPIs.

Compounds of Formula I as Novel Class of Dimethylarginine Dimethylaminohydrolase (DDAH) Inhibitors A high throughput screen was conducted using the Stanford High Throughput Bioscience Center (HTBC) chemical library to search for modulators of Dimethylarginine dimethylaminohydrolase (DDAH) activity.
Materials and Methods
Measurement of DDAH Activity:
The enzymatic activity of DDAH was monitored using a colorimetric assay that detects product (L-citrulline) formation from the substrate ADMA. In brief, recombinant human DDAH1 (rhDDAH1) was mixed with ADMA in the presence of screening buffer in 384-well plates. Plates were incubated at 37° C. for 4 hours. Subsequently, color developing reagent (containing 2 volumes of Antipyrine and 1 volume of 2,3-Butanedione oxime reagents) was added and the plates were incubated at 60° C. for 90 min prior to spinning them at 1,500 rpm for 5 min. In this assay absorbance is proportional to the concentration of citrulline generated by DDAH, and was measured using an AnalystGT plate reader at 485 nm using a dichroic beamsplitter.
Orthogonal Assay to Measure DDAH Activity:
The activity of human DDAH1 was quantified using fluorimetric assay by incubating the enzyme with an artificial substrate S-methyl-thiocitrulline (SMTC). DDAH metabolizes SMTC into L-citrulline and methanethiol ($CH_3$—SH). The thiol released from the reaction can be monitored fluorimetrically by adding 7-Diethylamino-3-(4-maleimidophenyl)-4-methylcoumarin (CPM). The effect of small molecules that directly regulate DDAH activity can be monitored by comparing their fluorescence (Top Read, Ex 360-35, Em 460-40, Dichroic 425) readout with that of no compound addition (vehicle).
Results
The high throughput based search for new chemical entities (NCEs) that regulate DDAH activity revealed several novel small molecules that are potent inhibitors of DDAH in a dose-dependent fashion. Among the DDAH inhibitors, four members of the proton pump inhibitors (PPIs) were discovered: Omeprazole (identified in 3 independent screens as STF-006355 in Biomol FDA (BMF)-6 with $IC_{50}$=61.4 µM), BMF-7 ($IC_{50}$=20 µM) and in MicroSource-2 as STF-006515 ($IC_{50}$=85 µM); Pantoprazole (identified in BMF-7 as STF-006577 ($IC_{50}$=63 µM); Lansoprazole (identified in MicroSource-10 as STF-001701 ($IC_{50}$=51 µM) and Tenatoprazole identified in BMF-8 as STF-008450 ($IC_{50}$=7.8 µM). The dose-dependent inhibition by each of the PPI inhibitors is shown in FIG. 1.
Compounds for Further Validation:
Validation studies were performed by obtaining fresh powders of each of the compounds directly from vendors and preparing them in a different location and independent of the tools used to initially perform the HTS screen. Stocks of each of the compounds were made using DMSO that has never been stored in the HTS facility and the prepared reagents were stored in freezers other than where the HTS screen compounds are kept.
Validation:
Compounds were validated for their direct effect on DDAH activity using the fluorometric assay described above. The validation study has confirmed the ability of the PPIs to directly inhibit DDAH activity (FIG. 2). As shown in FIG. 2, five of six PPIs inhibited DDAH significantly (*$p<0.05$). Ebselen was used as a positive assay control. The data shown is from triplicate experiments (Mean+/−SEM). In parallel, the compounds were also cross-validated to rule out the possibility that their apparent activity is caused by non-specific reaction quenching.
Testing of Additional Members of PPI Class:
An additional two compounds (Esomeprazole and Rabeprazole) were obtained as powders and tested for their effect on DDAH activity as described above. Both esomeprazole and rabeprazole also significantly inhibited DDAH activity (FIG. 3).
Cross Validation using an Orthogonal Assay:
Validation study using the CPM assay confirmed that all the six members of the PPI class (tenatoprazole, omeprazole, pantoprazole, lansoprazole, esomeprazole and rabeprazole) inhibited DDAH activity significantly ($p<0.05$). To further confirm these data, the above described orthogonal colorimetric assay was used to independently test the effect of these PPIs on DDAH activity. Interestingly, all the 6 PPIs significantly inhibited DDAH activity ($p<0.0001$; see FIG. 3) and reduced the production of L-citrulline substantially ($p<0.0001$; see FIG. 4). In the results shown in FIG. 3, Ebselen was used as a positive assay control. The data presented in FIG. 3 are from triplicate experiments (Mean+/−SEM).
The data in FIG. 4 show that production of L-citrulline from ADMA was significantly reduced (*$p<0.05$) when DDAH was pre-incubated with each of the six PPIs. In FIG. 4, L-citrulline concentration was calculated from a standard curve. Data are from triplicate experiments (Mean±SEM).
The discovery and validation of four members of the PPIs as direct inhibitors of DDAH activity in independent screening efforts and in more than one library indicates that the class of proton pump inhibitors might be acting on human DDAH1 through similar mechanism possibly by interacting with the active site cysteine (Cys 273). This finding is strengthened by the discovery of two additional members of the PPI class as significant inhibitors of DDAH activity and by the cross-validation of the findings using an orthogonal assay.

Validation of Proton Pump Inhibitors (PPIs) as DDAH Inhibitors in Cell-based Assay:

After validating the inhibition of DDAH activity by members of the PPI in vitro using a primary and an orthogonal assay, esomeprazole (Nexium) was taken as a prototype to study its effect on intracellular ADMA.

First, human microvascular endothelial cells (HMEC-1; ATCC) were seeded in 75 cm$^2$ cell culture flasks and cultured in fully supplemented DMEM (Invitrogen cat #11995; supplemented with 10% fetal bovine serum (FBS), 4 mM HEPES; GIBCO 15630 and penicillin/streptomycin). The cells were incubated at 37° C./5% $CO_2$ until ~60% confluency. The cells were then washed with phosphate buffered saline (PBS) and plain DMEM (DMEM with no addition of serum or the other supplements) was mixed with esomeprazole (20 µM final concentration from 100 mM stock) and added to the cells. In parallel, cells were also treated with vehicle (equal volume of dimethylsulfoxide (DMSO)) or a known DDAH inhibitor (L-257; Leiper J et al; Nature Med 2007; 13(2): 198-203). After ~4 hrs of incubation, the media was aspirated from each flask and the cells were cultured in fully supplemented DMEM as described above and incubated at 37° C./5% $CO_2$ for another 20 hrs. The serum was initially withdrawn due to the possibility that esomeprazole would interact with Cys containing serum proteins and fail to internalize at effective concentrations.

After 24 hrs, the cells were harvested. Total cellular protein was estimated as described and ADMA was measured by enzyme-linked immunosorbent assay (ELISA) following the manufacturer's recommendations; DLD Diagnostika, Hamburg, Germany).

Figure 5:
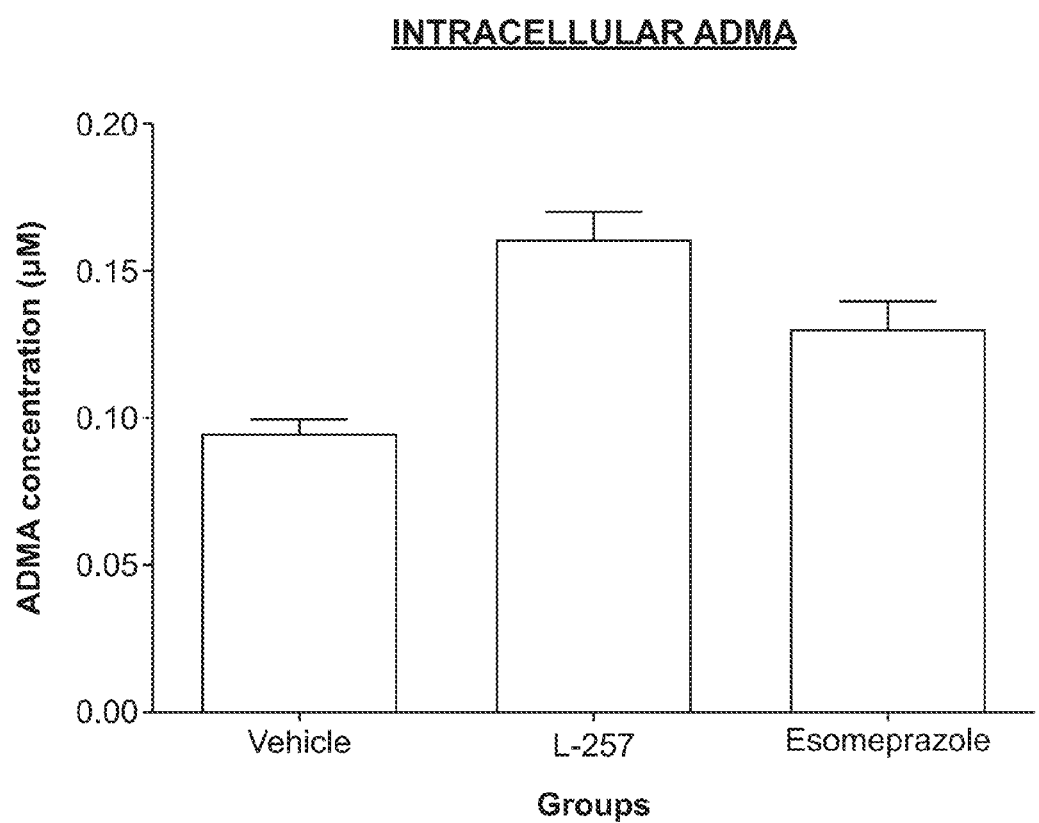
FIG. 5 is a graph that shows concentration of intracellular ADMA as a result of administration of various compounds.

The ADMA study demonstrated that esomeprazole increased intracellular ADMA (by ~37%) compared to vehicle control. L-257 (a known DDAH inhibitor; Leiper J et al; *Nat. Med.* 2007 February; 13(2):198-203.) also increased ADMA by 68% (FIG. 5, data are Mean+/−SEM from duplicates). In FIG. 5, endothelial cells were treated wtiht eh indicated small molecules (20 µM) or vehicle for 24 hours. These data indicate that PPIs (esomeprazole) may inhibit DDAH activity in mammalian cells.

Example 2

PD 404, 182 as a Novel and Potent Inhibitor of dimethylarginine dimethylaminohydrolase (DDAH)

Figure 6:
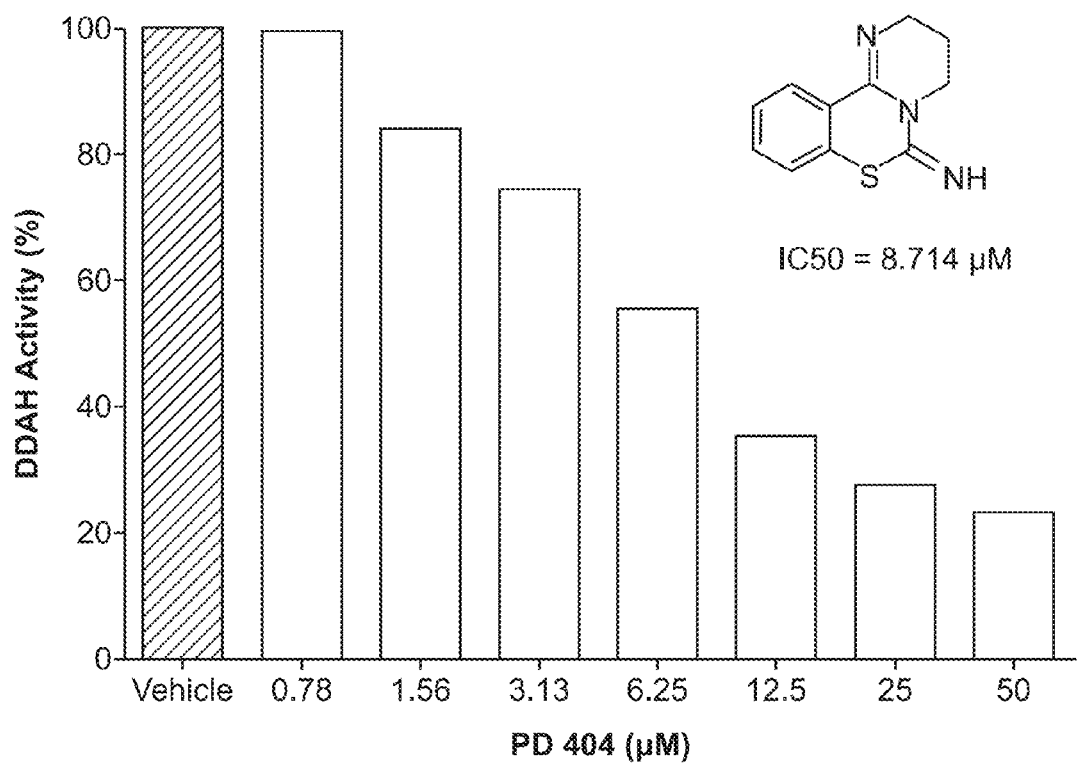
FIG. 6 is a graph showing direct inhibition of DDAH activity by small molecule PD 404.

In the high throughput screening of the Stanford chemical library, it was discovered that the small molecule PD 404, 182 (CAS #72596-74-8) is a very potent inhibitor of human DDAH1 (50% inhibitory concentration=$IC_{50}$=8.714 µM). This compound was deposited in the Library of Pharmacologically Active Compounds (LOPAC) library obtained by Stanford High Throughput Bioscience Center (HTBC) from Sigma and coded as STF-001938. As described below, PD-404 directly inhibits DDAH activity in a dose-dependent manner (FIG. 6).

Measurement of DDAH Activity:

The enzymatic activity of DDAH was monitored using a colorimetric assay that detects product (L-citrulline) formation from the substrate ADMA, as described in Example 1. In brief, recombinant human DDAH1 (rhDDAH1) was mixed with ADMA in the presence of screening buffer in 384-well plates. Plates were incubated at 37° C. for 4 hours. Subsequently, color developing reagent (containing 2 volumes of antipyrine and 1 volume of 2,3-Butanedione oxime reagents) was added and the plates were incubated at 60° C. for 90 min prior to spinning them at 1,500 rpm for 5 min. In this assay absorbance is proportional to the concentration of citrulline generated by DDAH, and was measured using an AnalystGT plate reader at 485 nm using a dichroic beamsplitter.

Orthogonal Assay to Measure DDAH Activity:

The activity of human DDAH1 was quantified using fluorimetric assay by incubating the enzyme with an artificial substrate S-methyl-thiocitrulline (SMTC), as described in Example 1. DDAH metabolizes SMTC into L-citrulline and methanethiol ($CH_3$—SH). The thiol released from the reaction can be monitored fluorimetrically by adding 7-Diethylamino-3-(4-maleimidophenyl)-4-methylcoumarin (CPM). The effect of small molecules that directly regulate DDAH activity can be monitored by comparing their fluorescence (Top Read, Ex 360-35, Em 460-40, Dichroic 425) readout with that of no compound addition (vehicle).

Results:

The high throughput-based search for new chemical entities (NCEs) that regulate DDAH activity revealed several novel small molecules that are potent inhibitors of DDAH in a dose-dependent fashion. Among the DDAH inhibitors, PD 404 was discovered (Stanford ID #: STF-001938) as shown in FIG. 6 ($IC_{50}$=8.714 µM).

Compound for Further Validation:

Validation study was performed by obtaining fresh powder of PD 404 directly from Sigma (Cat #P2742 at >98% high performance liquid chromatography (HPLC) purity) and preparing it in a different location and independent of the tools used to initially perform the HTS screen. Stock concentration was made using DMSO that has never been stored in the HTS facility and the prepared reagent was stored in a freezer other than where the HTS screen compounds are kept.

Figure 7:
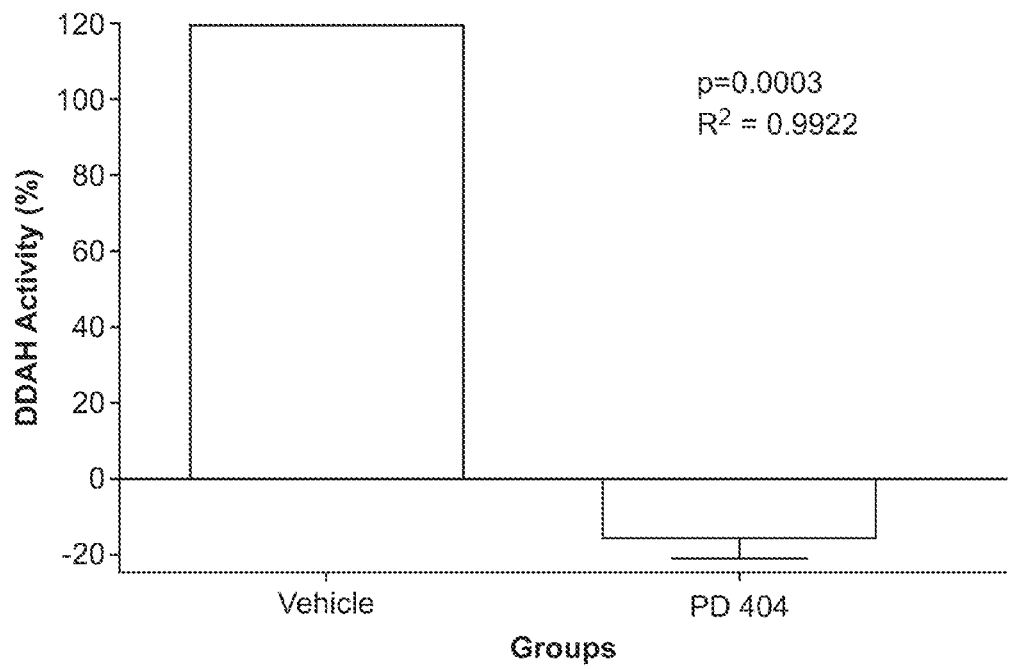
FIG. 7 is a graph showing re-validation of PD 404 as a DDAH inhibitor using CPM assay.

Validation:

PD 404 was validated for its direct effect on DDAH activity using the fluorometric assay described above. The validation study has confirmed the ability of PD 404 (50 µM) to directly inhibit DDAH activity (FIG. 7, data is Mean+/−SEM from triplicate experiments using CPM fluorometric assay), compared to vehicle control. In parallel, the compound was also cross-validated to rule out the possibility that its apparent activity is caused by non-specific reaction quenching.

Figure 8:
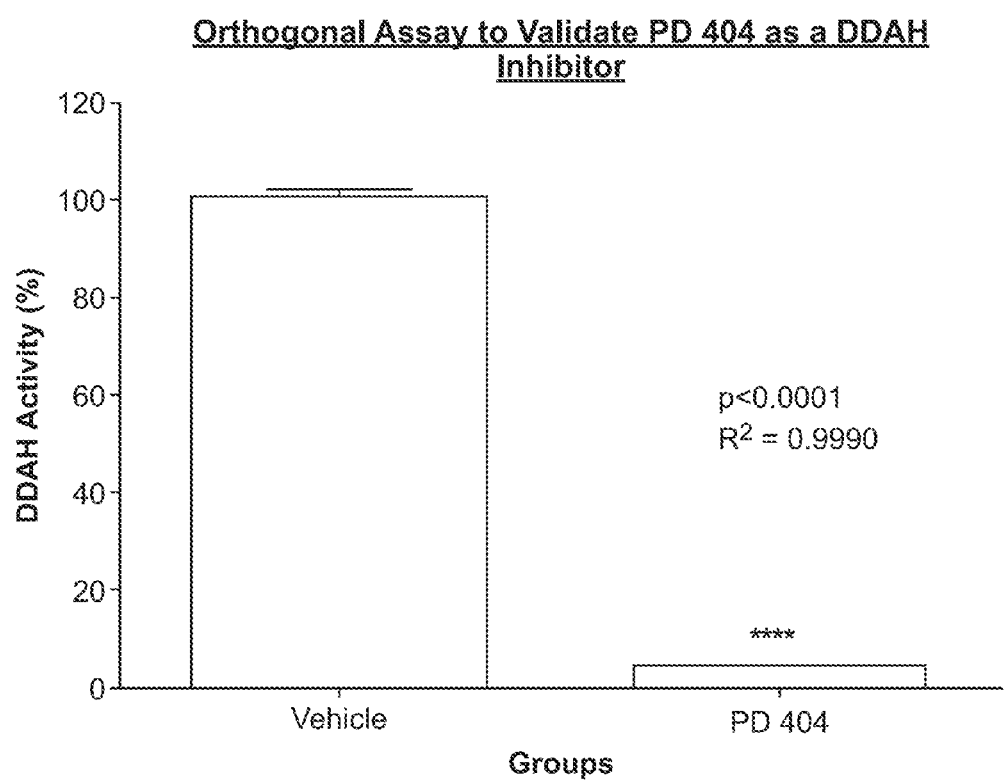
FIG. 8 is a graph showing an orthogonal assay to validate PD 404 as a DDAH inhibitor.

Cross Validation using an Orthogonal Assay:

Validation study using the CPM assay confirmed that PD 404 inhibited DDAH activity significantly (p<0.05). To further confirm these data, the above described orthogonal colorimetric assay was used to independently test the effect of this compound on DDAH activity. Interestingly, PD 404 (50 µM) significantly inhibited DDAH activity (p<0.0001; FIG. 8, data is Mean+/−SEM from triplicate experiments), compared to vehicle control.

Validation of PD 404 as DDAH Inhibitor in Cell-based Assay:

After validating the inhibition of DDAH activity by PD 404 in vitro using a primary and an orthogonal assay, its effect on intracellular ADMA was studied.

First, human microvascular endothelial cells (HMEC-1; ATCC) were seeded in 75 cm$^2$ cell culture flasks and cultured in fully supplemented DMEM (Invitrogen cat #11995; supplemented with 10% FBS, 4 mM HEPES; GIBCO 15630 and penicillin/streptomycin). The cells were incubated at 37° C./5% $CO_2$ until ~60% confluency. The cells were then washed with PBS and plain DMEM (DMEM with no addition of serum or the other supplements) was mixed with PD 404 (20 µM final conc from 100 mM stock) and added to the cells. In parallel, cells were also treated with vehicle (equal volume of DMSO) or a known DDAH inhibitor (L-257; Leiper J et al; Nature Med 2007; 13(2): 198-203). After ~4 hrs of incubation, the media was aspirated from each flask and the cells were cultured in fully supplemented DMEM as described above and incubated at 37° C./5% $CO_2$ for another 20 hrs. The serum was initially withdrawn due to the possibility that PD 404 would interact with Cys containing serum proteins and fail to internalize at effective concentrations. A recent study has demonstrated that PD 404 loses some of its bioactivity upon interaction with human serum (Chamoun A et al, Antimicrob. Agents Chemotherapy. doi:10.1128/AAC.05722-11).

After 24 hours, the cells were harvested. Total cellular protein was estimated as described and ADMA was measured by ELISA following the manufacturer's recommendations; DLD Diagnostika, Hamburg, Germany).

Figure 9:
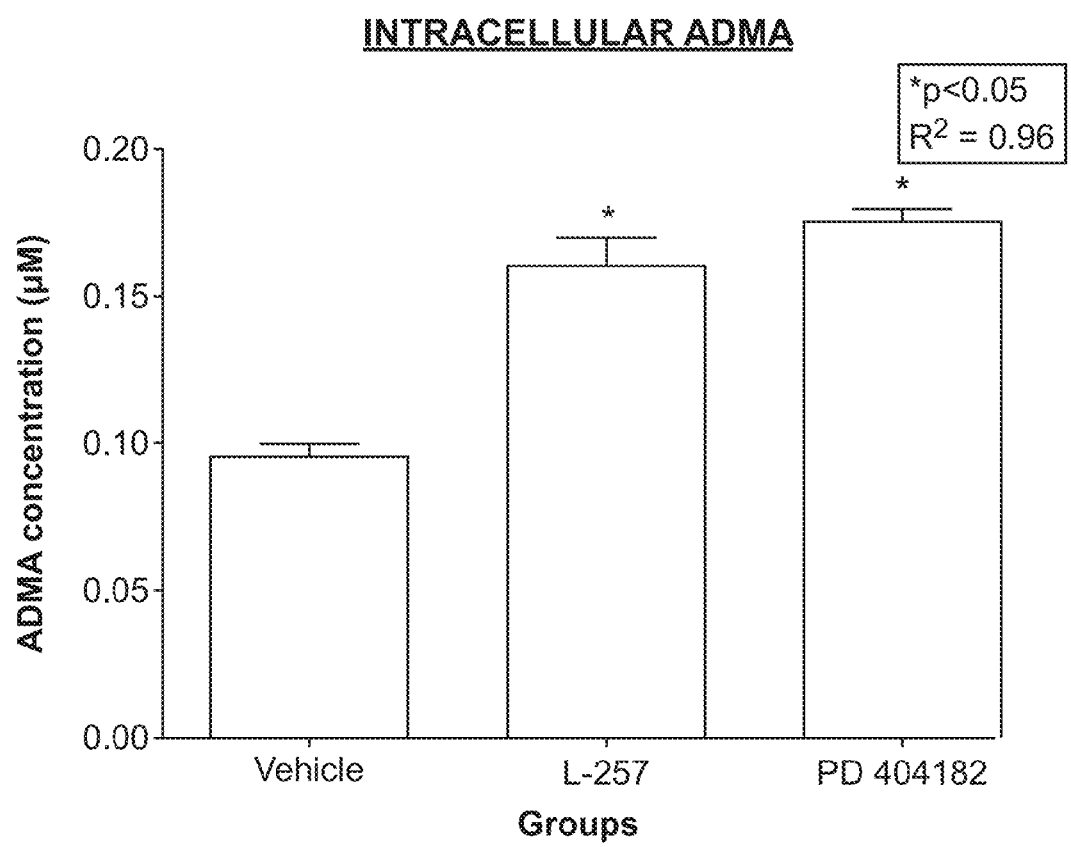
FIG. 9 is a graph showing production of L-citrulline from ADMA as a result of administration of PD 404.

Result:

The ADMA study demonstrated that PD 404 (20 µM) significantly increased intracellular ADMA (by ~84%) compared to vehicle control. L-257 (20 µM) also increased ADMA by 68% (FIG. 9, data are Mean+/−SEM from duplicates) compared to vehicle control. Endothelial cells were treated with the indicated small molecules (20 µM) or vehicle for 24 hours. These data indicate that PD 404 inhibits DDAH activity in mammalian cells.

Example 3

Development of a Dimethylarginine Dimethylaminohydrolase (DDAH) Assay for High Throughput Chemical Screening Materials and Methods The chemical library of the Stanford High Throughput Bioscience Center (HTBC) contains over 130,000 small molecules selected from diverse sources including Sigma, ChemDiv, MicroSource, ChemBridge, the NIH clinical collection (NIH CC), National Cancer Institute (NCI), natural products and FDA approved drug libraries using stringent criteria to maximize diversity and medicinal drug-like properties (http://htbc(dot)stanford(dot)edu/). The orthogonal assays, using hits derived from the HTBC, were conducted using chemicals purchased from Sigma-Aldrich (St. Louis, Mo.) unless indicated otherwise. For generation of DDAH protein, *E. coli* BL21 strain (Invitrogen) was used. The plasmid construct pGEX-6P-1-DDAH1 was used. Empty vector control, enzyme purification and cleavage reagents were from GE Healthcare (Piscataway, N.J.). Clear and black 384-well plates were from E&K Scientific (Santa Clara, Calif.). Antibodies directed against DDAH-1 (Abcam; Cambridge, Mass.) and GST (GE Healthcare) were obtained from commercial purveyors.

Production of Recombinant Human DDAH1:

Human DDAH1 was expressed in *E. coli* BL21 Star (DE3) strain for protein production. In parallel, cells were also transformed with empty vector. Positive clones were selected by polymerase chain reaction (PCR) and the clones harboring DDAH were subsequently inoculated into LB broth. Bacteria were grown at 37° C. (225 rpm) for 36 hours and preinduction samples were removed prior to inducing the remaining culture by adding isopropyl-beta-D-thiogalactopyranoside (IPTG; 0.1 mM final concentration) at 25° C. for 18 hours. The cells were harvested by centrifugation and the supernatant was discarded prior to lysing them with cell disruption buffer (containing 20 mM Tris-HCl; pH 8.0; 150 mM NaCl; 2 mM β-mercaptoethanol; 1 mM phenylmethylsulfonyl fluoride (PMSF); 1 mM benzamidine and 10 mM DNAse 1) and with 1% triton X-100 and lysozyme to break the peptidoglycan layer. The lysate was centrifuged at 20,000 g for 40 min at 4° C. and the supernatant was transferred into clean tubes for SDS-PAGE and Western analyses. The protein was purified using Glutathione sepharose 4B column in a batch mode according to the manufacturer's recommendations. The GST-tag was cleaved off the recombinant protein using Precision Protease. The purified protein was eluted, SDS-PAGE analyzed, and its identity was confirmed by Western and Mass Spectroscopy.

DDAH Activity Assay:

The L-citrulline assay was based upon an original test-tube method developed by Prescott and Jones in 1969 (Prescott, L. M. & Jones, M. E. Modified methods for the determination of carbamyl aspartate. *Anal Biochem* 32, 408-419 (1969)), which was adapted and optimized for a microplate format. Subsequently, the activity of DDAH was quantified by detecting its conversion of ADMA to citrulline using the optimized protocol. The assay was scaled up to a 384-well format for high throughput chemical screening.

High Throughput Screening of Small Molecules:

Over 130,000 small molecules deposited in the Stanford High-throughput Bioscience Center (HTBC) were screened using the enzymatic assay to identify chemicals that regulate DDAH activity. In brief, recombinant human DDAH1 (rhDDAH1) was mixed with ADMA in the presence of screening buffer in 384-well plates using a Staccato multidrop. Small molecules (100 nL each) were then added to the wells using a robotic arrayer to yield a final compound screening concentration of up to 50 µM. Plates were incubated at 37° C. for 4 hours. Subsequently, color developing reagent (containing 2 volumes of Antipyrine and 1 volume of 2,3-Butanedione oxime reagents) was added using Velocity 11 system and the plates were sealed using an automated plate sealer. Finally, color was developed by incubating the plates at 60° C. for 90 minutes prior to spinning them at 1,500 rpm for 5 minutes. In this assay absorbance is proportional to the concentration of citrulline generated by DDAH, and was measured using an AnalystGT plate reader at 485 nm using a dichroic beamsplitter. The signal-to-noise ratio of separation was calculated using an established formula in Zhang. (Zhang, J. H., Chung, T. D. & Oldenburg, K. R. A Simple Statistical Parameter for Use in Evaluation and Validation of High Throughput Screening Assays. *J Biomol Screen* 4, 67-73 (1999)).

Identification of Primary Hits:

Inhibitors were defined as compounds that reduce absorbance by at least 30% compared to control wells. The hits were validated using 8-point full dose response study (50 µM to 0.39 µM in serial dilutions). A total of over 150 compounds, about 0.12% of the total compounds, caused a reduction in absorbance of at least 30%. To determine which of these hits were true inhibitors of DDAH activity, a modification of a validated secondary fluorometric assay was used, as described below. In parallel, compounds were also cross-validated by adding them in reaction mix containing all the components described above with the exception of the enzyme to rule out the possibility that their apparent activity is caused by non-specific reaction quenching and not directly inhibiting DDAH.

Secondary Assay to Validate Potential DDAH Inhibitors:

For the secondary assay, a fluorimetric assay that uses SMTC as a substrate was adapted. DDAH metabolizes SMTC into L-citrulline and methanethiol ($CH_3$—SH). In brief, DDAH (30 nM final concentration) was mixed with SMTC (100 µM final concentration), CPM (50 µM final concentration) and screening buffer (containing a final concentration of 0.01% Triton-X100 and 1 mM EDTA). The reaction mix was added to black 384-well plates to validate primary hits that modulate DDAH activity. The release of $CH_3$—SH was monitored fluorimetrically by adding 7-Diethylamino-3-(4-maleimidophenyl)-4-methylcoumarin (CPM) as described in Linsky (Linsky, T. & Fast, W. A continuous, fluorescent, high-throughput assay for human dimethylarginine dimethylaminohydrolase-1. *J Biomol Screen* 16, 1089-1097 (2011)).

Application of the L-Citrulline Assay to Cells:

The feasibility of the citrulline assay in cell culture was validated by measuring the levels of L-citrulline in cell lysates applying a protocol similar to that described above. First, primary microvascular endothelial cells (HMVECs) were seeded in 75 cm$^2$ cell-culture flasks until confluency. The cells were exposed to 1 mM of L-Arginine for 24 hours in the presence of vehicle control. The cells were washed with PBS and then dissociated with 3 mL of Accutase for 3 minutes at 37° C./5% $CO_2$. The cells were then pelleted down by centrifugation and lysed by adding lysis buffer (containing 100 mM $Na_2HPO4$; 1% NP-40; 1× protease and phosphatase inhibitors). The suspension was kept on ice for 30 minutes prior to centrifugation at 13,000 rpm for 30 minutes at 4° C. Finally, the cell debris was removed and the supernatant was collected for the citrulline assay. The citrulline assay was performed in a microplate assay as described above by transferring equimolar amounts of cell lysate and adding 0.5 volume of color-developing reagent. The mix was incubated at 60° C. for 90 minutes and absorbance was measured as described above. Known concentrations of commercial citrulline were used to construct standard curves and to estimate the concentration of citrulline in the samples.

Results

Figure 10:
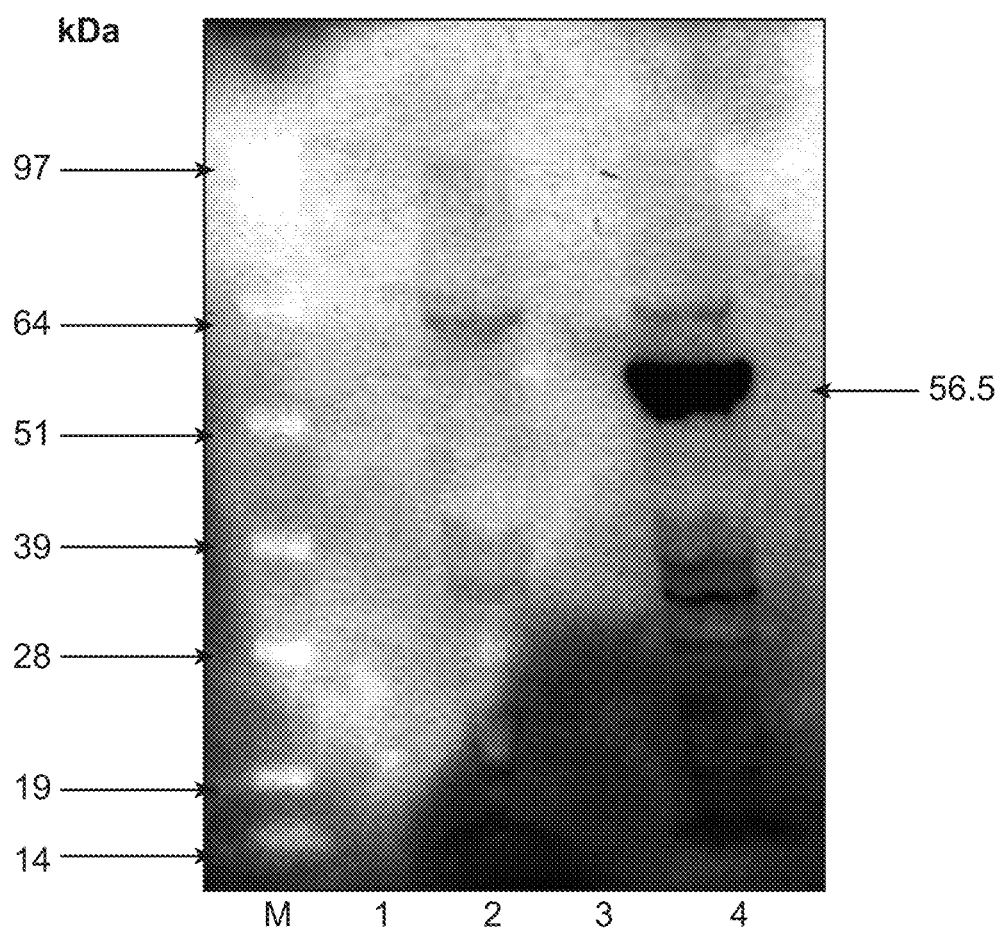
FIG. 10 shows a Western blot analysis showing the production of GST-DDAH (56.5 kDa).

A human DDAH-1 (858 bp)-encoding plasmid was successfully transformed into an *E. coli* system and the polymerase chain reaction (PCR)-positive clones were used for the production of rhDDAH1. Western blot analysis using both anti-DDAH1 and anti-glutathione-S-transferase (GST) antibodies confirmed that rhDDAH1 tagged with GST (56.5 kDa) was expressed only in the cells transformed with the vector encoding DDAH and induced by IPTG (FIG. 10). In FIG. 10, Western blot analysis shows the production of GST-DDAH (56.5 kDa). In FIG. 10, lanes 1,3: pre-induction; lane-2: post-induction sample of an empty vector; lane 4: isopropyl β-D-1-thiogalactopyranoside (IPTG) induction of DDAH vector. Lane-M is SeeBlue Plus molecular weight marker.

Figure 11A:
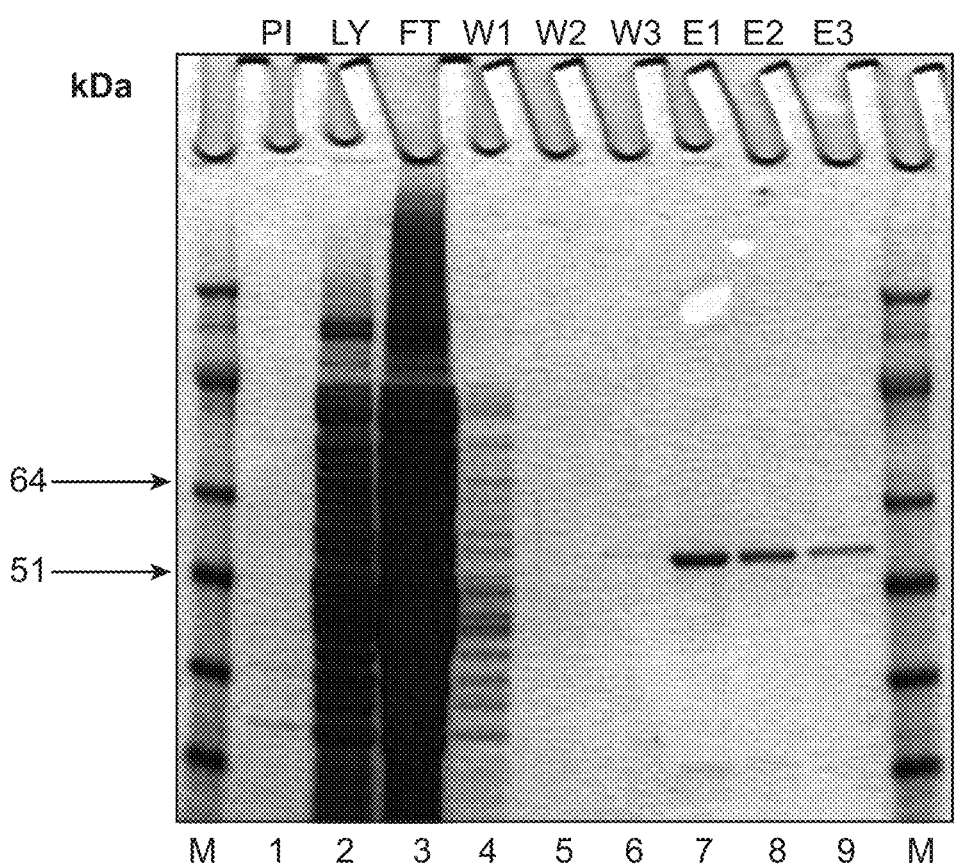
FIG. 11A shows SDS-PAGE analysis of purified human DDAH1.
Figure 11B:
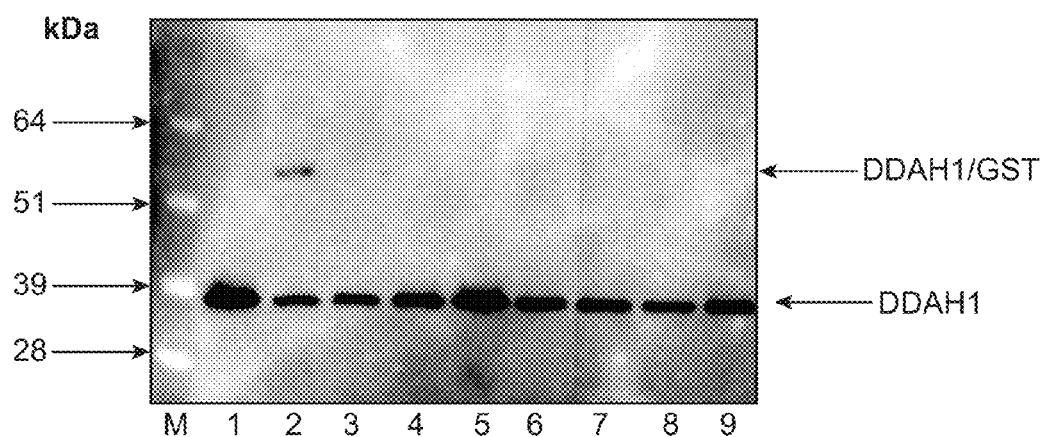
FIG. 11B shows Western blot showing purified (after GST cleavage) recombinant human DDAH1 (~37 kDa).

Sepharose column purification and subsequent sodium dodecyl sulfate-polyacrylamide gel electrophoresis (SDS-PAGE) (FIG. 11A) and Western blot analyses (FIG. 11B) revealed that the protein can be purified to a single band for use in screening experiments. FIG. 11A shows SDS-PAGE analysis of purified human DDAH1. In FIG. 11A, PI=pre-induction; LY=lysate; FT=flow through; W1=wash; E=eluent and M=1 kb+marker. FIG. 11B shows Western blot showing purified (after GST cleavage) recombinant human DDAH1 (~37 kDa). In FIG. 11B, GlPurified fractions of DDAH1 (lanes 1-9) were probed using anti-DDAH1 antibody. Despite earlier reports of difficulties producing soluble protein in an *E. coli* (BL 21) system, the protein yield was consistently above 2 mg/L culture, probably due to optimal induction time, RNAse and major protease deficient production system used in the experiments.

Figure 12:
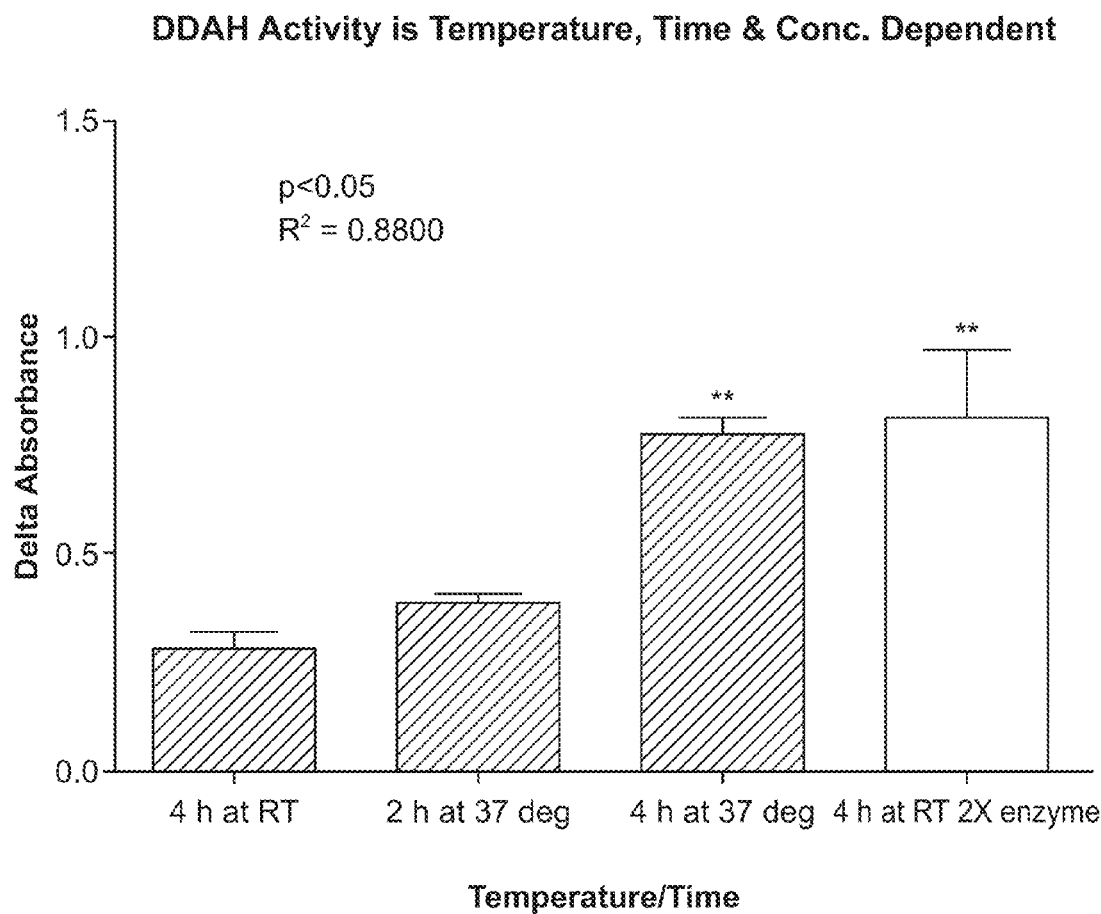
FIG. 12 shows a citrulline assay showing that the conversion of ADMA to L-citrulline by DDAH1 is proportional to time, temperature and enzyme concentration.

To find small molecule modulators of DDAH activity, an enzymatic assay that would lend itself to high throughput screening was developed. A microplate-based L-citrulline assay to measure DDAH activity has been previously reported in Knipp (Knipp, M. & Vasak, M. A colorimetric 96-well microtiter plate assay for the determination of enzymatically formed citrulline. *Anal Biochem* 286:257-264 (2000)); however, this protocol requires harsh conditions including heating the plates to a temperature of ~100° C. In a high throughput format, these conditions could cause sample evaporation and deformation of the reaction plates and thus this assay is not practical for the purpose of comprehensive screening. Accordingly, the conditions, including the amount of enzyme, substrate, incubation time and temperature, were optimized for a high throughput assay (FIG. 12). FIG. 12 shows a citrulline assay showing that the conversion of ADMA to L-citrulline by DDAH1 is proportional to time, temperature and enzyme concentration. Data are averaged from at least duplicate experiments.

Figure 13:
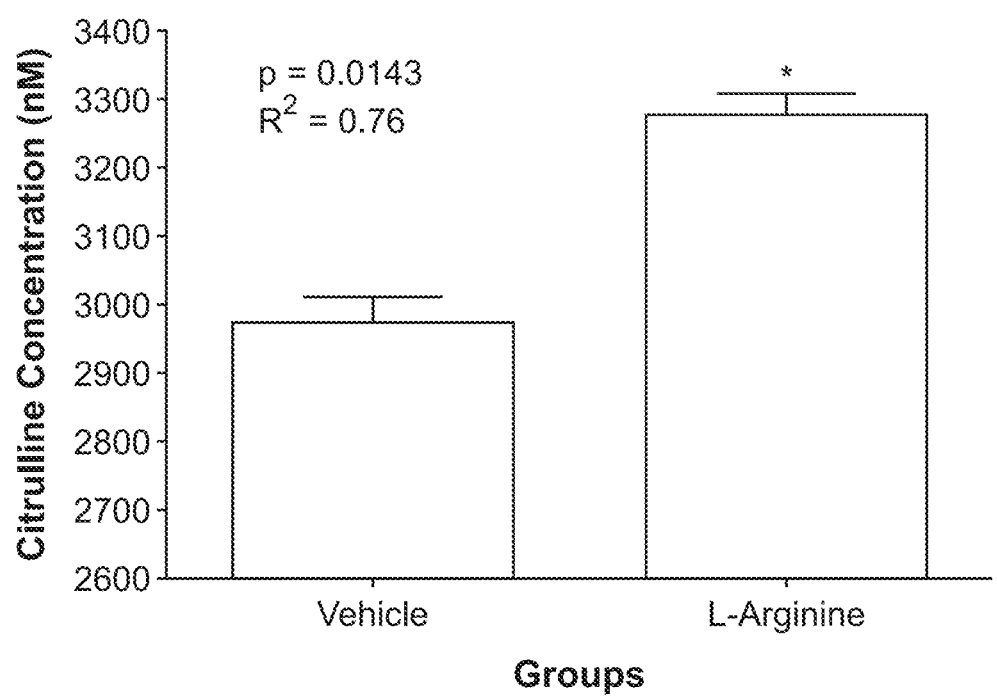
FIG. 13 shows measurement of L-citrulline from primary human endothelial cell lysate.
Figure 14A:
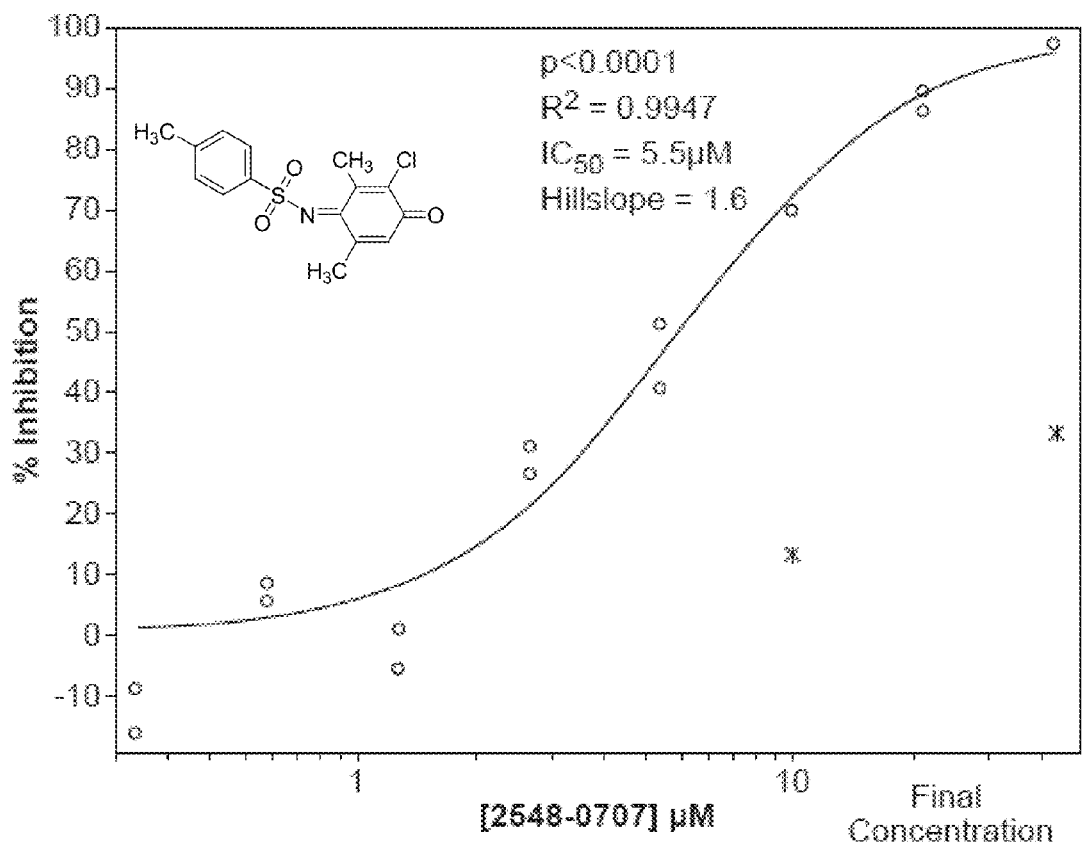
FIG. 14A-D show curve fit data showing inhibition of human DDAH-1 activity by selected small molecules using the CPM assay.
Figure 14B:
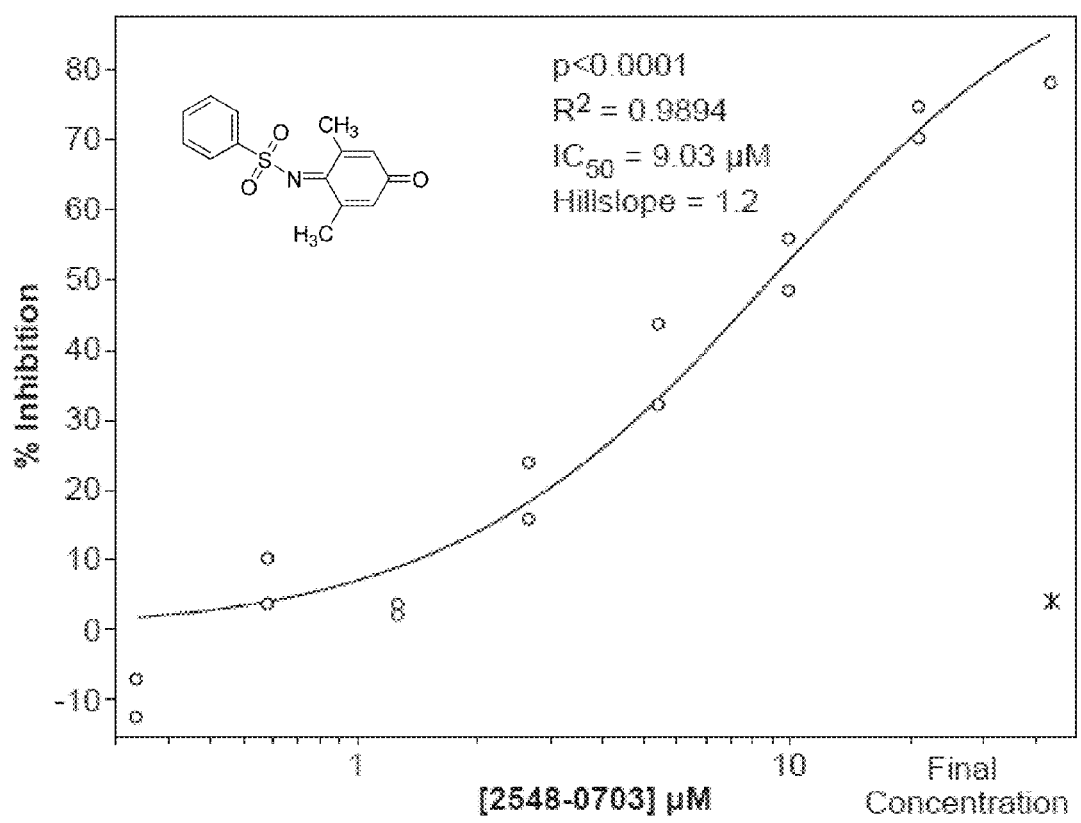
Figure 14C:
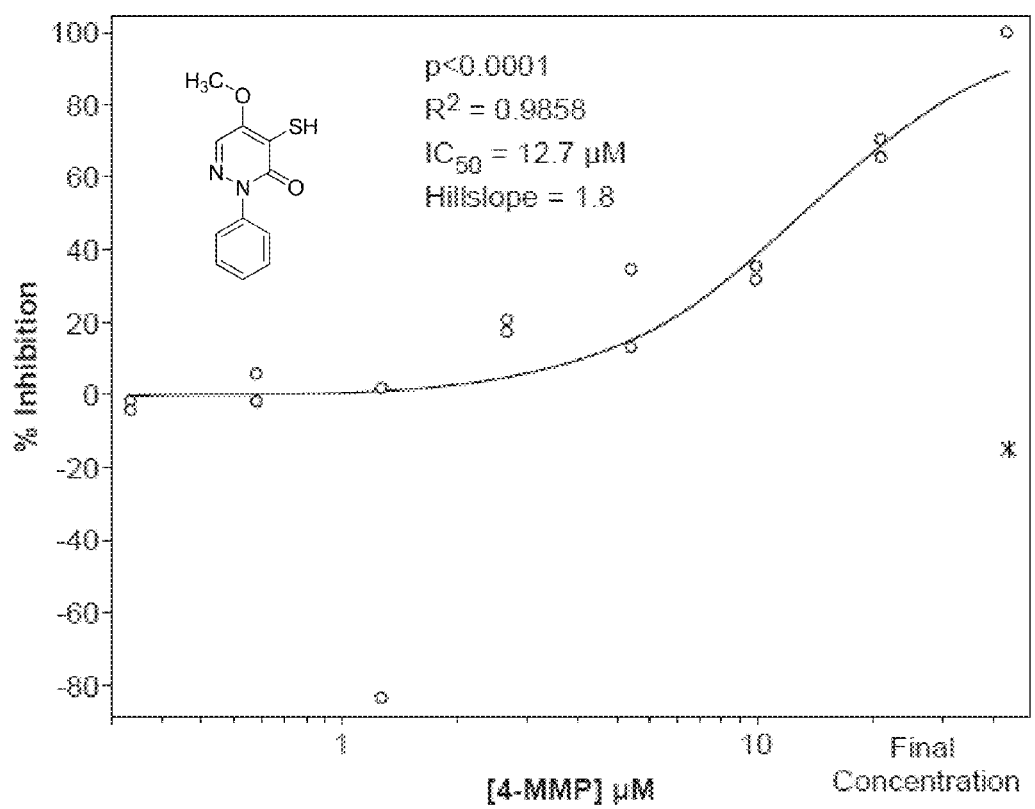
Figure 14D:
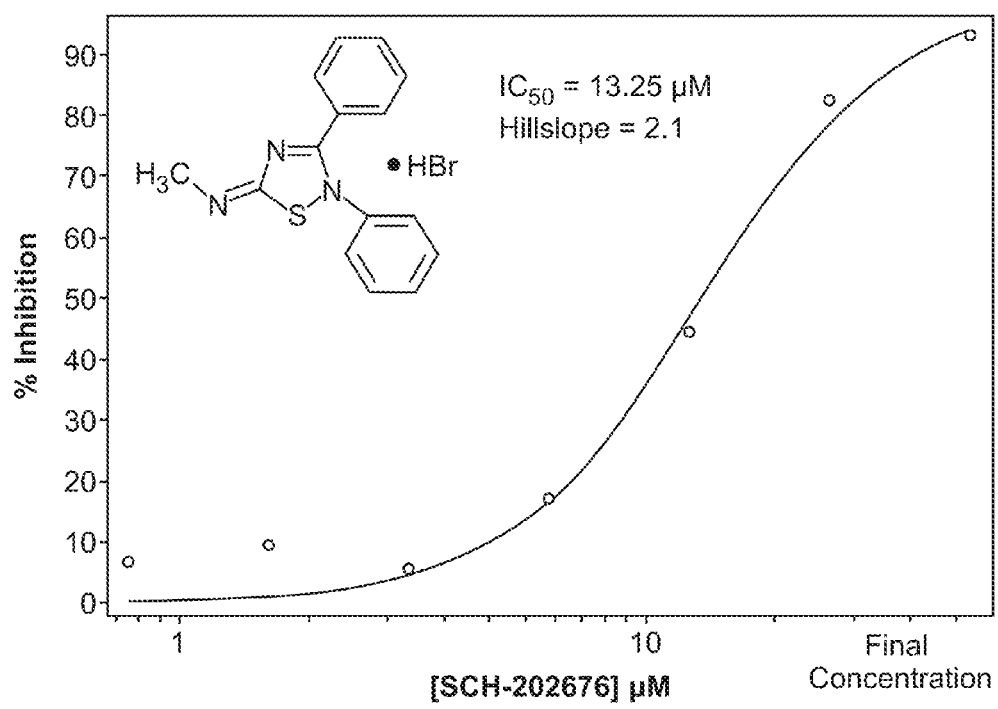

In brief, various amounts of rhDDAH1 (0.1 to 10 µM) were incubated with various concentrations of ADMA (1 µM to 8 mM) for various time points (30 min to 10 h) at room temperature or 37° C. In the final screening assay, catalytic activity ($k_{cat}$~0.7 min$^{-1}$) conditions at 0.3 µM of DDAH, 500 µM of ADMA ($K_m$=180 µM) and 4 hours of incubation time at 37° C. were used. The reactions were stopped and color was developed as described above followed by incubation at 60° C. for 90 min. Absorbance, proportional to DDAH activity, was measured at 485 nm±20 nm. In order to screen the entire library, the biochemical properties of the assay were optimized, as described above. The technique was modified so as to reduce the number of steps and facilitate robotic handling and throughput. Subsequently, HTS was performed using 384-well plates. The Stanford HTBC is equipped with a Caliper Life Sciences workstation for sample preparation and analysis, Titertek multidrops, microplate dispenser and automated liquid handler and laboratory robotics for screening of chemical libraries. The Z'-score was consistently found to be between 0.7 and 0.8, indicating the robustness of the assay. Furthermore, the feasibility of the assay was demonstrated in cell culture study by quantifying the amount of L-citrulline in endothelial cells treated with L-arginine or vehicle. As expected, pre-treatment with L-Arginine increased the amount of intracellular L-citrulline significantly (FIG. 13; p<0.05). In FIG. 13, M=measurement of L-citrulline from primary human endothelial cell lysate. Cells were treated with L-Arginine or Vehicle for 24 h and assayed for L-Citrulline levels. Values are mean+/−SEM. Experiments were performed in triplicates. *p<0.05.

Validation Assay

The concentration of SMTC as a substrate in the colorimetric citrulline assay described above was optimized. Subsequently, this substrate was used in the fluorimetric assay near its $k_{cat}$ ($k_{cat}$~1 min$^{-1}$) at 100 µM substrate concentration ($K_m$=1 µM), detecting the metabolite methanethiol ($CH_3$—SH) using the CPM reagent. This study, in conjunction with the citrulline assay, narrowed down the number of hits by reducing potential false positives, such as pan-assay interference compounds (PAINS). About 70% of the selected hits validated in the primary assay (about 35 compounds were retested in the secondary assay) were also inhibitors in the secondary fluorimetric assay. In addition, the validation assay also confirmed known DDAH inhibitors such as chloromercuribenzoate and ebselen and identified several new, potent inhibitors of human DDAHL Not surprisingly these include other mercury-containing compounds such as phenylmercuric acetate ($IC_{50}$<0.78 µM) and quinone-type compounds such as ChemDiv 2548-0707 ($IC_{50}$=5.5 µM) and 2548-0703 ($IC_{50}$=9.0 µM). However, it also includes more structurally novel compounds such as 4-mercapto-5-methoxy-2-phenyl-3(2H)-pyridazinone (4-MMP, $IC_{50}$=12.7 µM) and SCH-202676 ($IC_{50}$=13.3 µM) (FIG. 14). FIG. 14 shows curve fit data showing inhibition of human DDAH-1 activity by selected small molecules using the CPM assay: A) ChemDiv Compound 2548-0707; B) ChemDiv Compound 2548-0703; C) 4-MMP; and D) SCH-202676. The inhibitory concentration at 50% ($IC_{50}$) was calculated using Assay Explorer software.

In addition, the time-dependence kinetics study with two of the compounds (phenylmercuric acetate and 4-chloromercuribenzoic acid) indicates progressive inhibition suggesting that their mode of inhibition might be irreversible.

Furthermore, the follow-up study on selected inhibitors using the citrulline assay also confirmed the activity of these inhibitors against human DDAH1. Given their structure, it is possible that many of the compounds inhibit DDAH by reacting with the active site cysteine. Additional inhibitors of human DDAH1 and their potencies are shown in Table 1.

TABLE 1

Inhibitors of human DDAH-1. The following compounds were validated in full dose-response curves. The inhibitory concentration at 50% ($IC_{50}$) was calculated using Assay Explorer software.

| Molecular Name | $IC_{50}$ (μM) | Hill Slope |
| --- | --- | --- |
| 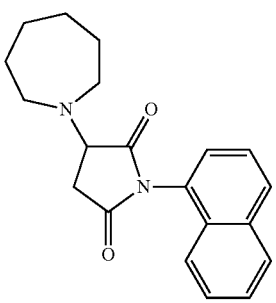 [SMILES: O=C1CC(N2CCCCCC2)C(=O)N1c1cccc2ccccc12] | 13.1 | 1.8 |
| 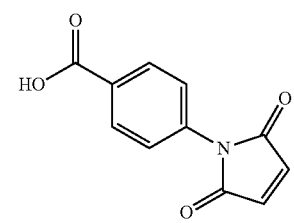 [SMILES: O=C(O)c1ccc(N2C(=O)C=CC2=O)cc1] | 23.3 | 1.6 |
| 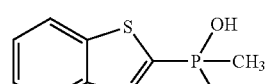 | 9.9 | 1.7 |
| 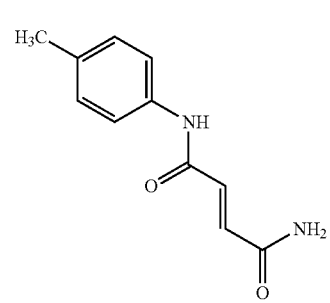 | 21.2 | 1.1 |
| 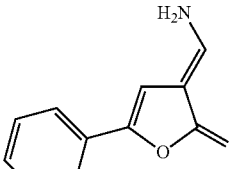 | 17.7 | 1.3 |
| 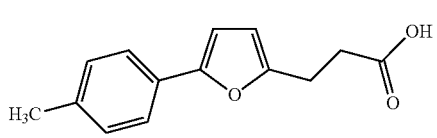 [SMILES: Cc1ccc(-c2ccc(CCC(=O)O)o2)cc1] | 45.8 | 1.1 |

TABLE 1-continued

Inhibitors of human DDAH-1. The following compounds were validated in full dose-response curves. The inhibitory concentration at 50% ($IC_{50}$) was calculated using Assay Explorer software.

| Molecular Name | $IC_{50}$ (μM) | Hill Slope |
|---|---|---|
| [structure] | 13.7 | 1.7 |
| [structure] | 8.6 | 1.7 |
| [structure] | 12.8 | 1.6 |
| [structure] | 7.1 | 2.3 |
| [structure] | 14.1 | 1.6 |
| [structure] | 11 | 1.5 |

TABLE 1-continued
Inhibitors of human DDAH-1. The following compounds were validated in full dose-response curves. The inhibitory concentration at 50% (IC$_{50}$) was calculated using Assay Explorer software.
| Molecular Name | IC$_{50}$ (μM) | Hill Slope |
|---|---|---|
| 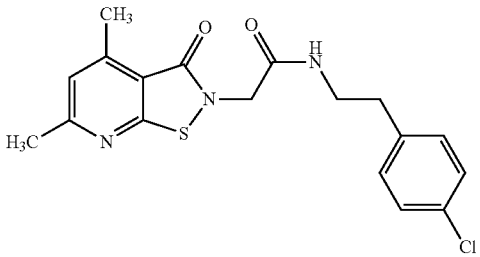 [SMILES: Cc1cc(C)c2c(=O)n(CC(=O)NCCc3ccc(Cl)cc3)sc2n1] | 13.4 | 1.2 |
| 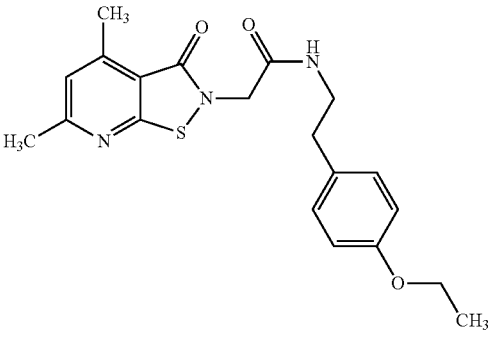 [SMILES: CCOc1ccc(CCNC(=O)Cn2sc3nc(C)cc(C)c3c2=O)cc1] | 10.5 | 1.5 |
| 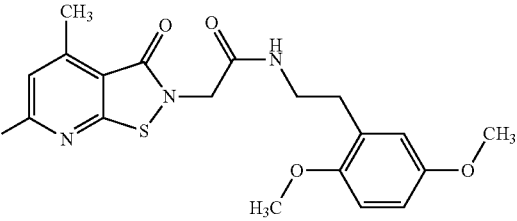 | 9.9 | 1.5 |
| 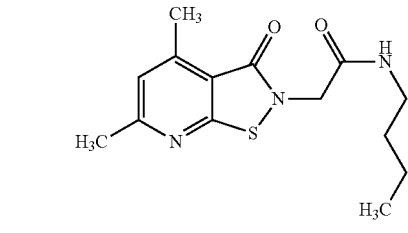 [SMILES: CCCCNC(=O)Cn1sc2nc(C)cc(C)c2c1=O] | 5.1 | 1.7 |
| 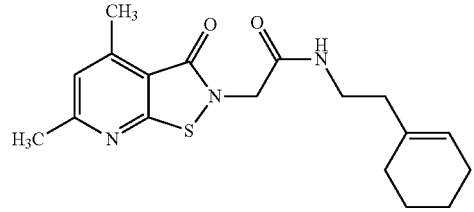 [SMILES: Cc1cc(C)c2c(=O)n(CC(=O)NCCC3=CCCCC3)sc2n1] | 11.8 | 2 |
| 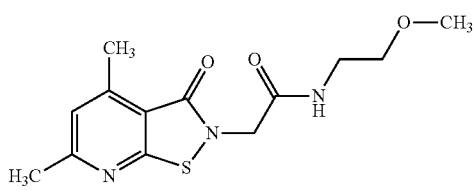 | 3.3 | 1.4 |

TABLE 1-continued

Inhibitors of human DDAH-1. The following compounds were validated in full dose-response curves. The inhibitory concentration at 50% ($IC_{50}$) was calculated using Assay Explorer software.

| Molecular Name | $IC_{50}$ (µM) | Hill Slope |
|---|---|---|
| [Structure: 4-methyl-6-methyl pyridine fused isothiazolone with N-CH2-C(O)-NH-CH2-(2-chlorophenyl) substituent] | 39.9 | 0.4 |
| [Structure: Benzo[d]isothiazol-3(2H)-one] | 13.2 | 1 |

Example 4

Benzo[d]isothiazol-3(2H)-one as a potent inhibitor of Dimethylarginine Dimethylaminohydrolase (DDAH)

Figure 17:
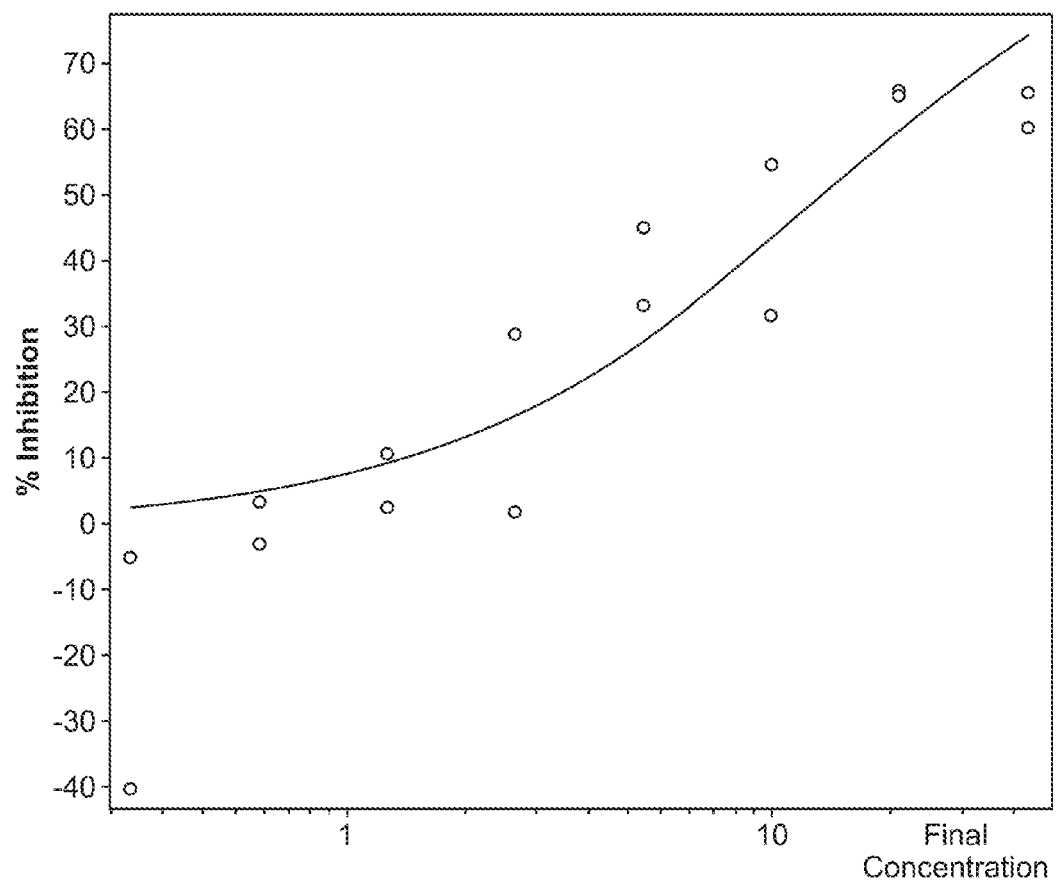
FIG. 17 shows curve fit data showing inhibition of DDAH activity by a compound of Formula X.
Figure 18:
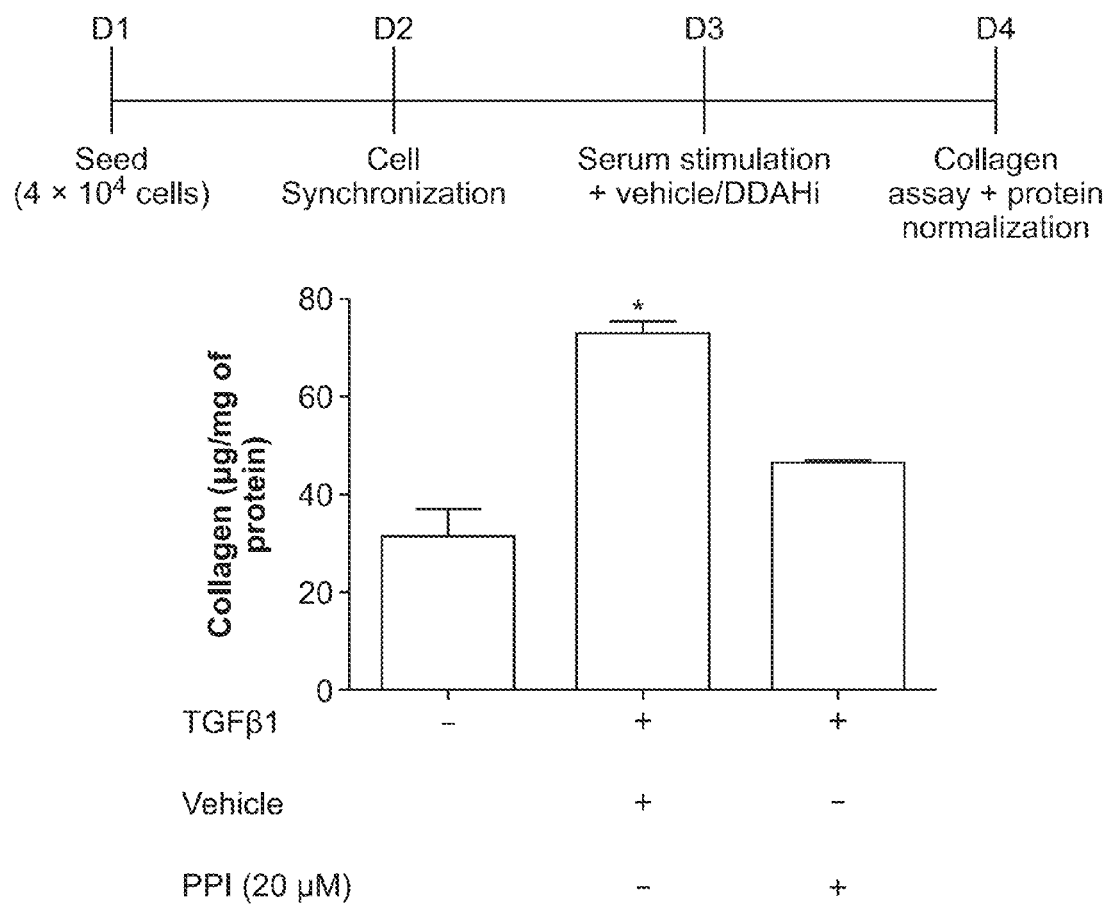
FIG. 18 depicts the effect of a proton pump inhibitor on collagen production by lung fibroblasts from patients with late-stage idiopathic pulmonary fibrosis.

Experiments were performed using the same protocols as in the Examples described above to test inhibition of DDAH activity by benzo[d]isothiazol-3(2H)-one. FIG. 17 shows curve fit data showing inhibition of DDAH activity by benzo[d]isothiazol-3(2H)-one. Benzo[d]isothiazol-3(2H)-one had an $IC_{50}$=13.2 µM and a Hill slope of 1 (see Table I).

Example 5

Effect of PPIs on Collagen Production by Lung Fibroblasts

Materials and Methods
Collagen Production in Quiescent Lung Fibroblasts Isolated from IPF Patients:
Characterization of IPF Lung Fibroblasts:

Lung fibroblasts from patients with late-stage IPF were isolated and extensively characterized by immunofluorescence staining for the expression of pan-mesenchymal markers such as vimentin and collagen IV; fibroblasts marker: Fibroblast Specific Protein (FSP1; S100A4); and smooth muscle cell markers such as alpha smooth muscle actin (α-SMA); skeletal-myosin heavy chain (sk-MHC); Caldesmon; Calponin and Desmin. In addition, endothelial phenotype was ruled out by negative staining for the endothelial cell-specific marker CD31.

The sources of the antibodies, their catalog numbers, and the working dilutions used in this characterization were as follows: Vimentin (Sigma V5255; Mouse at 1:100 dilution); FSP1 (Rabbit; Abcam ab41532 at 1:150); Collagen IV (Rabbit; Abcam; ab6586 at 1:100); α-SMA (Sigma A2547; Mouse at 1:400 dilution); skeletal-MHC (Mouse; Abcam ab32330 at 1:300); Caldesmon (Rabbit; Abcam ab32330 at 1:250); Calponin (Mouse; Abcam ab700 at 1:300); Desmin (Mouse; Sigma D1033 at 1:100) and CD31 (Dako M0823; Mouse; at 1:100 dilution).
Collagen Assay:

Cells were seeded at 4×10⁴ cells/well in a 6-well plate (1.2 mL media per well) and incubated overnight at 37° C./5% $CO_2$. The next day, the conditioned media was aspirated and the cells were rinsed with phosphate-buffered saline (PBS) prior to (fetal bovine) serum starving them for 2 hours followed by 22 hours low serum (0.1% fetal bovine serum; FBS) in order to synchronize them.

On day-3, the cells were stimulated with fully-supplemented media (containing 10% FBS) in the absence or presence of recombinant transforming growth factor-1 (TGF-β1) (at 10 ng/mL final conc) in the presence of a DDAH inhibitor (DDAHi; the proton pump inhibitor (PPI) lansoprazole at a final concentration of 20 µM) or vehicle for 24 hours.

The acid-soluble collagen content in each well was determined in the conditioned media using the Sircol collagen assay (Accurate Chemical and Scientific Corp; CLRS 1000) following the recommended protocol.

The amount of collagen in each well was estimated from a standard curve and the collagen content in each sample was normalized to total cellular protein from the respective well and was expressed as µg collagen per milligram of protein.
Results The IPF fibroblasts seeded in the presence of TGF-β showed significant elaboration of collagen production (over 2-fold increase) compared to the cells seeded in the absence of TGF-β. However, treatment with a proton pump inhibitor (PPI) nearly abolished the effect of TGF-β.

Example 6

Effect of PPIs on Alveolar Epithelial Cell Proliferation

Materials and Methods:
Proliferation Assay in Quiescent Lung Epithelial Cell Line:
Human Lung Carcinoma Cell Line with Type II Alveolar Epithelial Cell Property:

Human lung carcinoma cell line (A-549) was purchased from the American Type Culture Collection (ATCC; Manassas, Va.; Cat #CCL-185). This cell line is widely used to study human alveolar epithelial (AT II) cells due to the similarities with primary AT II cells (Lieber M et al "A continuous tumor-cell line from a human lung carcinoma with properties of type II alveolar epithelial cells"; Int. J. Cancer 1976; 17(1): 62-70; PMID: 175022). A detailed description and characterization (including additional references) of this cell line are available at the ATCC web site www(dot)atcc(dot)org).

The cells were cultured in Kaighn's Modification of Ham's F-12K (Invitrogen/Gibco cat #21127) supplemented with FBS (10%), Pen/Step (1%) and HEPES (2 mL in 500 mL Media). It was also established that the cells could as well be cultured in standard Dulbecco's Modified Eagle Medium (DMEM; Gibco cat #11995-065) supplemented with FBS (10%), Pen/Step (1%) and HEPES (2 mL in 500 mL Media).

BrdU Cell Proliferation Assay:

Cells were seeded at $5 \times 10^3$ cells/well in a 96-well plate (200 μL media per well) & incubated overnight at 37° C./5% $CO_2$. The next day, the conditioned media was aspirated and the cells were PBS-rinsed prior to (fetal bovine) serum starving them for 2 hours followed by 22 hours low serum (0.1% FBS) in order to synchronize them.

On day-3, 2 hours before the end of the 24 hours low serum period, DDAH inhibitors (Proton pump inhibitors; PPIs) were added in a 100 μL solution of 0.1% FBS DMEM. The following DDAH inhibitors were used: Lansoprazole; Esomeprazole; and Rabeprazole. A "vehicle only" sample served as a "no DDAH" control. In addition, Media only (blank control) without cells, and Cells only (background control) were included in the assay. Two hours later, 100 μL of DMEM containing 10% FBS was added to each well in order to serum-stimulate (for 24 hours) the cells and make the total well content to 200 μL. Four hours prior to the end of the 24 hrs, 20 μL of 1:500 diluted Bromodeoxyuridine (BrdU) (diluted in fully-supplemented DMEM) was added to all wells except the "Cells only" control wells.

The incorporation of BrdU into newly synthesized DNA by actively proliferating cells was detected immunochemically using an Antibody directed against BrdU using the recommended protocol and the BrdU Cell Proliferation Assay kit (Millipore; Cat #2750).

Results

Figure 19:
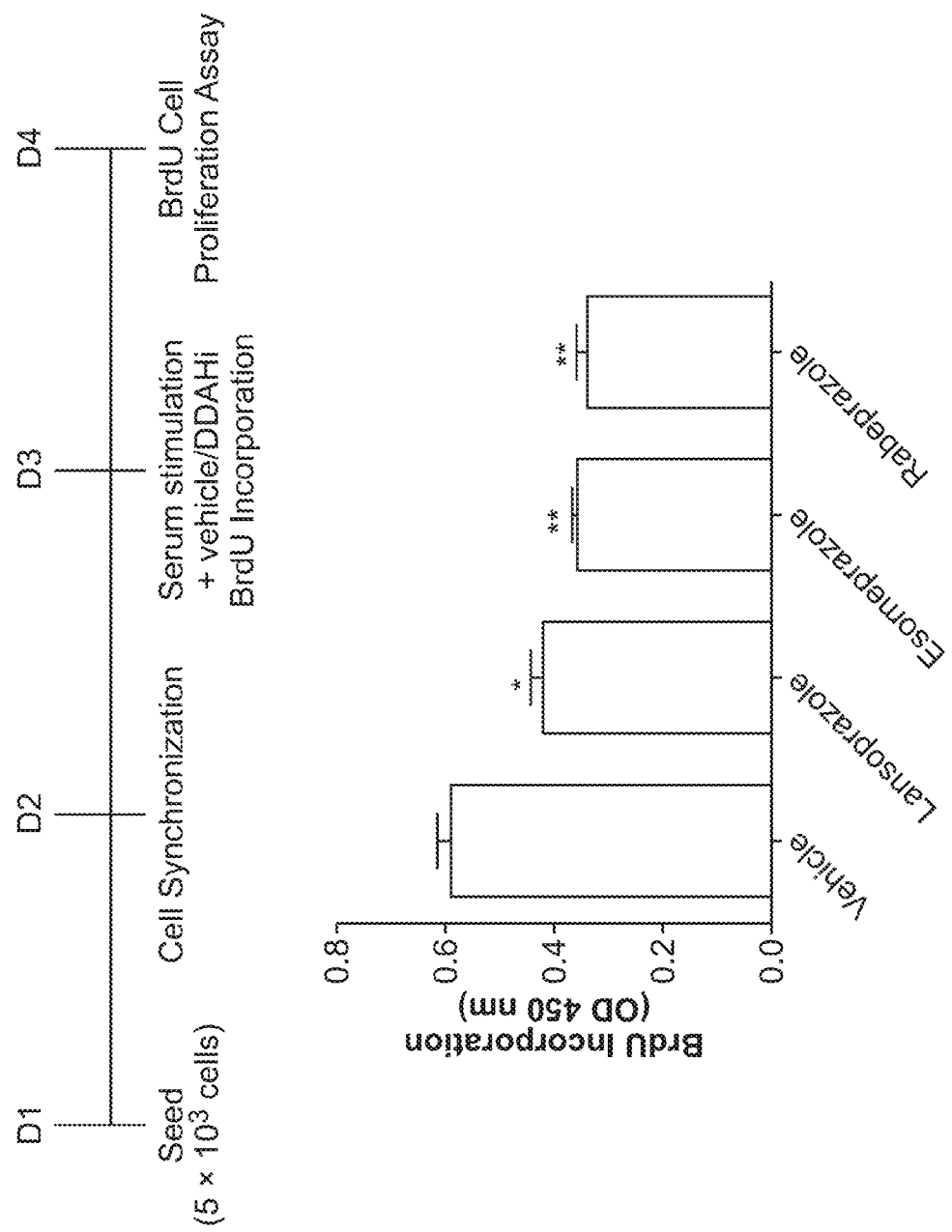
FIG. 19 depicts the effect of PPIs on lung alveolar epithelial cell proliferation.

The results are shown in FIG. 19. The cells seeded in the absence of the DDAH inhibitors showed continued incorporation of BrdU indicating active proliferation. However, the treatment PPIs significantly reduced the incorporation of BrdU indicating inhibition of active cell proliferation. This finding indicates that inhibition of DDAH using the PPIs can regulate the over-proliferation of alveolar epithelial cells as seen in lung fibrosis.

FIG. 19. Treatment with proton pump inhibitors (PPIs; 20 μM) ameliorated serum-induced lung alveolar epithelial cell proliferation. Human lung epithelial cell line (A-549) cells were rendered quiescent, then serum-stimulated to induced re-entry into the cell cycle. BrdU (4 h) incorporation was assessed. Data are mean±SEM (duplicates).

Example 7

Inhibition of DDAH by PPIs is Reversible

In order to understand the mechanism by which PPIs inhibit DDAH activity and to determine whether the inhibition mechanism is reversible, a dilution study was conducted, in which DDAH (at a 100-fold excess to the final concentration used) was pre-incubated with excess PPI (100×, 10× or 1× the $IC_{50}$ value) and then inhibition of enzymatic activity was determined using a fluorometric assay as described above. For a reversible inhibitor that binds to a single site of an enzyme (1:1 stoichiometry), it is anticipated that inhibition can be saturated.

Figure 20:
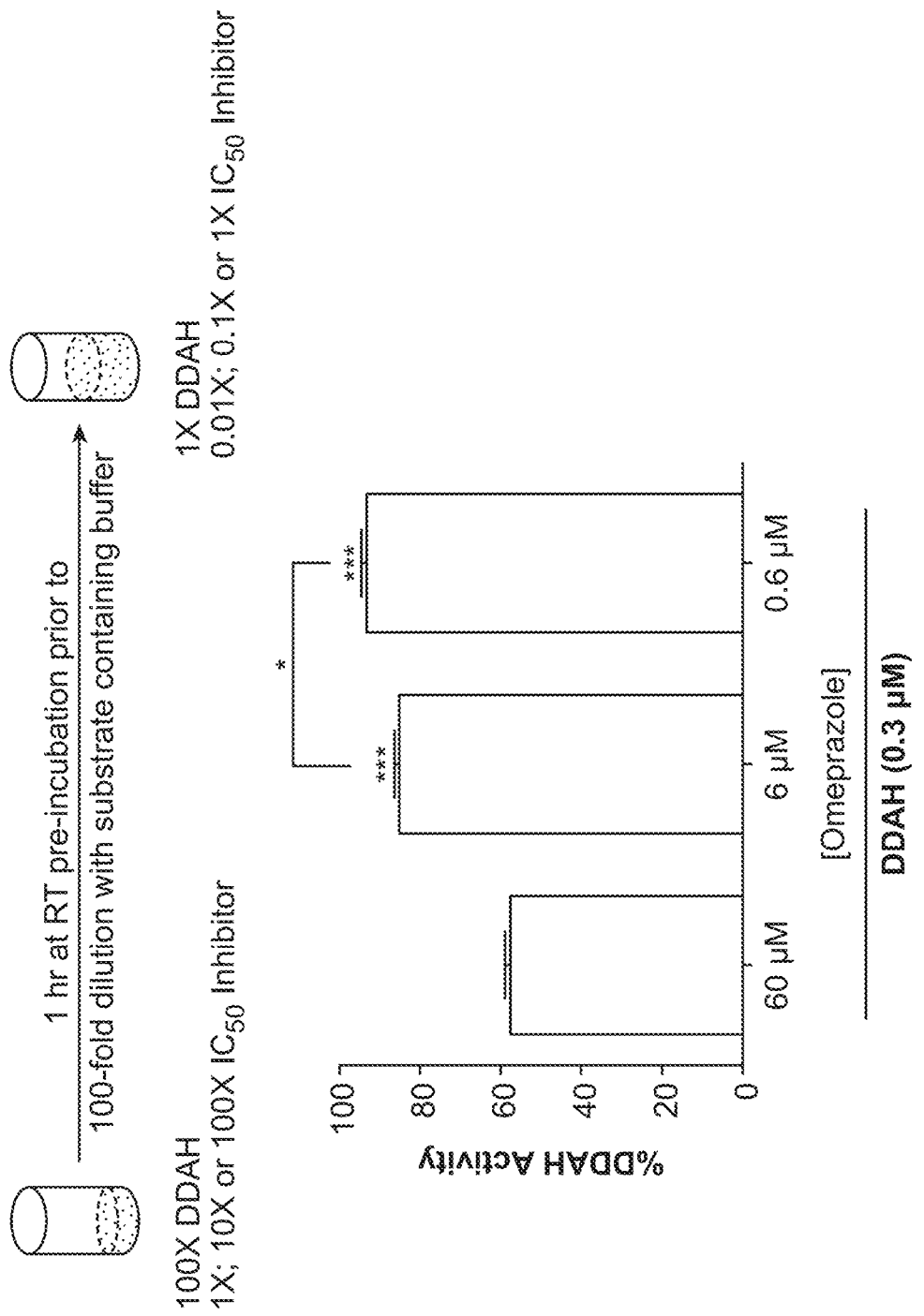
FIG. 20 depicts reversible inhibition of DDAH by PPIs.

The data are shown in FIG. 20. Inhibition of DDAH activity by PPIs was found to be reversible upon dilution of the inhibitors; hence the enzymatic activity of DDAH was shown to recover (Figure). This mode of enzymatic inhibition by small molecules is a pharmacologically desirable property.

FIG. 20. A dilution assay demonstrating reversible inhibition of DDAH activity by PPIs. Omeprazole ($IC_{50}$~60 μM) showed reversible inhibition of DDAH as indicated by DDAH enzymatic activity recovery upon dilution of the inhibitor.

Example 8

Effect of a PPI (Omeprazole) on Cellular ADMA

Figure 21:
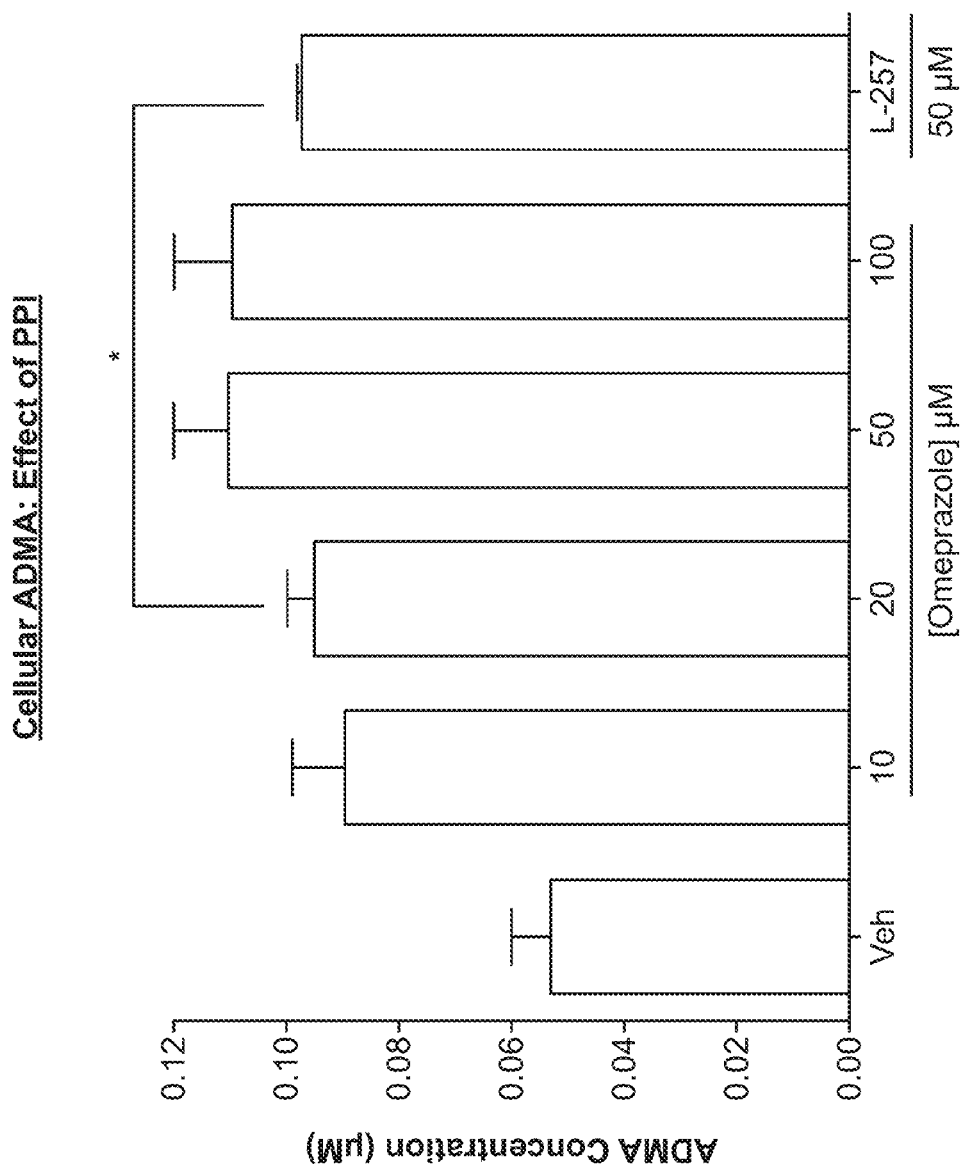
FIG. 21 is a graph showing the effect of PPI (Omeprazole) on cellular ADMA.

To test the effects of a PPI (Omeprazole) on intracellular ADMA production, human lung epithelial cells (A-549) were treated with vehicle, PPI (Omeprazole at 10, 20, 50 or 100 μM) or a known DDAH inhibitor (L-257; Leiper J et al; Nature Med 2007; 13(2): 198-203) for 24 hours. After 24 hours, ADMA was measured by enzyme-linked immunosorbent assay (ELISA). As shown in FIG. 21, an increase in intracellular ADMA was observed when human A-549 lung epithelial cells were treated with Omeprazole. Data are Mean±SEM from duplicate experiments. $*p<0.05$ compared to vehicle ("Veh").

Example 9

Effect of PPI on Nitric Oxide Production

To test the effects of PPI (Omeprazole) on nitric oxide production, human alveolar epithelial cells (A-549) were treated with vehicle, PPI (Omeprazole) or a known DDAH inhibitor (L-257; Leiper J et al; Nature Med 2007; 13(2): 198-203) for 24 hours. Total nitrite (NOx) was measured using Griess reaction. Data are Mean±SEM from duplicate experiments. $*p<0.05$.

Figure 22:
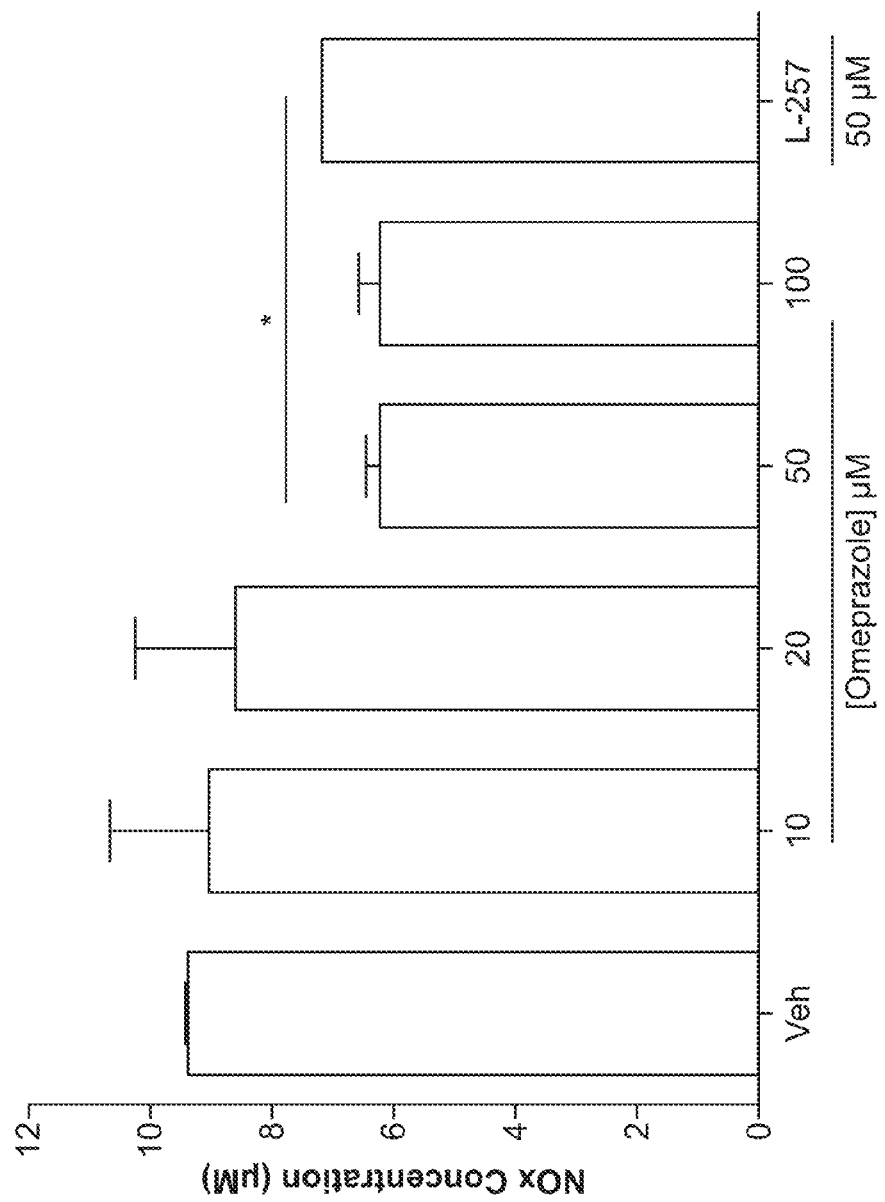
FIG. 22 is a graph showing the effect of PPI on nitric oxide production.

As shown in FIG. 22, Omeprazole reduced the levels of nitric oxide in the human alveolar epithelial cell line.

Example 10

Effect of PPI on Collagen Production by IPF Fibroblasts

Lung fibroblasts were isolated from patients diagnosed with IPF according to International Standards. Isolated fibroblasts were seeded at $6 \times 10^4$ and synchronized the following day. On day-3, the cells were stimulated with serum stimulation in the absence or presence of recombinant transforming growth factor-1 (TGF-β1) in the presence of the proton pump inhibitor Omeprazole (final concentration 50 or 100 μM)); L-257 (final concentration 50 μM) or TGF-131 inhibitor A83-01 (final concentration 20 μM) controls; or vehicle for 24 hours.

The acid-soluble collagen content was determined using the Sircol collagen assay (Accurate Chemical and Scientific Corp; CLRS 1000) following the recommended protocol.

As shown in FIG. 23, the IPF fibroblasts seeded in the presence of TGF-β showed significant elaboration of collagen production compared to the cells seeded in the absence of TGF-β. However, treatment with Omeprazole, L-257, or A83-01 reduced TGF-β induced collagen synthesis. Data are Mean±SEM from duplicate experiments. $*p<0.05$.

Example 11

Effect of PPIs on Alveolar Epithelial Cell Proliferation

To determine the effects of PPI (Omeprazole) on alveolar epithelial cell proliferation, a BrdU Cell Proliferation Assay was carried out. Omeprazole or L-257 control were added to either a human or mouse alveolar epithelial cell sample. A "vehicle only" sample served as a "no DDAH" control.

Figure 25:
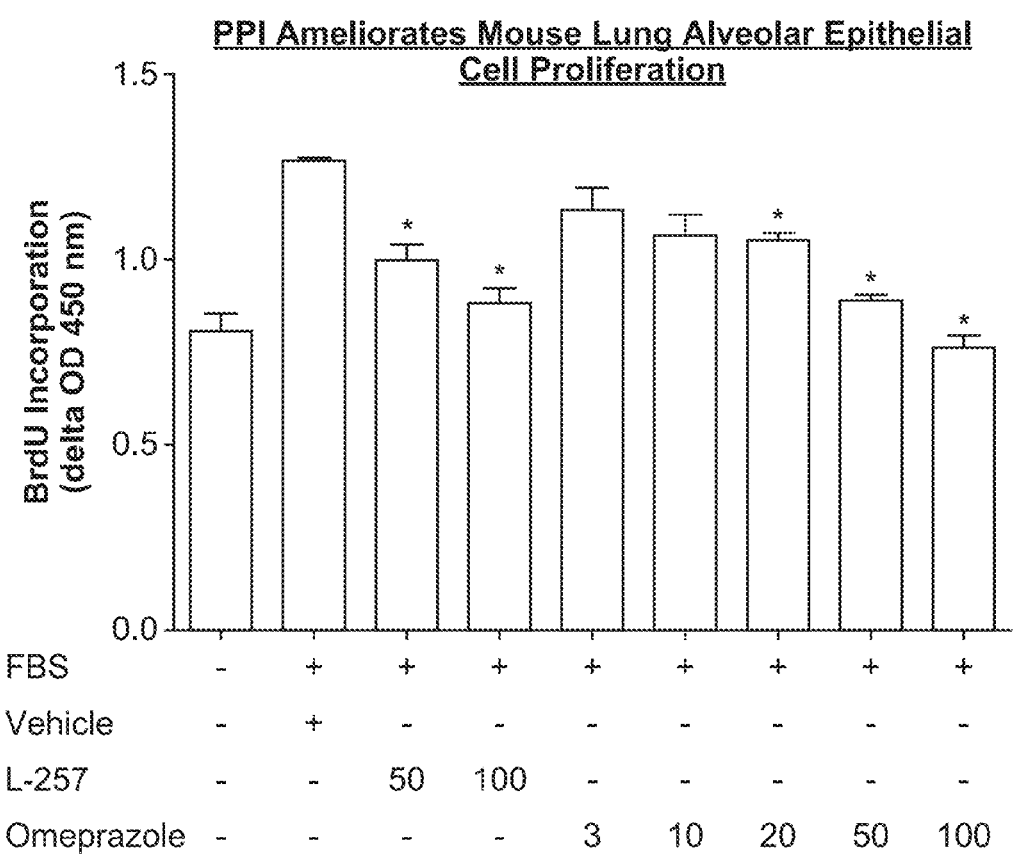
FIG. 25 is a graph showing the effect of PPI on mouse lung alveolar epithelial cell proliferation.

The results are shown in FIGS. 24 and 25. The cells seeded in the absence of the DDAH inhibitors showed continued incorporation of BrdU indicating active proliferation. However, treatment with Omeprazole and L-257 reduced incorporation of BrdU in human (FIG. 24) and mouse cell lines (FIG. 25).

Example 12

Effect of PPI on Apoptosis

Figure 26:
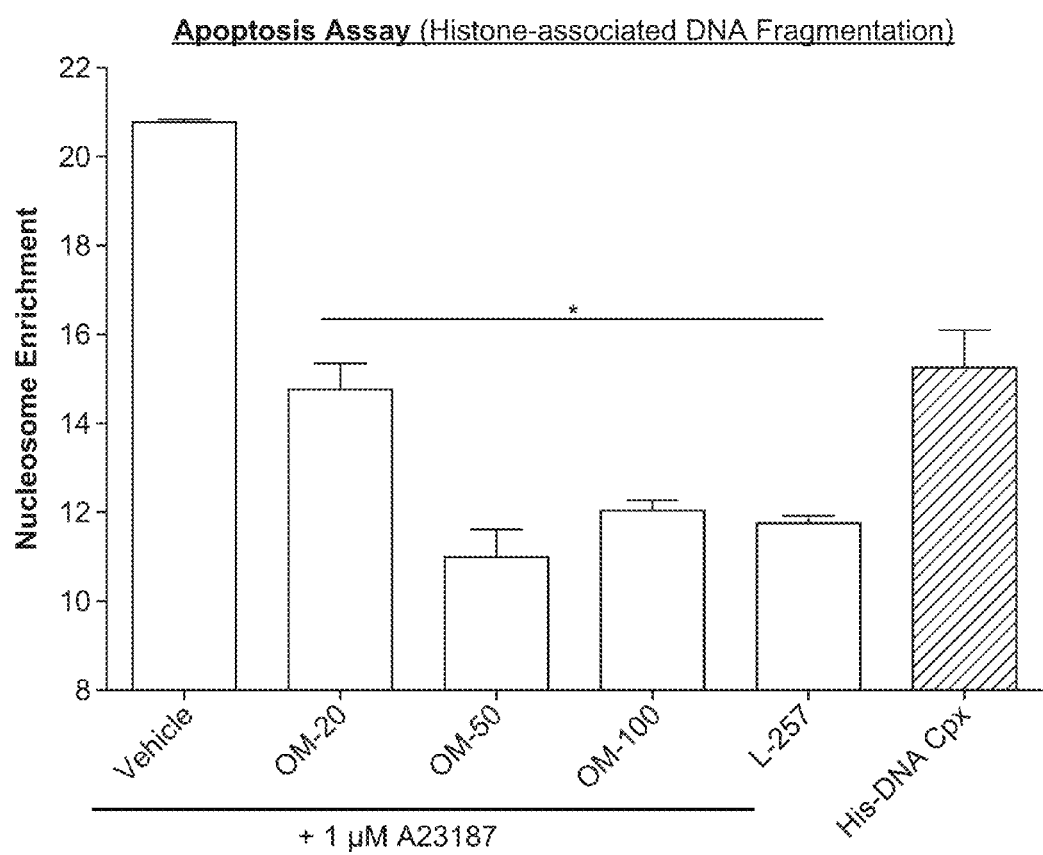
FIG. 26 is a graph showing the effect of PPI on apoptosis in an Endoplasmic Reticulum (ER)-stressed human alveolar epithelial cell-line (A-549).

To test the effects of PPI (Omeprazole) on human alveolar epithelial cell apoptosis, human alveolar epithelial cells (A-549) were treated with vehicle, PPI (Omeprazole) or a known DDAH inhibitor (L-257; Leiper J et al; Nature Med 2007; 13(2): 198-203) in the presence of an apoptosis-inducer (1 μM A23187) for 24 hours. Apoptosis as measured by mono- and oligo-nucleosome enrichment was determined using Cell Death Detection ELISA$^{PLUS}$ (Roche). Histone-DNA complex (His-DNA CPx) was included as a control. As shown in FIG. 26, Omeprazole reduced the level of apoptosis in human alveolar epithelial cells. Data shown are Mean+/−SEM from Duplicate Experiments. * p<0.05.

Example 13

Figure 27:
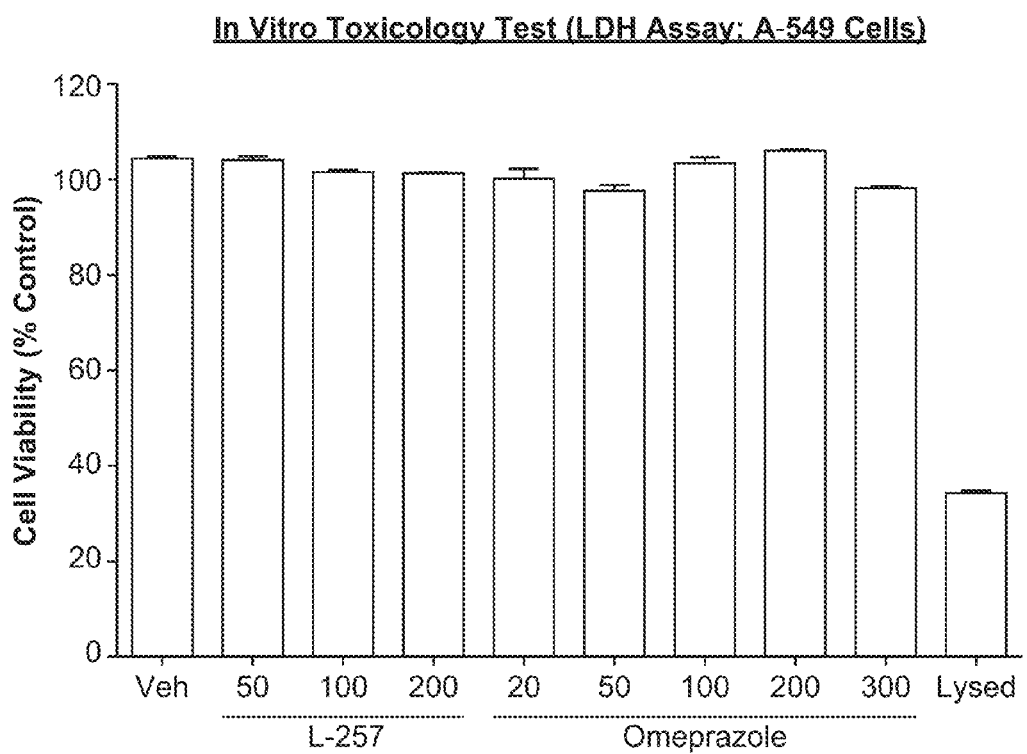
FIG. 27 is a graph showing an in vitro toxicology test of human alveolar epithelial cell-line (A-549) tested with PPIs.
Figure 28:
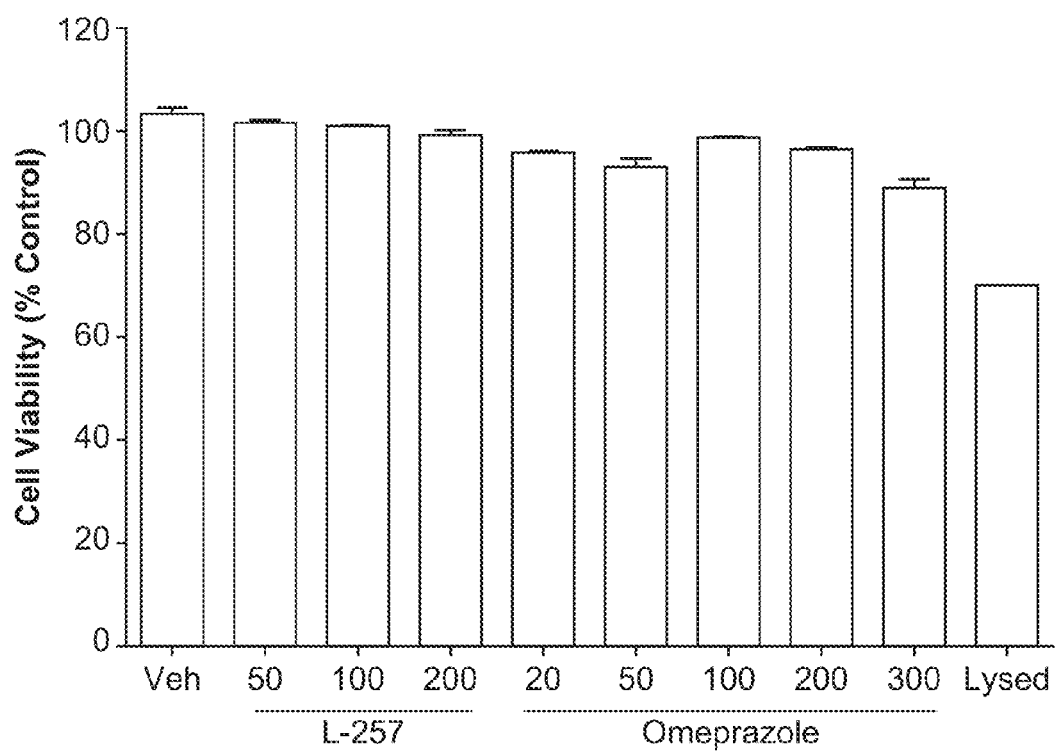
FIG. 28 is a graph showing an in vitro toxicology test of mouse alveolar epithelial cell-line (A-549) tested with PPIs.

Cytotoxicity of PPIs. To determine whether PPIs are cytotoxic to human alveolar epithelial cells (A-549) were treated with vehicle, or varying concentrations of PPI (Omeprazole) or a known DDAH inhibitor (L-257; Leiper J et al; Nature Med 2007; 13(2): 198-203) and cytotoxicity was assessed by the release of lactate dehydrogenase (LDH) into conditioned media. As shown in FIG. 27, PPI (Omeprazole) is not cytotoxic to human alveolar epithelial cells at least up to 300 μM, a concentration 3-6 fold higher than the concentration of PPIs at which anti-fibrotic, anti-proliferative, and anti-apoptotic effects were observed as described herein. Cytotoxicity was also not observed at least up to 300 μM in mouse alveolar epithelial (MLE-12) cells (FIG. 28). Mean+/−SEM from Duplicate Experiments. * p<0.05.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating an individual suffering from idiopathic pulmonary fibrosis, the method comprising administering to the individual an effective amount of a pharmaceutical formulation comprising:
a) a dimethylarginine dimethylaminohydrolase (DDAH) inhibitor of one of the following formulas:

i) Formula Ia:

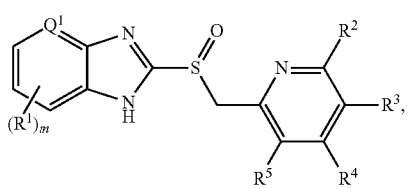

wherein
$Q^1$ is N or CH;
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four;

ii) Formula Ib:

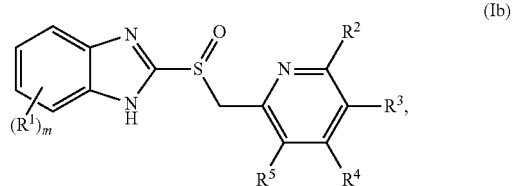

wherein
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four;

iii) Formula Ic:

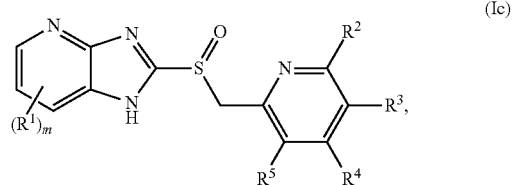

wherein
$R^1$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
$R^2$, $R^3$, $R^4$, and $R^5$ are independently selected from is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; and
m is an integer from zero to four;
and
b) a flowable formulation suitable for delivery by inhalation,
wherein said pharmaceutical formulation is administered locally to the airways wherein the DDAH inhibitor is administered in a dosage range of from about 1 μg to 10 mg.

2. The method of claim 1, wherein the pharmaceutical formulation is administered by inhalation, by insufflating an aerosol comprising the DDAH inhibitor in a dry powder formulation, using a nebulizer.

3. The method of claim 1, wherein the DDAH inhibitor is in an aqueous or ethanolic solution.

4. The method of claim 1, wherein the individual is a human.

5. The method of claim 1, wherein individual does not have gastritis or gastric ulcer.

6. The method of claim 1, wherein the DDAH inhibitor is selected from:

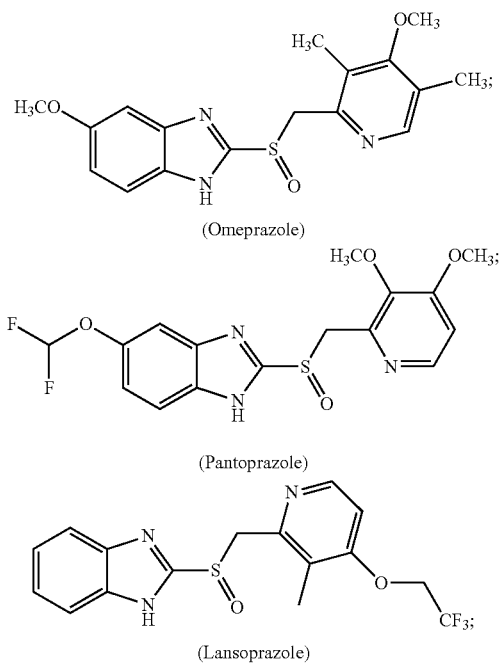

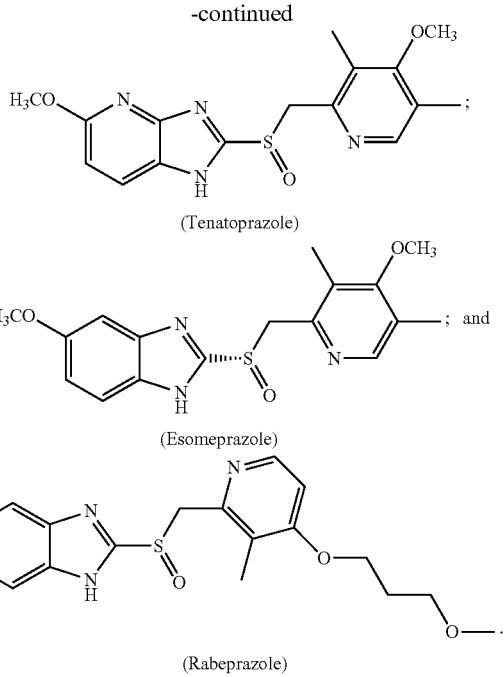

7. The method of claim 1, wherein the pharmaceutical formulation is administered by inhalation using a nebulizer.

8. The method of claim 1, wherein the individual is a non-human mammal.

9. The method of claim 1, wherein the DDAH inhibitor is formulated with a fluid carrier and a propellant.

* * * * *